United States Patent [19]

Takematsu et al.

[11] Patent Number: 4,460,403
[45] Date of Patent: Jul. 17, 1984

[54] 2,3-DICYANO 6 PHENYL PYRAZINE HERBICIDES

[75] Inventors: Tetsuo Takematsu, Utsunomiya; Hirozo Segawa, Nakajyo; Takamaro Miura, Nakajyo; Toshiei Ataka, Nakajyo; Michio Chatani, Nakajyo; Akira Nakamura, Nakajyo, all of Japan

[73] Assignee: Kyowa Gas Chemical Industry Co., Ltd., Tokyo, Japan

[21] Appl. No.: 204,038

[22] Filed: Nov. 4, 1980

Related U.S. Application Data

[62] Division of Ser. No. 969,938, Dec. 15, 1978, abandoned.

[30] Foreign Application Priority Data

Dec. 22, 1977 [JP] Japan .................................. 52-154908
Jan. 20, 1978 [JP] Japan .................................. 53-4245
Jan. 20, 1978 [JP] Japan .................................. 53-4246
Jul. 26, 1978 [JP] Japan .................................. 53-90343

[51] Int. Cl.³ .................. C07D 241/26; C07D 241/24; A01N 43/60
[52] U.S. Cl. ........................................ 71/93; 544/120; 544/408; 71/92
[58] Field of Search ................ 71/92; 544/408, 336, 544/409, 120; 97/93

[56] References Cited

U.S. PATENT DOCUMENTS

| 2,978,310 | 4/1961  | Daams et al. | 71/105  |
| 3,763,161 | 10/1973 | Hartter      | 544/408 |
| 3,879,394 | 4/1975  | Donald       | 544/409 |
| 3,928,352 | 12/1975 | Taylor       | 544/336 |
| 3,940,392 | 2/1976  | Johnston     | 544/408 |
| 4,054,655 | 10/1977 | Donald       | 424/250 |
| 4,101,546 | 7/1978  | Mixan        | 544/408 |
| 4,113,724 | 9/1978  | Portnoy      | 424/250 |
| 4,259,489 | 3/1981  | Takematsu    | 544/336 |

FOREIGN PATENT DOCUMENTS

| 54-4106480 | 8/1979 | Japan | 71/92 |
| 55-5115874 | 9/1980 | Japan | 71/92 |

OTHER PUBLICATIONS

Klingman, Glenn, *Weed Control as a Science*, Wiley and Sons, New York, (1961), p. 22.

Primary Examiner—Donald G. Daus
Assistant Examiner—G. Hendricks
Attorney, Agent, or Firm—Sherman & Shalloway

[57] ABSTRACT

Novel 2,3-dicyanopyrazine derivatives of the formula

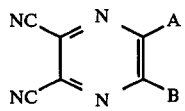

wherein A represents a hydrogen atom, a lower alkyl group, an unsubstituted or substituted phenyl group, a benzyl group, or a group of the formula $-ZR_1$ in which Z represents an oxygen or sulfur atom and $R_1$ represents an unsubstituted or substituted lower alkyl group, a lower alkenyl group, a lower alkynyl group, an unsubstituted or substituted phenyl group, or an unsubstituted or substituted benzyl group; and B represents a halogen atom, an alkyl group containing at least 3 carbon atoms, a phenyl group having a substituent at the ortho- and/or meta-position of the benzene ring, a group of the formula $ZR_1$ in which Z and $R_1$ are as defined, or a group of the formula

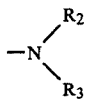

in which $R_2$ and $R_3$, independently from each other, represent a hydrogen atom, an unsubstituted or substituted lower alkyl group, a lower alkenyl group, a cycloalkyl group, an unsubstituted or substituted phenyl group, or an unsubstituted or substituted benzyl group, with the proviso that $R_2$ and $R_3$ do not represent a hydrogen atom at the same time, and $R_2$ and $R_3$ together may form a 3- to 7-membered heterocyclic ring together with the nitrogen atom to which they are bonded, said heterocyclic ring optionally containing an additional hetero atom; and processes for production thereof.

These compounds have high herbicidal activity, and are useful as active ingredients of herbicides.

14 Claims, No Drawings

2,3-DICYANO 6 PHENYL PYRAZINE HERBICIDES

This is a division of application Ser. No. 969,938, filed Dec. 15, 1978, now U.S. Pat. No. 4,259,489 issued on Mar. 31, 1981.

This invention relates to novel pyrazine derivatives, and more specifically to novel 2,3-dicyanopyrazine derivatives having substituents at the 5- and/or 6-position, a process for preparation thereof, and to their use as herbicides.

2,3-Dicyanopyrazine of the following structure having a cyano group (CN) at the 2- and 3-positions of the pyrazine ring has long been known.

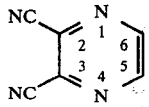 (1)

Little work has been done on this compound partly because of its difficulty of synthesis, and only a few reports have been made on its derivatives having a substituent at the 5- and/or 6-position of the 2,3-dicyanopyrazine.

For example, Japanese Laid-Open Patent Publication No. 59379/75 discloses 2,3-dicyanopyrazine derivatives of the formula

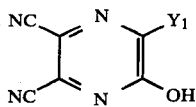 (2)

wherein $Y_1$ represents an alkyl, aryl or carboxyl group, and suggests their utility as intermediates for synthesis in the field of medicines or dyes. However, this Publication does not at all describe anything about their usefulness as herbicides.

U.S. Pat. Nos. 3,879,394 and 4,054,655 disclose 2,3-dicyano-5-chloropyrazine derivatives of the formula

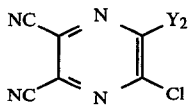 (3)

wherein $Y_2$ represents an amino group which is optionally substituted by an alkyl, alkenyl, alkynyl, cycloalkyl, phenyl or benzyl group; a process for production thereof; and their use as fluorescing agents and fungicides. However, these patents do not suggest their utility as herbicides.

U.S. Pat. No. 3,763,161 discloses 2,3,5-tricyanopyrazine derivatives of the following formula

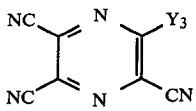 (4)

wherein $Y_3$ represents a cyano, hydroxyl or amino group; a process for preparation thereof, and their use as a growth retarding agent for broad-leaved plants. The compound of formula (4) having at least three cyano groups which are strongly electron-attracting are difficult to produce on an industrial scale because their synthesis involves complicated process steps. The experiments of the present inventors have led to the confirmation that the herbicidal effects of these tricyanopyrazine derivatives are not so high both on broad-leaved weeds and on other weeds.

Ohtsuka reported 2,3-dicyano-5-amino-6-phenylpyrazine in J. Org. Chem., 41, 629 (1976), but did not suggest its utility as a herbicide.

U.S. Pat. No. 3,963,715 discloses that 2-(amino-substituted phenyl) tricyanopyrazines of the formula

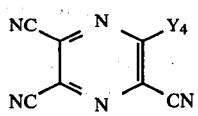 (5)

wherein $Y_4$ represents an amino-substituted phenyl group are useful as dyes and pigments. However, these compounds are difficult to synthesize, and their utility as herbicides is not intended at all in this patent.

U.S. Pat. No. 2,200,689, R. P. Linstead et al., J. Chem. Soc., 1937, 911, V. H. Bredereck et al., Ann. Chem., 600, 95 (1956), and H. R. Rothkopf et al., Chem. Ber., 108, 875 (1975) disclose 2,3-dicyanopyrazine derivatives of the type represented by the following formula

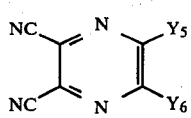 (6)

wherein $Y_5$ and $Y_6$ each represent a hydrogen atom, a methyl group, or a phenyl group. Their herbicidal activity is not at all considered in these literature references.

It is an object of this invention to provide novel 2,3-dicyanopyrazine derivatives.

Another object of this invention is to provide novel 2,3-dicyanopyrazine derivatives substituted at the 5- and/or 6-position which have superior herbicidal activity.

Still another object of this invention is to provide a process for preparing such novel 2,3-dicyanopyrazine derivatives.

A further object of this invention is to provide a herbicide containing such a novel 2,3-dicyanopyrazine derivative.

Other objects and advantages of this invention will become more apparent from the following description.

According to this invention, there is provided a 2,3-dicyanopyrazine derivative of the general formula

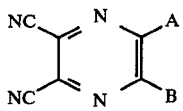 (I)

wherein A represents a hydrogen atom, a lower alkyl group, an unsubstituted or substituted phenyl group, a benzyl group, or a group of the formula $-ZR_1$ in which Z represents an oxygen or sulfur atom and $R_1$ represents an unsubstituted or substituted lower alkyl group, a lower alkenyl group, a lower alkynyl group, an unsubstituted or substituted phenyl group, or an unsubstituted or substituted benzyl group; and B represents a halogen atom, an alkyl group containing at least 3 carbon atoms, a phenyl group having a substituent at the ortho- and/or meta-position of the benzene ring, a group of the formula $ZR_1$ in which Z and $R_1$ are as defined, or a group of the formula

in which $R_2$ and $R_3$, independently from each other, represent a hydrogen atom, an unsubstituted or substituted lower alkyl group, a lower alkenyl group, a cycloalkyl group, an unsubstituted or substituted phenyl group, or an unsubstituted or substituted benzyl group with the proviso that $R_2$ and $R_3$ do not represent a hydrogen atom at the same time, and $R_2$ and $R_3$ together may form a 3- to 7-membered heterocyclic ring together with the nitrogen atom to which they are bonded, said heterocyclic ring optionally containing an additional hetero atom.

It has now been found surprisingly that a group of 2,3-dicyanopyrazine derivatives of general formula (I) have very good herbicidal activity in treatment of the soil of water-submerged paddies, foliage of weeds in the growth period, and the soil of upland farms, and in soil treatment of water-submerged paddies, these compounds generally tend to form a rigid chemical-treated layer in the surface layer of the soil, and have the ability to control barnyard grass and other annual and perennial weeds excellently with substantially no phytotoxicity to transplanted rice plants.

Herbicides provided by this invention exhibit their herbicidal effects in various ways depending upon the types of the substituents in the 2,3-dicyanopyrazine derivatives of formula (I). Some selectively cause chlorosis and withering of weeds which germinate from the surface layer of the paddy soil. Some show the ability to selectively control weeds growing in paddies and wheat farms with substantially no phytotoxicity to rice and wheat. The herbicides of this invention also include those which exhibit outstanding herbicidal effects as soil treating agents applied in small amounts not only in paddies but also in areas where the water content of the soil is relatively small, for example, in uplant farms.

Herbicides containing the compounds of this invention as active ingredients have very high utilitarian values in the agricultural and horticultural fields because they can be applied as pre-emergence and/or post-emergence herbicides to paddies and upland farms both for soil and foliar treatments.

The term "alkyl group", used in the present specification and the appended claims, denotes a linear or branched saturated hydrocarbon group containing not more than 15 carbon atoms, preferably not more than 10 carbon atoms, more preferably not more than 8 carbon atoms, and includes, for example, methyl, ethyl, n- or iso-propyl, n-, iso-, sec- or tert-butyl, n- or iso-pentyl, n-hexyl, n-heptyl, n-octyl, and n-decyl.

The term "lower", used in the present specification and appended claims, means that groups or compounds qualified by this term contain up to 6 carbon atoms, preferably up to 4 carbon atoms, especially preferably up to 3 carbon atoms.

Substituents on the benzene ring in the substituted phenyl group may be those which are usually seen in the field of herbicide chemistry. In the present invention, it is desirable to change the types of the substituents on the benzene ring of the substituted phenyl group according to the substituting position of the phenyl group on the pyrazine ring.

(i) The substituent on the benzene ring of the substituted phenyl group defined for A includes, for example, halogen atoms, lower alkyl groups, lower alkoxy groups, and a nitro group, and the benzene ring may be substituted by 1 to 3 such substituents, preferably only one such substituent. When there are two or more substituents, they may be the same or different. Thus, specific examples of the "unsubstituted or substituted phenyl group" defined for group A include phenyl, m- or p-fluorophenyl, m- or p-chlorophenyl, m- or p-bromophenyl, m- or p-iodophenyl, m- or p-tolyl, m- or p-methoxyphenyl, 3,4-dichlorophenyl, 3,5-dichlorophenyl, 3,5-dimethoxyphenyl, and 3-methyl-4-chlorophenyl.

(ii) The substituent on the benzene ring of the "phenyl group having a substituent at the ortho- and/or meta-position on the benzene ring" defined for group B includes, for example, halogen atoms, lower alkyl groups, and lower alkoxy groups. These substituents can occupy one to three of two ortho-positions and two meta-positions of the phenyl group, preferably only one position (either one of the meta- or ortho-position). When there are two or more substituents, they may be the same or different. Thus, specific examples of the substituted phenyl group for B are o- or m-chlorophenyl, o- or m-bromophenyl, o- or m-hydroxyphenyl, o- or m-tolyl, o- or m-ethylphenyl, o- or m-methoxyphenyl, 2,3-dichlorophenyl, 2,3-dimethylphenyl, 3,5-dimethoxyphenyl, and 3-chloro-4-methylphenyl.

(iii) Examples of the substituent on the benzene ring of the substituted phenyl group defined for $R_1$ include halogen atoms, lower alkyl groups, lower alkoxy groups, a carboxyl group, carboxylate salt groups, a nitro group, the group $-OCOR_4$, the group $-OCONHR_4$, the group $-OCH_2COOH$, the group

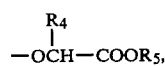

the group $-NHCOOR_4$, the group $-NHCOR_4$, and the group $-NHCONHR_4$, in which $R_4$ and $R_5$, independently from each other, represent a lower alkyl group. The phenyl group may be substituted by 1 to 3, preferably 1 or 2, such substituents. When there are two or more substituents, they may be the same or different. Thus, specific examples of the "unsubstituted or substituted phenyl group" defined for $R_1$ are phenyl, o-, m- or p-chlorophenyl, o-, m- or p-bromophenyl, o-, m- or p-tolyl, o-, m- or p-ethylphenyl, o-, m- or p-methoxyphenyl, p-carboxyphenyl, p-nitrophenyl, p-(acetyloxy)phenyl, p-(N-methylcarbamoyloxy)phenyl, p-(carboxymethoxy)phenyl, p-(acetylamino)phenyl, p-[1-(butoxycarbonyl)ethoxy]phenyl, p-(methoxycarbonylamino)phenyl, m-(dimethylamino)phenyl, 2,4- or 3,4-dichlorophenyl, 2,6-, 3,4- or 3,5-dimethylphenyl, 2-methyl-4-chlorophenyl, 2-methyl-6-chlorophenyl, 3-methyl-4-chlorophenyl, 2-chloro-4-nitrophenyl, 2-methyl-5-nitrophenyl, 3-methyl-4-nitrophenyl, 2- methoxy-4-methylphenyl, 2-methoxy-4-carboxyphenyl, 2,4,5-trichlorophenyl, and 2,4,6-trichlorophenyl.

(iv) Examples of the substituents on the benzene ring of the substituted phenyl group defined for $R_2$ and $R_3$ are halogen atoms, lower alkyl groups, lower alkoxy groups, and haloalkyl groups. The phenyl group may be substituted by 1 to 3, preferably 1 or 2, such substituents. When there are two or more substituents, they may be the same or different. Thus, specific examples of the "unsubstituted or substituted phenyl" defined for $R_2$ and $R_3$ are phenyl, o-, m- or p-chlorophenyl, o-, m- or p-bromophenyl, o-, m- or p-tolyl, o-, m- or p-ethylphenyl, p-n-butylphenyl, o-, m- or p-methoxyphenyl, o-, m- or p-ethoxyphenyl, m-trifluoromethylphenyl, 3,4-dichlorophenyl, 3,5-dimethylphenyl, and 2-methyl-4-chlorophenyl.

Substituents on the "substituted benzyl group" are, for example, halogen atoms, lower alkyl groups, lower alkoxy groups, a carboxyl group, or carboxylate salt groups. Specific examples of the "unsubstituted or substituted benzyl group" are benzyl, α-methylbenzyl, o-, m- or p-chlorobenzyl, m- or p-methylbenzyl, and α-carboxybenzyl.

The "halogen atom" denotes chlorine, bromine, iodine and fluorine atoms. Above all, chlorine, bromine and fluorine are preferred.

In the "lower alkoxy group", the alkyl moiety may be linear or branched. Examples of the lower alkoxy group are methoxy, ethoxy, n- or iso-propoxy, n-, sec-, iso-, or tert-butoxy, and n-pentoxy. Of these, methoxy is preferred.

A trifluoromethyl group is especially preferred as the "lower haloalkyl group".

Substituents on the alkyl chain in the "substituted lower alkyl group" include, for example, halogen atoms, a hydroxyl group, a carboxyl group, carboxylate salt groups, lower alkoxycarbonyl groups, a cyano group, an amino group, mono- or di-lower alkyl amino groups, and lower alkoxy groups. The substituted lower alkyl group may contain one or two, desirably only one, of such substituents. A carboxyl group and lower alkoxycarbonyl groups are especially suitable as the substituent of the "substituted lower alkyl group" for $R_1$. On the other hand, halogen atoms, a hydroxyl group, a carboxyl group, lower alkoxycarbonyl groups, and lower alkoxy groups, above all, the carboxyl group, are suitable as the substituent in the "substituted lower alkyl group" defined for groups $R_2$ and $R_3$. Thus, specific examples of such substituted lower alkyl groups are carboxymethyl, 1- or 2-carboxyethyl, methoxycarbonylmethyl, ethoxycarbonylmethyl, 1-ethoxycarbonylethyl, 2-chloroethyl, 2-bromoethyl, 2-hydroxyethyl, 2-hydroxy-n-propyl, 1,1-dimethyl-2-hydroxyethyl, 1-ethyl-2-hydroxyethyl, 3-hydroxy-n-propyl, 2-ethoxyethyl, 2-aminoethyl, 2-diethylaminoethyl, 3-diethylamino-n-propyl, 1-carboxy-n-propyl, 1-carboxy-n-butyl, 1-carboxy-iso-propyl, 1-carboxy-n-pentyl, 1-carboxy-iso-pentyl, 1-carboxy-n-hexyl, 1-carboxy-3-methylthio-n-propyl, 1-carboxy-1-phenylmethyl, 1-carboxy-2-phenylethyl, 1-carboxy-2-hydroxyethyl, 2-carboxyethyl, 3-carboxy-n-propyl, 1-methoxycarbonylethyl, 1-methoxycarbonyl-n-propyl, 1-ethoxycarbonyl-n-propyl, 1-methoxycarbonyl-n-butyl, 1-ethoxycarbonyl-n-butyl, cyanomethyl, 1-cyanoethyl, 1-cyano-n-propyl, 1,1-dimethyl-1-cyanomethyl, and 2-cyanoethyl.

The "lower alkenyl group" may be linear or branched, are includes, for example, allyl, methylallyl and 2-butenyl. Of these, allyl is most suitable.

A 2-propynyl group is most suitable as the "lower alkynyl group".

Suitable "cycloalkyl groups" include those containing up to 10 carbon atoms, preferably 5 to 8 carbon atoms. Specific examples are cyclopentyl, cyclohexyl, methylcyclohexyl, cycloheptyl, and cyclooctyl. Of these, cyclohexyl is most preferred.

The "3- to 7-membered heterocyclic ring formed by $R_2$ and $R_3$ together with the nitrogen atom to which they are bonded, said heterocyclic ring optionally containing an additional hetero atom" is preferably the one which contains not more than 2, advantageously not more than 1, hetero atom such as a nitrogen, oxygen or sulfur atom, in addition to the nitrogen atom to which $R_2$ and $R_3$ are bonded. Examples of suitable heterocyclic rings are ethylenimino, pyrrolidino, piperidino, hexamethylenimino, piperazino, imidazol-1-yl, 2-methylimidazol-1-yl, morpholino, thiomorpholino, and hexahydro-s-triazino. Of these, ethylenimino, pyrrolidino, piperidino, hexamethylenimino, and morpholino are most suitable.

Among the 2,3-dicyanopyrazine derivatives of general formula (I), a group of preferred compounds are represented by the following formula

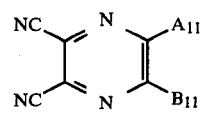
(I-a)

wherein $A_{11}$ represents a hydrogen atom, a lower alkyl group, a phenyl group, or a benzyl group, said phenyl group optionally containing 1 to 3 substituents selected from the group consisting of halogen atoms, lower alkyl groups, lower alkoxy groups and nitro groups, and $B_{11}$ represents a halogen atom; an alkyl group containing 3 to 8 carbon atoms; a phenyl group having 1 to 3 substituents selected from the class consisting of halogen atoms, hydroxyl groups, lower alkyl groups and lower alkoxy groups at the ortho- and/or meta-position on the benzene ring; or a group of the formula $-ZR_{11}$ or

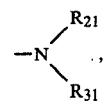

in which Z represents an oxygen or sulfur atom, $R_{11}$ represents an alkyl grop containing 1 to 3 carbon atoms which may have a substituent selected from the class consisting of a carboxyl group and lower alkoxycarbonyl groups, an allyl group, a 2-propynyl group, a phenyl group which may contain 1 to 3 substituents selected from the class consisting of halogen atoms, lower alkyl groups, lower alkoxy groups, nitro groups, groups of the formula $-OCOR_4$, groups of the formula $-OCONHR_4$, a group of the formula $-OCH_2COOH$, groups of the formula

groups of the formula —NHCOOR$_4$, groups of the formula —NHCOR$_4$ and groups of the formula —NHCONHR$_4$, in which R$_4$ and R$_5$, independently from each other, represent a lower alkyl group, or a benzyl group which may be substituted by one halogen atom, and R$_{21}$ and R$_{31}$, independently from each other, represent a hydrogen atom, a lower alkyl group which may have 1 or 2 substituents selected from the class consisting of halogen atoms, phenyl groups, hydroxyl groups, carboxyl groups, cyano groups, lower alkoxy groups, lower dialkylamino groups and lower alkoxycarbonyl groups, an allyl group, a phenyl group which may have 1 or 2 substituents selected from the class consisting of halogen atoms and lower alkyl, lower alkoxy and trifluoromethyl groups, or a benzyl group, with the proviso that R$_{21}$ and R$_{31}$ do not represent a hydrogen atom at the same time, or the group of the formula

is an ethylenimino, pyrrolidino, piperidino, hexamethylenimino or morpholino group.

A group of preferred compounds includes those of the following formula

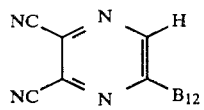

(I-b)

wherein B$_{12}$ represents a chlorine atom; a lower alkyl group containing 3 to 6 carbon atoms; a phenyl group having at the ortho-position or meta-position a substituent selected from the class consisting of chlorine and bromine atoms and hydroxyl, methyl and methoxy groups; a lower alkoxy group containing 1 or 2 carbon atoms; an allyloxy group; a 2-propynyloxy group; a phenoxy group which may have 1 or 2 substituents selected from the class consisting of a chlorine atom, and methyl, methoxy and nitro groups; an ethylthio group; a carboxymethylthio group; or a phenylthio group which may have one substituent selected from the class consisting of a chlorine atom and a methyl group.

Another group of preferred compounds includes those of the following formula

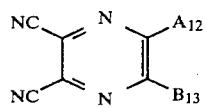

(I-c)

wherein A$_{12}$ represents a lower alkyl group, and B$_{13}$ represents a chlorine atom or an n-propyl, n-butyl, methoxy, ethoxy, allyloxy, 2-propynyloxy, phenoxy, methylthio, ethylthio, carboxymethylthio, phenylthio, benzylthio, methylamino, ethylamino, n- or iso-propylamino, n-, iso-, sec- or tert-butylamino, dimethylamino, phenylamino or benzylamino group. Preferred among the compounds of formula (I-c) are (a) those in which A$_{12}$ represents a methyl group, and B$_{13}$ represents a chlorine atom, or an n-propyl, n-butyl, allyloxy, 2-propynyloxy, methylthio, ethylthio, carboxymethylthio, phenylthio, benzylthio, ethylamino, n- or sec-butylamino, phenylamino or benzylamino group; (b) those in which A$_{12}$ represents an ethyl group, and B$_{13}$ represents a chlorine atom, or an allyloxy, 2-propynyloxy, carboxymethylthio or a n-propylamino group; (c) those in which A$_{12}$ represents an n-propyl group, and B$_{13}$ represents a chlorine atom, or an allyloxy, 2-propynyloxy, methylthio, ethylthio, carboxymethylthio, ethylamino, n-propylamio, or n-, sec-, or tert-butylamino group; and (d) those in which A$_{12}$ represents a n- or iso-butyl, n-pentyl, or n-hexyl group, and B$_{13}$ represents a chlorine atom, or an allyloxy, 2-propynyloxy, carboxymethylthio a methylamino, ethylamino or n-propylamino group.

Still another group of preferred compounds includes those of the formula

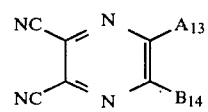

(I-d)

wherein A$_{13}$ represents a phenyl group which may have 1 or 2 substituents selected from the class consisting of halogen atoms and lower alkyl groups containing 1 to 3 carbon atoms; and B$_{14}$ represents a chlorine atom, a methoxy group, an ethoxy group, a methylthio group, an ethylthio group or a group of the formula

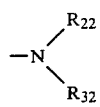

in which R$_{22}$ and R$_{32}$, independently from each other, represent a hydrogen atom; a lower alkyl group which may have a substituent selected from the class consisting of halogen atoms, hydroxyl groups, lower alkoxy groups, carboxyl groups and lower alkoxycarbonyl groups; an allyl group; a phenyl group which may have one substituent selected from the class consisting of halogen atoms, lower alkyl groups and lower alkoxy groups; or a benzyl group, with the proviso that R$_{22}$ and R$_{32}$ do not represent a hydrogen atom at the same time, or the group of the formula

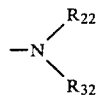

represents an ethylenimino, pyrrolidino or piperidino group. Preferred are those of formula (I-d) in which A$_{13}$ represents a phenyl group which may be substituted by one substituent selected from the class consisting of fluorine chlorine, bromine and iodine atoms and a methyl group, especially a phenyl, m-fluorophenyl, m-chlorophenyl, m-bromophenyl, m-tolyl or p-tolyl group; and B$_{14}$ represents a chlorine atom, or an ethylamino, n-propylamino, n- or iso-butylamino, 1-carboxyethylamino, 1-carboxy-n-propylamino, 1-carboxy-iso-butylamino, 1-carboxy-n-pentylamino, dimethylamino, diethylamino, N-methyl-N-carboxymethylamino, allylamino or ethylenimino group. More preferred are those of formula (I-d) in which A$_{13}$ represents a phenyl, m-fluorophenyl, m-chlorophenyl, m-bromophenyl, m-tolyl or p-tolyl group, and B$_{14}$ represents an ethylamino, n-propylamino or 1-carboxy-n-propylamino group. Especially useful compounds of formula (I-d) are those in which $A_{13}$ represents a phenyl, m-fluorophenyl, m-chlorophenyl or m-tolyl group, and $B_{14}$ represents an n-propylamino group.

Still another group of preferred compounds of formula (I) includes those of formula (I) in which A represents a benzyl group, and B represents an ethylamino or diethylamino group.

Yet another group of preferred compounds of formula (I) are those of the following formula

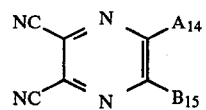

wherein $A_{14}$ represents a lower alkoxy group containing 1 to 4 carbon atoms, an allyloxy group, a 2-propynyloxy group, a phenoxy group which may have 1 to 2 substituents selected from the class consisting of chlorine atoms and methyl groups, a lower alkylthio group containing 1 to 3 carbon atoms, a phenylthio group or a benzylthio group, and $B_{15}$ represents a chlorine atom or an ethylamino or n-propylamino group. Especially preferred species of formula (I-e) are those in which $A_{14}$ represents a methoxy, ethoxy, n- or iso-propoxy, sec-butoxy, phenoxy, ethylthio or n- or iso-propylthio group, and $B_{15}$ represents a chlorine atom.

Typical examples of the novel 2,3-dicyanopyrazine derivatives of the invention represented by formula (I) [including formula (I-a), (I-b), (I-c), (I-d) and (I-e)] include the following in addition to compounds Nos. 1 to 293 shown in Examples 1 to 30 given hereinbelow. 2,3-Dicyano-5-p-acetoxyphenoxy-6-methylpyrazine (m.p. 143°–145° C.), 2,3-dicyano-5-(p-carboxymethoxy)phenoxy-6-methylpyrazine (m.p. 183°–186° C.), 2,3-dicyano-5-p-hydroxyphenoxy-6-n-propylpyrazine (m.p. 146°–148° C.), 2,3-dicyano-5-p-acetoxyphenoxy-6-n-propylpyrazine (m.p. 97°–99° C.), 2,3-dicyano-5-p-(N-methylcarbamoyloxy)phenoxy-6-n-propylpyrazine (m.p. 138°–140° C.), 2,3-dicyano-5-(p-methoxycarbonylamino)phenoxy-6-ethylpyrazine (m.p. 200°–202° C.), 2,3-dicyano-5-allyloxypyrazine ($n_D^{20}$=1.5520), 2,3-dicyano-5-phenoxy-6-methylpyrazine (m.p. 137°–138.5° C.), 2,3-dicyano-5-phenethylamino-6-ethylpyrazine (m.p. 138°–141.5° C.), 2,3-dicyano-5-n-pentylamino-6-n-propylpyrazin (m.p. 83°–85° C.) 2,3-dicyano-5-n-propylamino-6-n-hexylpyrazine (m.p. 81°–83° C.), 2,3-dicyano-5-methylamino-6-iso-butylpyrazine (m.p. 183°–184° C.), 2,3-dicyano-5-methylamino-6-n-propylpyrazine (m.p. 142°–144° C.), 2,3-dicyano-5-p-acetoxyphenoxy-6-n-butylpyrazine (m.p. 84°–86° C.), 2,3-dicyano-5-methylamino-6-n-pentylpyrazine (m.p. 125°–127° C.), 2,3-dicyano-5-benzyloxy-6-n-butylpyrazine (m.p. 91°–93° C.), 2,3-dicyano-5-(carboxymethylamino)pyrazine (m.p. 130°–139° C.), 2,3-dicyano-5-(o-methoxyphenylamino)pyrazine (m.p. 276°–277° C.), 2,3-dicyano-5-pyrrolidino-6-methylpyrazine (m.p. 133°–134° C.), 2,3-dicyano-5-ethylenimino-6-methylpyrazine (m.p. 82°–84° C.), 2,3-dicyano-5-(p-ethoxyphenyl)amino-6-methylpyrazine (195°–198.5° C.), 2,3-dicyano-5-(p-carboxyphenoxy)pyrazine (m.p. 221°–223° C.), 2,3-dicyano-5-(m-dimethylaminophenoxy)pyrazine (m.p. 134°–136° C.), 2,3-dicyano-5-(2-methoxy-4-methylphenoxy)pyrazine (m.p. 140°–141° C.), 2,3-dicyano-5-(2,4,5-trichlorophenoxy)pyrazine (m.p. 120°–121° C.), 2,3-dicyano-5-(2,4,6-trichlorophenoxy)pyrazine (m.p. 160°–162° C.), 2,3-dicyano-5-(1-ethoxycarbonyl)ethoxy-6-p-tolylpyrazine (m.p. 147°–149° C.), 2,3-dicyano-5-(p-ethoxycarbonyl)phenoxy-6-p-chlorophenylpyrazine (m.p. 159°–160° C.), 2,3-dicyano-5-benzylthio-6-phenylpyrazine (m.p. 35°–39.5° C.), 2,3-dicyano-5-p-chlorobenzylthio-6-phenylpyrazine (m.p. 116.5°–117.5° C.), 2,3-dicyano-5-chloro-6-(benzylthio)pyrazine (m.p. 100°–135° C.), 2,3-dicyano-5-chloro-6-(p-chlorobenzylthio)pyrazine (m.p. 76.5°–82.5° C.), 2,3-dicyano-5-n-propylamino-6-(4-chloro-3-methylphenoxy)pyrazine (m.p. 151°–152° C.), 2,3-dicyano-5,6-bis(m-nitrophenoxy)pyrazine (m.p. 235° C. dec.), 2,3-dicyano-5-(α-methylbenzyl)amino-6-n-propylpyrazine (m.p. 84°–86° C.), 2,3-dicyano-5-phenylamino-6-benzylpyrazine (m.p. 192°–193° C.), and 2,3-dicyano-5-benzylamino-6-benzylpyrazine (m.p. 175°–177° C.).

The following 22 compounds are most preferred in this invention because of their especially outstanding herbicidal activities. 2,3-Dicyano-5-ethylamino-6-phenypyrazine, 2,3-dicyano-5-n-propylamino-6-phenylpyrazine, 2,3-dicyano-5-(1-carboxy-n-propyl)amino-6-phenylpyrazine, 2,3-dicyano-5-ethylamino-6-(m-chlorophenyl)pyrazine, 2,3-dicyano-5-n-propylamino-6-(m-chlorophenyl)pyrazine, 2,3-dicyano-5-(1-carboxy-n-propyl)amino-6-(m-chlorophenyl)pyrazine, 2,3-dicyano-5-ethylamino-6-(m-fluorophenyl)pyrazine, 2,3-dicyano-5-n-propylamino-6-(m-fluorophenyl)pyrazine, 2,3-dicyano-5-ethylamino-6-(m-bromophenyl)pyrazine, 2,3-dicyano-5-n-propylamino-6-(m-bromophenyl)pyrazine, 2,3-dicyano-5-(1-carboxy-n-propyl)amino-6-(m-bromophenyl)pyrazine, 2,3-dicyano-5-ethylamino-6-m-tolylpyrazine, 2,3-dicyano-5-n-propylamino-6-m-tolylpyrazine, 2,3-dicyano-5-ethylamino-6-p-tolylpyrazine, 2,3-dicyano-5-n-propylamino-6-p-tolylpyrazine, 2,3-dicyano-5-allyloxy-6-methylpyrazine, 2,3-dicyano-5-allyloxy-6-ethylpyrazine, 2,3-dicyano-5-allyloxy-6-n-propylpyrazine, 2,3-dicyano-5-(2-propynyloxy)-6-n-propylpyrazine, 2,3-dicyano-5-allyloxy-6-n-butylpyrazine, 2,3-dicyano-5-2-propynyloxy)-6-n-butylpyrazine, and 2,3-dicyano-5-allyloxy-6-isobutylpyrazine.

According to this invention, the novel 2,3-dicyanopyrazine derivatives of formula (I) can be prepared by methods described hereinbelow.

[I] A compound of formula (I) in which A represents a hydrogen atom, or a lower alkyl, unsubstituted or substituted phenyl, or benzyl group, and B represents an alkyl group containing at least 3 carbon atoms or a phenyl group having a substituent at the ortho- and/or meta-position of the benzene ring can be prepared by condensing diaminomaleonitrile of formula (IX) with a dicarbonyl compound of formula (II) in accordance with the following reaction scheme:

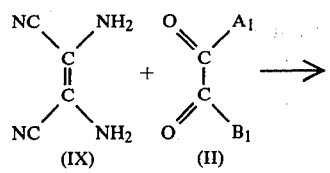

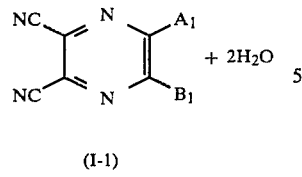

$+ 2H_2O$ (I-1)

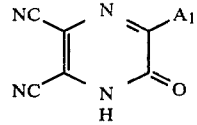

(III')

wherein $A_1$ represents a hydrogen atom, or a lower alkyl, unsubstituted or substituted phenyl, or benzyl group, and $B_1$ represents an alkyl group containing at least 3 carbon atoms or a phenyl group having a substituent at the ortho- and/or meta-position of the benzene ring.

The condensation between the diaminomaleonitrile (IX) and the dicarbonyl compound (II) can be performed usually by contacting them in an inert solvent, for example water, an alcohol such as methanol, ethanol or propanol, an ether such as tetrahydrofuran or dioxane, or a nitrile such as acetonitrile.

The reaction temperature is not critical, and can be varied widely according to the types of the dicarbonyl compound and the solvent. Low temperatures such as room temperature may be used, but preferably, the reaction is carried out at a temperature of at least 40° C., especially at 60° C. to the refluxing temperature of the reaction mixture.

The ratio between the diaminomaleonitrile (IX) and the dicarbonyl compound (II) is not restricted in particular, and can be varied as required. Generally, it is advantageous to use about 1 mole or slightly more than 1 moles (up to about 1.5 moles) of the dicarbonyl compound (II) per mole of the diaminomaleonitrile (IX).

The condensation reaction proceeds in the absence of a catalyst. But if desired, a small amount of a protonic acid such as hydrochloric, sulfuric or acetic acid can be used as a catalyst. The use of the catalyst can shorten the reaction time.

The compound of formula (I-1) can be separated from the reaction mixture, and purified, by methods known per se such as filtration, distillation, extraction, chromatography, recrystallization, or combinations of these.

[II] A compound of formula (I) in which A represents a hydrogen atom, or a lower alkyl, unsubstituted or substituted phenyl, or benzyl group, and B represents a halogen atom can be prepared by halogenating a compound of the formula

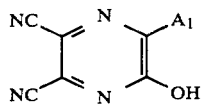

(III)

wherein $A_1$ is as defined hereinabove, obtained from a known α-ketocarboxylic acid and diaminomaleonitrile in the same way as described in [I] above.

The compounds of formula (III) can be expressed also by the following formula (III') because of ketoenol tautomerism. However, in the present application, all of these compounds are expressed by formula (III).

Halogenation of the compound (III) can be performed by treating it with a halogenating agent in the absence of a solvent or in an inert solvent. Examples of suitable inert solvents that can be used are halogenated hydrocarbons such as methylene chloride, dichloroethane, chloroform or carbon tetrachloride, aromatic hydrocarbons such as benzene, toluene, or xylene, and ethers such as dioxane.

All compounds which are frequently used to convert hydroxyl groups to halogen atoms can be used as halogenating agents in the above reaction. Examples of suitable halogenating agents are phosphorus pentahalides such as phosphorus pentachloride or phosphorus pentabromide, phosphorus oxyhalides such as phosphorus oxychloride or phosphorus oxybromide, and thionyl halides such as thionyl chloride. Phosphorus oxychloride, phosphorus oxybromide and thionyl chloride are especially advantageous.

The amount of the halogenating agent is not critical. Advantageously, it is used in an amount of at least 1 equivalent, preferably 1.5 to 30 equivalents, per mole of the compound of formula (III). In particular, a halogenating agent which is liquid at room temperature such as phosphorus oxychloride may be used in a large excess to cause it to serve also as a solvent.

The halogenation reaction can be performed generally at room temperature to the refluxing temperature of the reaction mixture, preferably at about 50° C. to the refluxing temperature of the reaction mixture. If desired, the halogenation reaction may be promoted by an organic base such as pyridine, triethylamine, or N,N-dimethylaniline. The amount of the organic base is not critical, and usually it is used in an amount of several percent to substantially an equimolar amount based on the compound of formula (III).

When thionyl chloride is used as a halogenating agent, an amide such as dimethylformamide may be used as a catalyst in an amount of 1 to 5% by weight based on the compound of formula (III).

Under these conditions, the halogenation reaction can be completed usually within 1 to 5 hours.

The compound of the formula

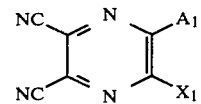

(I-2)

wherein $X_1$ represents a halogen atom, and $A_1$ is as defined above, so prepared can be separated from the reaction mixture, and purified, by methods known per se such as filtration, distillation, extraction, chromatography, recrystallization, or combinations of these.

[III] A compound of formula (I) in which A represents a group of the formula —$ZR_1$ (Z and $R_1$ are as defined hereinabove), and B represents a halogen atom can be prepared by reacting a 2,3-dicyano-5,6-dihalopyrazine of the general formula

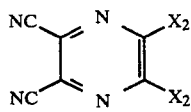

(IV)

wherein $X_2$ represents a halogen atom with a compound of the formula $$HA_2 \quad (V)$$

wherein $A_2$ represents a group of the formula $-ZR_1$ in which Z and $R_1$ are as defined hereinabove.

The reaction of the compound of formula (IV) with the compound of formula (V) can generally be carried out in an inert solvent, for example ketones such as acetone or methyl ethyl ketone, ethers such as tetrahydrofuran or dioxane, and hydrocarbons such as benzene, toluene or xylene.

The amount of the compound (V) to be used is not particularly restricted. Generally, it is desirable to use the compound of formula (V) in an amount of about 1 to about 1.1 moles per mole of the compound of formula (IV).

Desirably, the reaction is carried out in the presence of an acid capturing agent, for example an inorganic or organic base such as sodium hydroxide, sodium carbonate, pyridine or triethylamine. Advantageously, the base is used in an amount of 1 mole to slightly more than 1 moles per mole of the compound of formula (V).

The reaction temperature is not critical, and can be varied widely depending upon the types of the reactants. Generally, relatively low temperatures below about 100° C. are preferred, and the use of room temperature or lower temperatures is advantageous. When the compound of formula (V) is a phenol, a thiol or a thiophenol, a large amount of a compound of formula (IV) in which both halogen atoms at the 5- and 6-positions of the pyrazine ring are substituted is formed as a by-product. It is very desirable in this case to carry out the reaction at low temperatures, and usually, an aqueous solution of the aforesaid organic or inorganic base is added at $-15°$ C. to 0° C. to a mixture of the compound of formula (IV) and the phenol, thiol or thiophenol of formula (V). Under the above conditions, the reaction can be usually terminated in 1 to 5 hours.

When the compound of formula (V) is an alcohol, it may be used in a large excess to cause it to serve also as a solvent. In this case, the compound of formula (I) can be selectively produced by performing the reaction at 60° C. to the refluxing temperature of the reaction mixture for 5 to 20 hours.

The resulting compound of the formula

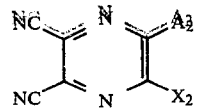

(I-3)

wherein $A_2$ and $X_2$ are as defined hereinabove, can be separated and purified by known procedures such as filtration, distillation, extraction, chromatography, recrystallization, or combinations of these.

[IV] A compound of formula (I) wherein A is as defined hereinabove, and B represents a group of the formula $-ZR_1$ or

in which Z, $R_1$, $R_2$ and $R_3$ are as defined hereinabove can be produced in high yields by reacting a compound of the general formula

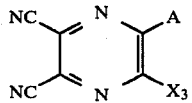

(I-4)

wherein A is as defined hereinabove, and $X_3$ represents a halogen atom, with a compound of the formula $$HB_2 \quad (VI)$$

wherein $B_2$ represents a group of the formula $-ZR_1$ or

in which Z, $R_1$, $R_2$ and $R_3$ are as defined hereinabove.

The reaction of the compound of formula (I-4) with the compound of formula (VI) can generally be carried out in an inert solvent, for example ketones such as acetone or methyl isobutyl ketone, ethers such as tetrahydrofuran or dioxane, esters such as ethyl acetate or butyl acetate, chlorinated hydrocarbons such as chloroform or trichloroethylene, or hydrocarbons such as hexane, heptane, benzene or toluene. In particular, it is suitable to use acetone, tetrahydrofuran, dioxane or benzene in an amount of 1 to 100 parts by weight, advantageously 20 to 50 parts by weight, based on the weight of the compound of formula (I-4).

The reaction may also be performed in a homogeneous or heterogeneous system using a mixture of water and the organic solvent exemplified above.

The reaction temperature is not critical, and can be varied widely according to the types of the reactants used. Generally, relatively low temperature of below about 80° C. are preferred, and the use of room temperature or lower temperatures is advantageous.

The amounts of the compound of formula (VI) is not restricted in particular, and can be varied widely. Generally, it can be used in an amount of about 1 mole to slightly more than 1 moles (usually up to about 2 moles, especially up to 1.5 moles) per mole of the compound of formula (I-4).

The reaction between the compound of formula (I-4) and the compound of formula (VI) is a condensation reaction involving dehydrohalogenation. Usually, it is advantageous to add, as a hydrogen halide capturing agent, an equivalent amount to a lightly excessive amount (preferably up to about 2 equivalents) of an organic base such as pyridine or a tertiary amine (e.g., triethylamine or N,N-dimethylaniline), or an inorganic base such as an alkali metal hydroxide (e.g., sodium hydroxide) or an alkali metal carbonate (e.g., sodium carbonate). When the compound of formula (VI) is an amine, it may be caused to serve also as a hydrogen halide capturing agent by using it in an amount of at least 2 moles per mole of the compound of formula (I-4).

The reaction is generally performed by mixing the compounds of formula (I-4) and (VI) and the hydrogen halide capturing agent, and maintaining the mixture at the above-mentioned reaction temperature for about 10 minutes to about 2 hours.

The resulting compound of the general formula

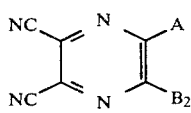 (I-5)

wherein A and $B_2$ are as defined hereinabove, can be separated and purified by known procedures such as filtration, distillation, extraction, chromatography, recrystallization, or combinations of these.

[V] A compound of formula (I) wherein A and B represent a group of the formula —$ZR_1$ in which Z and $R_1$ are as defined hereinabove can be produced in good yields by reacting a 2,3-dicyano-5,6-dihalopyrazine of the general formula

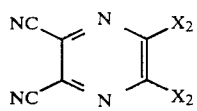 (IV)

wherein $X_2$ is as defined hereinabove, with a compound of the formula $HA_2$ (V)

wherein $A_2$ is as defined hereinabove.

The reaction of the compound of formula (IV) with the compound of formula (V) can be performed substantially in the same way as described in section [III] above except that the compound of formula (V) is used in an amount of at least 2 moles per mole of the compound of formula (IV).

For example, the reaction can be performed by adding the aforesaid acid capturing agent to a solution of the compounds of formulae (IV) and (V) in the aforesaid solvent at $-5°$ to 20° C. The amount of the acid capturing agent is 1 mole to slightly more than 1 moles per mole of the compound of formula (V).

The resulting compound of the formula

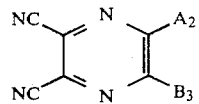 (I-6)

wherein $B_3$ is the same as $A_2$, and $A_2$ is as defined hereinabove, can be separated and purified by known procedures such as filtration, distillation, extraction, chromatography, recrystallization, or combinations of these.

[VI] A compound of formula (I) wherein A represents a group of the formula —$ZR_1$ and B represents a group of the formula

in which Z, $R_1$, $R_2$ and $R_3$ are as defined hereinabove can be prepared by the procedure described in section [IV] above. As an alternative, it can be advantageously produced in good yields by reacting a compound of the general formula

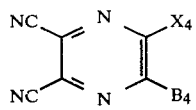 (VII)

wherein $X_4$ represents a halogen atom, and $B_4$ represents a group of the formula

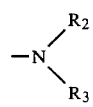

in which $R_2$ and $R_3$ are as defined hereinabove. prepared from the 2,3-dicyano-5,6-dihalopyrazine of formula (IV) and a compound of the formula $HB_4$ (X)

wherein $B_4$ is as defined hereinabove, in a manner similar to the procedure described in [III], with a compound of the formula $HA_2$ (V)

wherein $A_2$ is as defined hereinabove.

The reaction of the compound of formula (VII) with the compound of formula (V) can be performed in the same way as described in [IV] above.

The resulting compound of the general formula

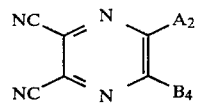 (I-7)

wherein $A_2$ and $B_4$ are as defined hereinabove, can be separated and purified by known procedures such as filtration, distillation, extraction, chromatography, recrystallization, or combinations of these.

The production of the compounds of formula (I) provided by this invention is illustrated in greater detail by the following Examples.

EXAMPLE 1

Preparation of 2,3-dicyano-5-isopropylpyrazine

Selenium dioxide (5.72 g; 0.05 mole) was dissolved in 1 ml of water and 40 ml of dioxane. The solution was heated to 40° to 50° C., and with stirring, 4.31 b (0.05 mole) of 3-methylbutanal was added. The mixture was refluxed with stirring for 4 hours. The precipitated metallic selenium was removed by filtration. To the reaction mixture were added 5.40 g (0.05 mole) of diaminomaleonitrile and 1 ml of acetic acid, and the mixture was refluxed for 3 hours. After the reaction, the solvent was distilled off under reduced pressure. The residue was extracted with 200 ml of benzene, and the oily matter insoluble in benzene was removed. The benzene solution was dried over anhydrous magnesium sulfate, and the solvent was distilled off under reduced pressure to afford 10.70 g of a brown liquid. The liquid was chromatographed on a column containing 100 g of silica gel using benzene-n-hexane (volume ratio 4:1) as an eluent to afford 5.50 g of a yellow liquid. The resulting liquid was further chromatographed on a column containing 80 g of silica gel using benzene-n-hexane (volume ratio 1:1) as an eluent to afford 3.40 g (yield 40%) of 2,3-dicyano-5-isopropylpyrazine.

$n_D^{125} = 1.5308$.

Elemental analysis for $C_9H_8N_4$: Calcd.: C 62.78, H 4.68, N 32.54. Found: C 62.60, H 4.85, N 32.50.

IR (neat) cm$^{-1}$: $\nu_{C\equiv N}$ 2240.

NMR (CDCl$_3$) δppm: 8.85 (s. 1H), 3.36 (m. 1H), 1.42 (d 6H).

By Example 1 and similar procedures, compounds Nos. 1 to 10, 87 and 88 shown in Table 1 were synthesized.

EXAMPLE 2

Preparation of 2,3-dicyano-5-(m-methoxyphenyl)pyrazine

Selenium dioxide (5.72 g; 0.05 mole) was dissolved in 1 ml of water and 50 ml of dioxane, and after adding 7.5 g (0.05 mole) of m-methoxyacetophenone, the mixture was refluxed with stirring for 3.5 hours. The mixture was hot-filtered, and the precipitated metallic selenium was removed. Then, 5.0 g of diaminomaleonitrile and 1 ml of acetic acid were added, and the mixture was stirred at 90° C. for 1 hour. After the reaction, the reaction mixture was cooled to room temperature. Recrystallization of the precipitated crystals from ethanol afforded 6.9 g (yield 58%) of 2,3-dicyano-5-(m-methoxyphenyl)pyrazine.

Melting point: 139°–140° C.

Elemental analysis for $C_{13}H_8N_4O$: Calcd.: C 66.10, H 3.41, N 23.72. Found: C 66.32, H 3.15, N 23.51.

IR (KBr) cm$^{-1}$: $\nu_{C\equiv N}$ 2240.

By example 2 and similar procedures, compounds Nos. 11 to 19 shown in Table 1 were synthesized.

EXAMPLE 3

Preparation of 2,3-dicyano-5-chloropyrazine 2,3-Dicyano-5-hydroxypyrazine (7.30 g; 0.05 mole) was dissolved in 70 g (0.59 mole) of thionyl chloride, and the solution was cooled to 0° to 5° C. With stirring, 4.80 g (0.06 mole) of pyridine was added dropwise over the period of 15 minutes. Then, the mixture was stirred at 70° C. for 2 hours. After the reaction, the excess of thionyl chloride was distilled off under reduced pressure, and the residue was extracted with 150 ml of chloroform. The chloroform solution was washed twice with 50 ml of water, and dried over anhydrous calcium chloride, and then the solvent was distilled off to afford a red solid. Recrystallization of the solid from benzene afforded 6.30 g (yield 77%) of 2,3-dicyano-5-chloropyrazine.

Melting point: 89°–90° C.

Elemental analysis for $C_6HN_4Cl$: Calcd.: C 43.79, H 0.61, N 34.05. Found: C 43.75, H 0.61, N 34.13.

IR (KBr) cm$^{-1}$: $\nu_{C\equiv N}$ 2230.

EXAMPLE 4

Preparation of 2,3-dicyano-5-chloro-6-n-pentylpyrazine

Ethyl n-hexanoate and diethyl oxalate were subjected to Claisen condensation, and then hydrolyzed to form 2-oxo-n-hexanoic acid. This product was then condensed with diaminomaleonitrile to form 9.1 g (0.042 mole) of 2,3-dicyano-5-hydroxy-6-n-pentylpyrazine (m.p. 61°–64° C.). The product was dissolved in 120 g of phosphorus oxychloride, and 3.32 g (0.042 mole) of pyridine was added. The mixture was refluxed for 5 hours, and then worked up in the same way as in Example 3 and the resulting oily product was concentrated under reduced pressure. The resulting product was chromatographed on a silica gel column with benzene as an eluent to afford 6.0 g (yield 61%) of 2,3-dicyano-5-chloro-6-n-pentylpyrazine as a yellow liquid.

$n_D^{25} = 1.5349$.

Elemental analysis for $C_{11}H_{11}N_4Cl$: Calcd.: C 56.30, H 4.73, N 23.87. Found: C 56.57, H 4.60, N 23.52.

IR (KBr) cm$^{-1}$: $\nu_{C\equiv N}$ 2230.

Compounds Nos. 20 to 28 shown in Table 1 were synthesized by Examples 3 and 4 and similar procedures.

EXAMPLE 5

Preparation of 2,3-dicyano-5-chloro-6-phenylpyrazine (1) Synthesis of 2,3-dicyano-5-hydroxy-6-phenylpyrazine Diaminomaleonitrile (5.40 g; 0.05 mole) and 7.50 g (0.05 mole) of benzoylformic acid were put into 50 ml of a 2N aqueous solution of hydrochloric acid. The mixture was stirred at 20° to 30° C. for 30 minutes, and further stirred at 70° to 80° C. for 2 hours. The mixture was then cooled to room temperature. The precipitate formed was collected by filtration, washed thrice with 40 ml of water, and dried under reduced pressure to afford 10.0 g (yield 90%) of 2,3-dicyano-5-hydroxy-6-phenylpyrazine.

Melting point: 221°–223° C. (decomp.).

Elemental analysis for $C_{12}H_6N_4O$: Calcd. C 64.86, H 2.72, N 25.21. Found: C 65.02, H 2.54, N 25.20.

IR (KBr) cm$^{-1}$: $\nu_{OH}$ 2800–2500, $\nu_{C\equiv N}$ 2240.

(2) Synthesis of 2,3-dicyano-5-chloro-6-phenylpyrazine

The 2,3-dicyano-5-hydroxy-6-phenylpyrazine (7.00 g; 0.0315 mole) was dissolved in 40.00 g (0.26 mole) of phosphorus oxychloride, and while the solution was cooled to 5° to 10° C., 3.53 g (0.035 mole) of triethylamine was added dropwise over the period of 20 minutes. After the addition, the mixture was stirred at 70° to 80° C. for 1.5 hours. The reaction mixture was worked up in the same way as in Example 3, and recrystallized from benzene to afford 6.10 g (yield 80%) of 2,3-dicyano-5-chloro-6-phenylpyrazine.

Melting point: 139°–141° C.

Elemental analysis for $C_{12}H_5N_4Cl$: Calcd: C 59.89, H 2.09, N 23.28. Found: C 59.80, H 2.20, N 23.41.

IR (KBr) cm$^{-1}$: $\nu_{C\equiv N}$ 2240.

EXAMPLE 6

Preparation of 2,3-dicyano-5-chloro-6-(m-chlorophenyl)pyrazine 2,3-Dicyano-5-hydroxy-6-(m-chlorophenyl)pyrazine (25.67 g; 0.10 mole) was put into 46.2 g (0.30 mole) of phosphorus oxychloride. The mixture was cooled to 0° to 5° C., and with stirring 10.1 g (0.1 mole) of triethylamine was added dropwise over the period of 30 minutes. After the addition, the mixture was refluxed for 3 hours. The reaction mixture was worked up in the same way as in Example 3. Petroleum ether (50 ml) was added to the resulting oily product, and the precipitate was collected by filtration. Recrystallization from carbon tetrachloride afforded 23.1 g (yield 83%) of 2,3-dicyano-5-chloro-6-(m-chlorophenyl)pyrazine.

Melting point: 87°–88° C.

Elemental analysis for $C_{12}H_4N_4Cl_2$: Calcd.: C 52.39, H 1.47, N 20.37. Found: C 52.38, H 1.61, N 20.24.

IR (KBr) cm$^{-1}$: $\nu_{C\equiv N}$ 2240.

Compounds Nos. 29 to 43 shown in Table 1 were prepared by Examples 5 and 6 and similar procedures.

EXAMPLE 7

Preparation of 2,3-dicyano-5-(p-methylphenoxy)pyrazine 2,3-Dicyano-5-chloropyrazine (0.83 g; 0.005 mole) was dissolved in 25 ml of acetone. The solution was cooled to 0° to 5° C., and with stirring, a solution prepared from 0.54 g (0.005 mole) of p-cresol, 0.21 g (0.005 mole) of sodium hydroxide, 1 ml of water and 15 ml of acetone was added dropwise over the period of 15 minutes. The mixture was stirred at 0° to 5° C. for 1 hour. After the reaction, the solvent was removed by concentration under reduced pressure. The residue was extracted with 100 ml of chloroform. The chloroform solution was washed with 30 ml of a 1N aqueous solution of sodium hydroxide and 30 of water and dried over anhydrous calcium chloride. Then, the solvent was distilled off. Recrystallization of the crude product from ethanol afforded 0.49 g (yield 41%) of 2,3-dicyano-5-(p-methylphenoxy)pyrazine.

Melting point: 126°–127° C.

Elemental analysis for $C_{13}H_8N_4O$: Calcd.: C 66.10, H 3.41, N 23.72. Found: C 66.03, H 3.40, N 23.85.

IR (KBr) cm$^{-1}$: $\nu_{C\equiv N}$ 2240.

EXAMPLE 8

Preparation of 2,3-dicyano-5-(phenylthio)pyrazine 2,3-Dicyano-5-chloropyrazine (0.83 g; 0.005 mole) was dissolved in 25 ml of acetone. The solution was cooled to 0° to 3° C., and with stirring, a solution prepared from 0.55 g (0.005 mole) of thiophenol, 0.21 g (0.005 mole) of sodium hydroxide, 1 ml of water, and 20 ml of acetone was added dropwise over the period of 10 minutes. Then, the reaction mixture was worked up in the same way as in Example 7, and recrystallized from benzene to afford 0.57 g (yield 48%) of 2,3-dicyano-5-(phenylthio)pyrazine.

Melting point: 109°–112° C.

Elemental analysis for $C_{12}H_6N_4S$: Calcd.: C 60.49, H 2.54, N 23.52. Found: C 60.60, H 2.43, N 23.71.

IR (KBr) cm$^{-1}$: $\nu_{C\equiv N}$ 2240.

EXAMPLE 9

Preparation of 2,3-dicyano-5-(carboxymethylthio)pyrazine

Thioglycolic acid (0.92 g; 0.01 mole) and 1.64 g (0.01 mole) of 2,3-dicyano-5-chloropyrazine were dissolved in 40 ml of acetone, and while the solution was cooled to 0° to 5° C., 2.12 g (0.021 mole) of triethylamine was added dropwise. After the addition, the mixture was stirred at 20° to 25° C. for 2 hours. The precipitate was separated by filtration. The filtrate was concentrated under reduced pressure, and 100 ml of a 1% aqueous solution of hydrochloric acid was added. The separated oily product was extracted with 50 ml of ethyl acetate. The ethyl acetate layer was washed twice with 50 ml of a saturated aqueous solution of sodium chloride, dried over anhydrous sodium sulfate, and concentrated under reduced pressure to afford a crude product. Recrystallization from toluene afforded 1.65 g (yield 75%) of 2,3-dicyano-5-(carboxymethylthio)pyrazine.

Melting point: 141°–143° C.

Elemental analysis for $C_8H_4N_4O_2S$: Calcd.: C 43.63, H 1.83, N 25.44. Found: C 43.60, H 1.85, N 25.30.

IR (KBr) cm$^{-1}$: $\nu_{C\equiv N}$ 2240.

EXAMPLE 10

Preparation of 2,3-dicyano-5-phenoxy-6-n-propylpyrazine 2,3-Dicyano-5-chloro-6-n-propylpyrazine (0.207 g; 0.001 mole) was dissolved in 15 ml of acetone, and a solution prepared from 0.094 g (0.001 mole) of phenol, 0.040 g (0.001 mole) of sodium hydroxide, 0.7 ml of water and 5 ml of acetone was added dropwise over the period of 5 minutes. Then, the mixture was stirred at 5° to 10° C. for 10 minutes. The reaction mixture was worked up in the same way as in Example 9, and recrystallized from benzene to afford 0.150 g (yield 57%) of 2,3-dicyano-5-phenoxy-6-propylpyrazine.

Melting point: 130°–132° C.

Elemental analysis for $C_{15}H_{12}N_4O$: Calcd.: C 68.17, H 4.58, N 21.20. Found: C 68.27, H 4.50, N 21.42.

IR (KBr) cm$^{-1}$: $\nu_{CH}$ 2980, $\nu_{C\equiv N}$ 2240.

EXAMPLE 11

Preparation of 2,3-dicyano-5-ethylthio-6-methylpyrazine 2,3-Dicyano-5-chloro-6-methylpyrazine (1.79 g; 0.01 mole), 0.62 g (0.01 mole) of ethanethiol and 0.40 g (0.01 mole) of sodium hydroxide were worked up in the same way as in Example 8. Recrystallization from ethanol afforded 0.91 g (yield 45%) of 2,3-dicyano-5-ethylthio-6-methylpyrazine.

Melting point: 91.5°–92.5° C.

Elemental analysis for $C_9H_8N_4S$: Calcd.: C 52.98, H 3.95, N 27.43. Found: C 52.74, H 3.88, N 27.61.

IR (KBr) cm$^{-1}$: $\nu_{C\equiv N}$ 2240.

EXAMPLE 12

Preparation of 2,3-dicyano-5-allyloxy-6-ethylpyrazine 2,3-Dicyano-5-chloro-6-ethylpyrazine (1.35 g; 0.007 mole) was dissolved in 30 ml of acetone, and while the solution was cooled to −5° C., a solution prepared from 20 ml of allylalcohol and 0.16 g (0.007 mole) of sodium was added dropwise. Then, the mixture was stirred for 30 minutes. The reaction mixture was poured into 200 ml of ice water, and the separated oily product was extracted with toluene. The toluene layer was concentrated under reduced pressure to afford a crude product. The resulting crude product was chromatographed on a column containing silica gel using toluene as an eluent to afford 1.00 g (yield 67%) of 2,3-dicyano-5-allyloxy-6-ethylpyrazine.

$n_D^{25} = 1.5319$.

Elemental analysis for $C_{11}H_{10}N_4O$: Calcd.: C 61.67, H 4.71, N 26.15. Found: C 61.46, H 4.83, N 26.01.

IR (neat) cm$^{-1}$: $\nu_{C\equiv N}$ 2240.

By Examples 7 to 12 and similar procedures, compounds Nos. 44 to 73, 89 to 98, 116, 117, 127 to 133, 140, 142 to 144, 148, 150, and 157 to 175 shown in Table 1 were synthesized.

EXAMPLE 13

Preparation of 2,3-dicyano-5-di-n-propylamino-6-ethylpyrazine 2,3-Dicyano-5-chloro-6-ethylpyrazine (1.92 g; 0.01 mole) was dissolved in 30 ml of acetone. The solution was cooled to 0° to 5° C., and with stirring, 2.02 g (0.02 mole) of di-n-propylamine was added dropwise. The mixture was stirred for 30 minutes. The precipitate was separated by filtration. The filtrate was concentrated under reduced pressure to afford a yellow oily product. Water (20 ml) was added to the oily product, and the precipitated white powder was recrystallized from ethanol to afford 1.28 g (yield 50%) of 2,3-dicyano-5-di-n-propylamino-6-ethylpyrazine.

Melting point: 58°–60° C.

Elemental analysis for $C_{14}H_{19}N_5$: Calcd.: C 65.34, H 7.44, N 27.21. Found: C 65.15, H 7.48, N 27.36.

IR (KBr) cm$^{-1}$: $\nu_{CH}$ 2970, $\nu_{C\equiv N}$ 2225.

EXAMPLE 14

Preparation of 2,3-dicyano-5-methylamino-6-n-butyl pyrazine 2,3-Dicyano-5-chloro-6-n-butylpyrazine (2.21 g; 0.01 mole) was dissolved in 30 ml of benzene, and with stirring at 30° C., 1.55 g (0.02 mole) of a 40% aqueous solution of methylamine was added. Then, the mixture was stirred at 30° to 40° C. for 2 hours. The reaction mixture was worked up in the same way as in Example 13 to afford 1.75 g (yield 81%) of 2,3-dicyano-5-methylamino-6-n-butylpyrazine.

Melting point: 143°–145° C.

Elemental analysis for $C_{11}H_{13}N_5$: Calcd.: C 61.38, H 6.09, N 32.54. Found: C 61.60, H 6.12, N 32.28.

IR (KBr) cm$^{-1}$: $\nu_{NH}$ 3370, $\nu_{C\equiv N}$ 2220.

EXAMPLE 15

Preparation of 2,3-dicyano-5-n-propylamino-6-isobutylpyrazine 2,3-Dicyano-5-chloro-6-isobutylpyrazine (1.10 g; 0.005 mole) was dissolved in 20 ml of tetrahydrofuran. The solution was worked up in the same way as in Example 13 using 0.30 g (0.005 mole) of n-propylamine and 0.02 g (0.005 mole) of sodium hydroxide to afford 1.04 g (yield 85%) of 2,3-dicyano-5-n-propylamino-6-isobutylpyrazine.

Melting point: 107°–110° C.

Elemental analysis for $C_{13}H_{17}N_5$: Calcd.: C 64.17, H 7.04, N 28.78. Found: C 64.13, H 7.24, N 28.63.

IR (KBr) cm$^{-1}$: $\nu_{NH}$ 3500, $\nu_{C\equiv N}$ 2230.

EXAMPLE 16

Preparation of 2,3-dicyano-5-diethylamino-6-benzylpyrazine 2,3-Dicyano-5-chloro-6-benzylpyrazine (1.27 g; 0.005 mole) was dissolved in 30 ml of benzene, and the solution was cooled to 5° to 10° C. With stirring, the mixture was worked up in the same way as in Example 13 using 0.80 g (0.01 mole) of diethylamine. Recrystallization from ethanol afforded 1.10 g (yield 75%) of 2,3-dicyano-5-diethylamino-6-benzylpyrazine.

Melting point: 73° to 74° C.

Elemental analysis for $C_{17}H_{17}N_5$: Calcd.: C 70.08, H 5.88, N 24.04. Found: C 70.30, H 5.75, N 23.95.

IR (KBr) cm$^{-1}$: $\nu_{C\equiv N}$ 2230.

By Examples 13 to 16 and similar procedures, compounds Nos. 74 to 86, 99 to 115, 118 to 126, 134 to 139, 141, 145 to 147, 149, and 151 to 156 were shown in Table 1 synthesized.

EXAMPLE 17

Preparation of 2,3-dicyano-5-n-propylamino-6-phenylpyrazine 2,3-Dicyano-5-chloro-6-phenylpyrazine (12.03 g; 0.05 mole) was dissolved in 1,400 ml of toluene. The solution was cooled to 5° to 10° C., and with stirring, 3.25 g (0.055 mole) of n-propylamine was added dropwise over the period of 10 minutes. Subsequently, 55 ml of a 1N aqueous solution of sodium hydroxide was added dropwise over the period of 10 minutes. The mixture was then stirred at 5° to 10° C. for 30 minutes. After the reaction, the reaction mixture was separated into two layers. The toluene layer was concentrated under reduced pressure to obtain a solid. The solid was washed twice with 200 ml of water, dried under reduced pressure, and recrystallized successively from toluene and ethanol to afford 12.1 g (yield 92%) of 2,3-cyano-5-n-propylamino-6-phenylpyrazine.

Melting point: 136°–137° C.

Elemental analysis for $C_{15}H_{13}N_5$: Calcd.: C 68.43, H 4.98, N 26.60. Found: C 68.42, H 5.01, N 26.58.

IR (KBr) cm$^{-1}$: $\nu_{NH}$ 3380, $\nu_{C\equiv N}$ 2225.

NMR (CDCl$_3$) $\delta$ppm: 7.53 (s. 5H), 6.6–6.1 (br. 1H), 3.49 (m. 2H), 1.62 (m. 2H), 0.97 (t. 3H).

EXAMPLE 18

Preparation of 2,3-dicyano-5-ethylamino-6-phenylpyrazine phenylpyrazine 2,3-Dicyano-5-chloro-6-phenylpyrazine (12.03 g; 0.05 mole) and 7.07 g (0.11 mole) of a 70% aqueous solution of ethylamine were worked up in the same way as in Example 13, and recrystallized from toluene to afford 10.98 g (yield 88%) of 2,3-dicyano-5-ethylamino-6-phenylpyrazine.

Melting point: 180° to 181° C.

Elemental analysis for $C_{14}H_{11}N_5$: Calcd.: C 67.45, H 4.45, N 28.10. Found: C 67.51, H 4.52, N 27.97.

IR (KBr) cm$^{-1}$: $\nu_{NH}$ 3380, $\nu_{C\equiv N}$ 2220.

NMR (CDCl$_3$) $\delta_{ppm}$: 7.60 (s. 5H), 5.75–6.05 (br 1H), 3.55 (m. 2H), 1.27 (t. 3H).

EXAMPLE 19

Preparation of 2,3-dicyano-5-ethylamino-6-(m-bromophenyl)pyrazine 2,3-Dicyano-5-chloro-6-(m-bromophenyl)pyrazine (1.15 g; 0.0036 mole) was dissolved in 20 ml of tetrahydrofuran. The solution was cooled to 0° C., and 0.50 g of a 70% aqueous solution of ethylamine was added. The mixture was worked up in the same way as in Example 13, and recrystallized from ethanol to afford 0.95 g (yield 80%) of 2,3-dicyano-5-ethylamino-6-(m-bromophenyl)pyrazine.

Melting point: 127°–127.5° C.

Elemental analysis for $C_{14}H_{10}N_5Br$: Calcd.: C 51.24, H 3.07, N 21.34. Found: C 51.55, H 3.04, N 21.17.

IR (KBr) cm$^{-1}$: $\nu_{NH}$ 3380, $\nu_{CN}$ 2235.

NMR (CDCl₃) $\delta_{ppm}$: 7.39–7.77 (m. 4H), 5.7–6.1 (br. 1H), 3.56 (m 2H), 1.26 (t. 3H).

EXAMPLE 20

Preparation of 2,3-dicyano-5-n-propylamino-6-(m-chlorophenyl)pyrazine 2,3-Dicyano-5-chloro-6-(m-chlorophenyl)pyrazine (1.0 g; 0.0036 mole), 0.24 g (0.004 mole) of n-propylamine and 40 ml of a 0.1N aqueous solution of sodium hydroxide were worked up in the same way as in Example 17, and recrystallized from methanol to afford 0.84 g (yield 78%) of 2,3-dicyano-5-n-propylamino-6-(m-chlorophenyl)pyrazine.

Melting point: 120°–121° C.

Elemental analysis for $C_{15}H_{12}N_5Cl$: Calcd.: C 60.51, H 4.06, N 23.52. Found: C 60.75, H 4.04, N 23.41.

IR (KBr) cm⁻¹: $\nu_{NH}$ 3400, $\nu_{C\equiv N}$ 2230.

NMR (CDCl₃) $\delta_{ppm}$: 7.56–7.68 (m 4H), 5.7–6.1 (br 1H), 3.53 (m 2H), 1.66 (m 2H), 1.00 (t,3H).

EXAMPLE 21

Preparation of 2,3-dicyano-5-ethylamino-6-(m-fluorophenyl)pyrazine 2,3-Dicyano-5-chloro-6-chloro-6-(m-fluorophenyl)-pyrazine (1.00 g; 0.0039 mole) was dissolved in 30 ml of toluene. The solution was cooled to −5° C., and 0.65 g of a 70% aqueous solution of ethylamine was added dropwise. The mixture was stirred at −5° to 0° C. for 30 minutes. The reaction mixture was worked up in the same way as in Example 13, and recrystallized from ethanol to afford 0.63 g (yield 61%) of 2,3-dicyano-5-ethylamino-6-(m-fluorophenyl)pyrazine.

Melting point: 126°–127° C.

Elemental analysis for $C_{14}H_{10}N_5F$: Calcd.: C 62.91, H 3.77, N 26.21. Found: C 62.90, H 3.51, N 26.02.

IR (KBr) cm⁻¹ $\nu_{NH}$ 3350, $\nu_{C\equiv N}$ 2230.

NMR (CDCl₃) $\delta_{ppm}$: 7.28–7.66 (m 4H), 5.80–6.15 (br 1H), 3.60 (m 2H), 1.27 (t 3H).

EXAMPLE 22

Preparation of 2,3-dicyano-5-n-propylamino-6-p-tolylpyrazine 2,3-Dicyano-5-chloro-6-p-tolylpyrazine (1.00 g; 0.0039 mole) and 0.46 g (0.0078 mole) of n-propylamine were worked up in the same way as in Example 13, and then recrystallized from toluene to afford 0.80 g (yield 74%) of 2,3-dicyano-5-n-propylamino-6-p-tolylpyrazine.

Melting point: 115°–116° C.

Elemental analysis for $C_{16}H_{15}N_5$: Calcd: C 69.29, H 5.45, N 25.25. Found: C 69.02, H 5.70, N 25.23.

IR (KBr) cm⁻¹: $\nu_{NH}$ 3390, $\nu_{CN}$ 2230.

NMR (CDCl₃) $\delta_{ppm}$: 7.38–7.60 (q 4H), 6.15–5.80 (br 1H), 3.44 (m 2H), 2.40 (s 3H), 1.58 (m 2H), 0.97 (t 3H).

By Examples 17 to 22 and similar procedures, compounds Nos. 176 to 189, 197, 198, 200 to 206, 208 to 217, 219 to 224, 226 to 233, 236 to 238, 240 to 257, 259, and 260 shown in Table 1 were prepared.

EXAMPLE 23

Preparation of 2,3-dicyano-5-(1-carboxy-n-propyl) amino-6-phenylpyrazine 2,3-Dicyano-5-chloro-6-phenylpyrazine (2.41 g; 0.01 mole) was dissolved in 30 ml of tetrahydrofuran, and with stirring at 15° to 20° C., a solution prepared from 2.04 g (0.02 mole) of DL-α-amino-n-butyric acid, 1.12 g (0.02 mole) of potassium hydroxide and 40 ml of water was added dropwise over the period of 5 minutes. The mixture was then sitrred at 30° C. for 30 minutes. After the reaction, the reactor was cooled with ice, and in the meanwhile, 2 ml of conc. hydrochloric acid was added to the reaction solution. The solution was then extracted with 100 ml of toluene. The toluene layer was washed with 50 ml of a saturated aqueous solution of sodium chloride and 50 ml of water, and the solvent was removed by concentration under reduced pressure to afford a yellowish white solid. Recrystallization of the solid from ethanol afforded 2.63 g (yield 86%) of 2,3-dicyano-5-(1-carboxy-n-propyl)amino-6-phenylpyrazine.

Melting point: 216°–217° C. (decomp.).

Elemental analysis for $C_{16}H_{13}N_5O_2$: Calcd.: C 62.53, H 4.26, N 22.79. Found: C 62.33, H 4.15, N 22.86.

IR (KBr) cm⁻¹: $\nu_{NH}$ 3420, $\nu_{OH}$ 3100–2800, $\nu_{C\equiv N}$ 2230, $\nu_{C=O}$ 1720.

EXAMPLE 24

Preparation of 2,3-dicyano-5-(1-carboxyethyl)amino-6-phenylpyrazine 2,3-Dicyano-5-chloro-6-phenylpyrazine (4.82 g; 0.02 mole) was dissolved in 50 ml of acetone. The solution was cooled to 0° to 5° C., and with stirring, a solution prepared from 1.78 g (0.02 mole) of DL-α-alanine, 1.64 g (0.02 mole) of sodium hydroxide and 40 ml of water was added dropwise over the period of 30 minutes. The mixture was worked up in the same way as in Example 23, and recrystallized from benzene to afford 2.46 g (yield 42%) of 2,3-dicyano-5-(1-carboxyethyl)amino-6-phenylpyrazine.

Melting point: 200°–203° C. (decomp.).

Elemental analysis for $C_{15}H_{11}N_5O_2$: Calcd.: C 61.48, H 3.78, N 23.88. Found: C 61.48, H 3.84, N 23.72.

IR (KBr) cm⁻¹: $\nu_{NH}$ 3410, $\nu_{OH}$ 3200–2900, $\nu_{C\equiv N}$ 2230, $\nu_{C=O}$ 1720.

By Examples 23 and 24 and similar procedures, compounds Nos. 112, 190–196, 199, 207, 218, 225, 234, 235, 239, and 258 shown in Table 1 were prepared.

EXAMPLE 25

Preparation of 2,3-dicyano-5-chloro-6-isopropoxypyrazine

Isopropanol (50 ml) was added to 1.99 g (0.01 mole) of 2,3-dicyano-5,6-dichloropyrazine, and the mixture was refluxed for 10 hours. After the reaction, the isopropanol was distilled off under reduced pressure. The crude product obtained (1.14 g) was chromatographed on a column of silica gel using benzene-n-hexane as an eluent to afford 1.00 g (yield 45%) of 2,3-dicyano-5-chloro-6-isopropoxypyrazine.

Melting point: 48.5°–50° C.

Elemental analysis for $C_9H_7N_4OCl$: Calcd.: C 48.55, H 3.17, N 25.17. Found: C 48.51, H 3.17, N 25.20.

IR (KBr) cm⁻¹: $\nu_{C\equiv N}$ 2240.

By Example 25 and similar procedures, compounds Nos. 261 to 265 shown in Table 1 were synthesized.

EXAMPLE 26

Preparation of 2,3-dicyano-5-chloro-6-phenoxypyrazine 2,3-Dicyano-5,6-dichloropyrazine (1.00 g; 0.005 mole) was dissolved in 50 ml of tetrahydrofuran, and the solution was cooled to −15° to −10° C. A solution of 0.47 g (0.005 mole) of phenol and 0.21 g (0.005 mole) of sodium hydroxide in 25 ml of water was added dropwise over the period of 30 minutes. The mixture was stirred at $-15°$ to $-10°$ C. for 1 hour. The reaction mixture was poured into 100 ml of ice water, and the precipitate was collected by filtration. The precipitate was dissolved in 50 ml of chloroform, washed with 20 ml of a dilute aqueous solution of sodium hyroxide and 30 ml of water, dried over anhydrous calcium chloride, and concentrated under reduced pressure. The crude product was chromatographed on a column containing 60 g of silica gel using benzene as an eluent to afford 0.65 g (yield 50%) of 2,3-dicyano-5-chloro-6-phenoxypyrazine.

Melting point: 115°–118° C.

Elemental analysis for $C_{12}H_5N_4OCl$: Calcd.: C 56.16, H 1.96, N 21.83. Found: C 56.12, H 1.97, N 21.86.

IR (KBr) cm$^{-1}$: $\nu_{C\equiv N}$ 2240.

By Example 26 and similar procedures, compounds Nos. 266 to 270 shown in Table 1 were synthesized.

EXAMPLE 27

Preparation of 2,3-dicyano-5-chloro-6-ethylthiopyrazine 2,3-Dicyano-5,6-dichloropyrazine (1.00 g; 0.005 mole) and 0.47 g of ethanethiol were dissolved in 50 ml of acetone. The solution was cooled to $-15°$ to $-10°$ C., and a solution of 0.40 g (0.005 mole) of pyridine in 40 ml of water was added dropwise over the period of 30 minutes. The mixture was worked up in the same way as in Example 26 to afford 0.33 g (yield 29%) of 2,3-dicyano-5-chloro-6-ethylthiopyrazine.

Melting point: 55.0°–58.5° C.

Elemental analysis for $C_8H_5N_4SCl$: Calcd.: C 42.77, H 2.24, N 24.94. Found: C 42.75, H 2.25, N 24.98.

IR (KBr) cm$^{-1}$: $\nu_{C\equiv N}$ 2245.

By Example 27 and similar procedures, compounds Nos. 271 to 276 shown in Table 1 were synthesized.

EXAMPLE 28

Preparation of 2,3-dicyano-5-ethylamino-6-phenoxypyrazine 2,3-Dicyano-5-ethylamino-6-chloropyrazine (2.07 g; 0.01 mole) was dissolved in 40 ml of tetrahydrofuran. The solution was cooled to 0° to 5° C., and with stirring, a solution prepared from 0.94 g (0.01 mole) of phenol, 0.56 g (0.01 mole) of potassium hydroxide, 5 ml of water and 20 ml of tetrahydrofuran was added dropwise over the period of 10 minutes. Then, the mixture was stirred at 0° to 5° C. for 1 hour. After the reaction, the precipitate was separated by filtration. The filtrate was concentrated under reduced pressure, and the residue was poured into 80 ml of water. The precipitated crystals were collected by filtration, and recrystallized from benzene to afford 2.22 g (yield 84%) of 2,3-dicyano-5-ethylamino-6-phenoxypyrazine.

Melting point: 197°–198° C.

Elemental analysis for $C_{14}H_{11}N_5O$: Calcd.: C 63.39, H 4.18, N 26.40. Found: C 63.40, H 4.08, N 26.40.

IR (KBr) cm$^{-1}$: $\nu_{NH}$ 3340, $\nu_{C\equiv N}$ 2235.

By Example 28 and similar procedures, compounds Nos. 277 to 281 shown in Table 1 were synthesized.

EXAMPLE 29

Preparation of 2,3-dicyano-5-n-propylamino-6-(benzylthio)pyrazine 2,3-Dicyano-6-n-propylamino-6-chloropyrazine (1.11 g; 0.005 mole) and 0.87 g (0.007 mole) of benzylthiol were dissolved in 50 ml of acetone. The solution was cooled to 0° to 5° C. With stirring, a solution prepared from 0.40 g (0.005 mole) of pyridine and 20 ml of water was added dropwise over the period of 30 minutes. The mixture was further stirred at 20° to 30° C. for 1 hour, and concentrated under reduced pressure to remove acetone. The residue was extracted with 100 ml of chloroform. The extract was washed twice with 50 ml of water, dried over anhydrous calcium chloride, and concentrated under reduced pressure to afford a yellowish solid. Recrystallization of the solid from ethanol afforded 0.47 g (yield 30%) of 2,3-dicyano-5-n-propylamino-6-(benzylthio)pyrazine.

Melting point: 153°–155.5°.

Elemental analysis for $C_{16}H_{15}N_5S$: Calcd.: C 62.11, H 4.89, N 22.64. Found: C 62.44, H 4.80, N 22.50.

IR (KBr) cm$^{-1}$: $\nu_{NH}$ 3350, $\nu_{C\equiv N}$ 2240.

By Example 29 and similar procedures, compounds Nos. 282 to 286 shown in Table 1 were synthesized.

EXAMPLE 30

Preparation of 2,3-dicyano-5,6-bis(methylthio)pyrazine 2,3-Dicyano-5,6-dichloropyrazine (1.99 g; 0.01 mole) was dissolved in 30 ml of acetone. The solution was cooled to 0° to 3° C., and with stirring, 7 g of a 20% aqueous solution of sodium salt of methyl mercaptan was added dropwise over the period of 10 minutes. The mixture was further stirred at 0° to 3° C. for 1 hour. After the reaction, the reaction mixture was concentrated under reduced pressure. The resulting yellowish white solid was washed twice with 50 ml of water, dried, and recrystallized from ethanol to afford 1.64 g (yield 74%) of 2,3-dicyano-5,6-bis(methylthio)pyrazine.

Melting point: 139°–142.5° C.

Elemental analysis for $C_8H_6N_4S_2$: Calcd.: C 43.23, H 2.72, N 25.20. Found: C 43.40, H 2.70, N 25.03.

IR (KBr) cm$^{-1}$: $\nu_{C\equiv N}$ 2240.

By Example 30 and similar procedures, compounds Nos. 287 to 293 shown in Table 1 were synthesized.

TABLE 1

Compounds 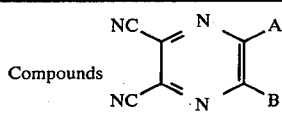

| Compound No. | A | B | $n_D^{25}$ or m.p. (°C.) |
|---|---|---|---|
| 1 | —H | —(CH$_2$)$_2$CH$_3$ | $n_D^{25}=1.5430$ |
| 2 | —H | —(CH$_2$)$_3$CH$_3$ | $n_D^{25}=1.5243$ |
| 3 | —H | —(CH$_2$)$_4$CH$_3$ | $n_D^{25}=1.5210$ |
| 4 | —H | —(CH$_2$)$_5$CH$_3$ | $n_D^{25}=1.5147$ |
| 5 | —H | —(CH$_2$)$_6$CH$_3$ | $n_D^{25}=1.5010$ |
| 6 | —H | —CH(CH$_3$)$_2$ | $n_D^{25}=1.5308$ |

TABLE 1-continued

Compounds:

$$\begin{array}{c}\text{NC}\diagdown\quad\diagup\text{N}\diagdown\quad\diagup\text{A}\\ \text{NC}\diagup\quad\diagdown\text{N}\diagdown\quad\diagup\text{B}\end{array}$$

| Compound No. | A | B | $n_D^{25}$ or m.p. (°C.) |
|---|---|---|---|
| 7 | —H | —CH₂CH(CH₃)₂ | $n_D^{25}$ 1.5218 |
| 8 | —H | —CH(CH₃)CH₂CH₃ | $n_D^{25}$ 1.5347 |
| 9 | —H | —C(CH₃)₃ | 67–68 |
| 10 | —H | —(CH₂)₂CH(CH₃)₂ | $n_D^{25}$ 1.5200 |
| 11 | —H | 3-chlorophenyl | 153.5–155 |
| 12 | —H | 3-bromophenyl | 159–160 |
| 13 | —H | 3-hydroxyphenyl | 200–201 |
| 14 | —H | 3-methylphenyl | 137 |
| 15 | —H | 3-methoxyphenyl | 139–140 |
| 16 | —H | 2-chlorophenyl | 106–107.5 |
| 17 | —H | 2-bromophenyl | 119–120 |
| 18 | —H | 2-methylphenyl | 118–120 |
| 19 | —H | 2-methoxyphenyl | 160–162 |

TABLE 1-continued

Compounds: pyrazine ring with NC, NC, N, N substituents and A, B groups

| Compound No. | A | B | $n_D^{25}$ or m.p. (°C.) |
|---|---|---|---|
| 20 | —H | —Cl | 89–90 |
| 21 | —CH₃ | —Cl | 170 |
| 22 | —CH₂CH₃ | —Cl | 87–88 |
| 23 | —CH₂CH₂CH₃ | —Cl | $n_D^{25} = 1.5494$ |
| 24 | —(CH₂)₃CH₃ | —Cl | $n_D^{25} = 1.5400$ |
| 25 | —(CH₂)₄CH₃ | —Cl | $n_D^{25} = 1.5349$ |
| 26 | —(CH₂)₅CH₃ | —Cl | $n_D^{25} = 1.5130$ |
| 27 | —CH₂CH(CH₃)₂ | —Cl | $n_D^{25} = 1.5372$ |
| 28 | —CH₂—C₆H₅ | —Cl | 73–75 |
| 29 | —C₆H₅ | —Cl | 139–141 |
| 30 | —C₆H₅ | —Br | 136–138 |
| 31 | —C₆H₅ | —I | 156.5–159.5 |
| 32 | —C₆H₄-4-Cl | —Cl | 103–105 |
| 33 | —C₆H₄-4-Br | —Cl | 111–112 |
| 34 | —C₆H₄-4-CH₃ | —Cl | 127–130 |
| 35 | —C₆H₄-3-Cl | —Cl | 87–88 |
| 36 | —C₆H₄-3-F | —Cl | 86–87 |
| 37 | —C₆H₄-3-Br | —Cl | 94.5 |

TABLE 1-continued
Compounds:
$$\text{NC-C(=N)-C(=N)-CN with ring containing A and B}$$
| Compound No. | A | B | $n_D^{25}$ or m.p. (°C.) |
|---|---|---|---|
| 38 | 3-iodophenyl 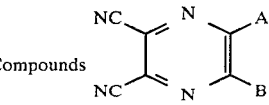 | —Cl | 86–88 |
| 39 | 3-methylphenyl 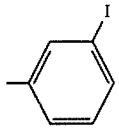 | —Cl | 100–101 |
| 40 | 3-nitrophenyl  | —Cl | 147–149 |
| 41 | 3,5-dimethoxyphenyl 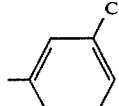 | —Cl | 128–129 |
| 42 | 3,4-dichlorophenyl 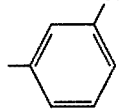 | —Cl | 111–113 |
| 43 | 3,5-dichlorophenyl 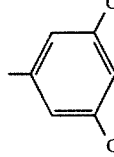 | —Cl | 149–151 |
| 44 | —H | —O—CH₃ | 111 |
| 45 | —H | —O—CH₂CH₃ | 56–57.5 |
| 46 | —H | —O—C₆H₅ 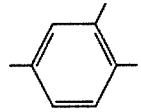 | 150–151 |
| 47 | —H | —O—(2-chlorophenyl) 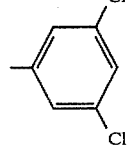 | 105–110 |
| 48 | —H | —O—(4-chlorophenyl) 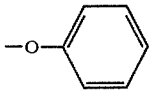 | 139–140 |

TABLE 1-continued
Compounds 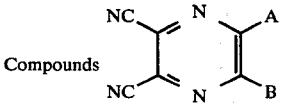
| Compound No. | A | B | $n_D^{25}$ or m.p. (°C.) |
|---|---|---|---|
| 49 | —H | 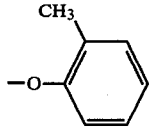 2-methylphenoxy | 92.5–94.5 |
| 50 | —H | 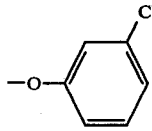 3-methylphenoxy | 108.5–109.5 |
| 51 | —H | 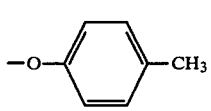 4-methylphenoxy | 126–127 |
| 52 | —H | 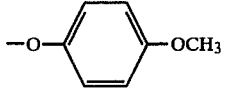 4-methoxyphenoxy | 97–98 |
| 53 | —H | 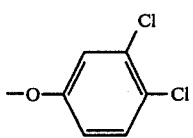 3,4-dichlorophenoxy | 110.5–111 |
| 54 | —H | 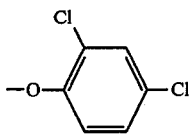 2,4-dichlorophenoxy | 116 |
| 55 | —H | 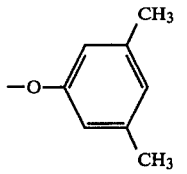 3,5-dimethylphenoxy | 140–141 |
| 56 | —H | 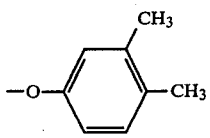 2,4-dimethylphenoxy | 92–93.5 |
| 57 | —H | 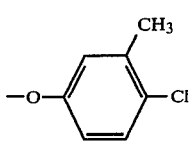 2-chloro-4-methylphenoxy | 104.5–107 |
| 58 | —H | 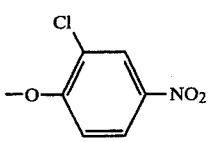 2-chloro-4-nitrophenoxy | 135–136 |

TABLE 1-continued

Compounds: pyrazine ring with NC, NC substituents and =C(A)(B) group

| Compound No. | A | B | $n_D^{25}$ or m.p. (°C.) |
|---|---|---|---|
| 59 | —H | —O—C₆H₄—OCH₂COOH (para) | 183–186 |
| 60 | —H | —O—C₆H₄—O—CH(CH₃)—COO(CH₂)₃CH₃ (para) | 83–85 |
| 61 | —H | —O—C₆H₄—O—C(O)—CH₃ (para) | 129–131 |
| 62 | —H | —O—C₆H₄—O—C(O)—NH—CH₃ (para) | 163–165 |
| 63 | —H | —O—C₆H₄—NH—C(O)—O—CH₃ (para) | 182–183 |
| 64 | —H | —S—CH₂CH₃ | 54–54.5 |
| 65 | —H | —S—CH₂CH₂CH₃ | 84–106 |
| 66 | —H | —S—CH₂COOH | 141–143 |
| 67 | —H | —S—CH₂COOCH₂CH₃ | $n_D^{25}$ 1.4223 |
| 68 | —H | —S—C₆H₅ | 109–112 |
| 69 | —H | —S—C₆H₄—Cl (para) | 96.5–98.5 |
| 70 | —H | —S—C₆H₄—CH₃ (para) | 127–130 |
| 71 | —H | —S—C₆H₄—CH₃ (meta) | 120–122.5 |
| 72 | —H | —S—CH₂—C₆H₅ | 103–105 |
| 73 | —H | —S—CH₂—C₆H₄—Cl (para) | 102.5–103 |
| 74 | —H | —NH—CH₂CH₃ | 86–87 |

TABLE 1-continued

Compounds: pyrazine with NC, NC, N, N, A, B substituents

| Compound No. | A | B | $n_D^{25}$ or m.p. (°C.) |
|---|---|---|---|
| 75 | —H | —NH—(CH₂)₃CH₃ | 60–61.5 |
| 76 | —H | —N(piperidinyl) | 74–75 |
| 77 | —H | —NH—C₆H₅ | 203–204.5 |
| 78 | —H | —NH—(2-Cl-C₆H₄) | 227–228.5 |
| 79 | —H | —NH—(3-Cl-C₆H₄) | 228–229 |
| 80 | —H | —NH—(4-Br-C₆H₄) | 265 dec |
| 81 | —H | —NH—(3,4-Cl₂-C₆H₃) | 232–233 |
| 82 | —H | —N(CH₂CH₃)—C₆H₅ | 98–99 |
| 83 | —H | —NH—CH₂—C₆H₅ | 79–79.5 |
| 84 | —H | —NH—CH(CH₃)—C₆H₅ | 119–120 |
| 85 | —H | —NH—(2-CH₃-4-Cl-C₆H₃) | 190–191 |
| 86 | —H | —NH—(3-CF₃-C₆H₄) | 233–243 |

TABLE 1-continued

Compounds: pyrazine ring with NC, NC substituents on one side and A, B on the other

| Compound No. | A | B | $n_D^{25}$ or m.p. (°C.) |
|---|---|---|---|
| 87 | —CH₃ | —(CH₂)₂CH₃ | 32–33 |
| 88 | —CH₃ | —(CH₂)₃CH₃ | 41–42 |
| 89 | —CH₃ | —O—CH₃ | 138–140 |
| 90 | —CH₃ | —O—CH₂CH₃ | 45–48 |
| 91 | —CH₃ | —O—CH₂CH=CH₂ | $n_D^{25} = 1.5375$ |
| 92 | —CH₃ | —O—(2-bromophenyl) | 133–137 |
| 93 | —O—(4-(NHC(O)NHCH₃)phenyl) | | 228–230 |
| 94 | —CH₃ | —S—CH₃ | 120–121 |
| 95 | —CH₃ | —S—CH₂CH₃ | 91.5–92.5 |
| 96 | —CH₃ | —S—CH₂COOH | 120–122 |
| 97 | —CH₃ | —S—phenyl | 124.5–126 |
| 98 | —CH₃ | —S—CH₂—phenyl | 98–99 |
| 99 | —CH₃ | —NH—CH₂CH₃ | 134–135 |
| 100 | —CH₃ | —NH—CH(CH₃)₂ | 179–181.5 |
| 101 | —CH₃ | —NH—CH₂CH(CH₃)₂ | 150–153 |
| 102 | —CH₃ | —NH—CH(CH₃)—CH₂CH₃ | 161–162 |
| 103 | —CH₃ | —N(CH₃)₂ | 73–74 |
| 104 | —CH₃ | —NH(CH₂)₅CH₃ | 93–94 |
| 105 | —CH₃ | —N(CH₂CH₃)(CH₂CH₂CH₂CH₃) | 33–34.5 |
| 106 | —CH₃ | —N(CH₂CH₂CH₃)₂ | 49.5–52.5 |
| 107 | —CH₃ | —N(piperidinyl) | 81.5–83 |
| 108 | —CH₃ | —N(hexahydroazepinyl) | 85–86 |

TABLE 1-continued

Compounds:

NC—C(=N—C(A)=C(B)—N=)—CN (pyrazine with 2,3-dicyano, 5-A, 6-B)

| Compound No. | A | B | $n_D^{25}$ or m.p. (°C.) |
|---|---|---|---|
| 109 | —CH₃ | —N(morpholino) [—N(CH₂CH₂)₂O] | 100–103 |
| 110 | —CH₃ | —NH—C₆H₅ | 187–189 |
| 111 | —CH₃ | —NH—CH₂—C₆H₅ | 118–119 |
| 112 | —CH₃ | —NH—CH(COOH)(CH₂)₃CH₃ | 158–159.5 |
| 113 | —CH₃ | —NH(CH₂)₃N(CH₂CH₃)₂ | 126–129.5 |
| 114 | —CH₃ | —NH—C₆H₄—CH₃ (para) | 205.5–207 |
| 115 | —CH₃ | —NH—C₆H₄—(CH₂)₃CH₃ (para) | 195–198.5 |
| 116 | —CH₂CH₃ | —OCH₂CH=CH₂ | $n_D^{25}$ 1.5319 |
| 117 | —CH₂CH₃ | —O—C₆H₅ | 100–102 |
| 118 | —CH₂CH₃ | —NH—CH₂CH₃ | 131–133 |
| 119 | —CH₂CH₃ | —NH—CH₂CH₂CH₃ | 116–121 |
| 120 | —CH₂CH₃ | —NH—(CH₂)₃CH₃ | 92–94 |
| 121 | —CH₂CH₃ | —NH—(CH₂)₂CH(CH₃)₂ | 87–90.5 |
| 122 | —CH₂CH₃ | —N(CH₂CH₂CH₃)₂ | 58–60 |
| 123 | —CH₂CH₃ | —N((CH₂)₃CH₃)₂ | $n_D^{25}$ = 1.5569 |
| 124 | —CH₂CH₃ | —NH—C₆H₄—OCH₂CH₃ (ortho) | 220.5–223.5 |

TABLE 1-continued

Compounds:

$$\text{structure with NC groups, N, A, B substituents on a pyrazine ring}$$

| Compound No. | A | B | $n_D^{25}$ or m.p. (°C.) |
|---|---|---|---|
| 125 | —CH₂CH₃ | —NH—(3-ethylphenyl) | 168–171.5 |
| 126 | —CH₂CH₃ | —NH—CH₂—(4-methylphenyl) | 166.5–169.5 |
| 127 | —CH₂CH₃ | —S—CH₂COOH | 126–128 |
| 128 | —CH₂CH₂CH₃ | —O—CH₃ | 95–97 |
| 129 | —CH₂CH₂CH₃ | —O—CH₂—CH=CH₂ | $n_D^{25}$ = 1.5323 |
| 130 | —CH₂CH₂CH₃ | —O—CH₂—C≡CH | 56–58 |
| 131 | —CH₂CH₂CH₃ | —O—phenyl | 130–132 |
| 132 | —CH₂CH₂CH₃ | —S—CH₃ | 85.5–90 |
| 133 | —CH₂CH₂CH₃ | —S—CH₂CH₃ | 28–35 |
| 134 | —CH₂CH₂CH₃ | —NH—CH₂CH₃ | 129–130 |
| 135 | —CH₂CH₂CH₃ | —NH—CH₂CH₂CH₃ | 106–109 |
| 136 | —CH₂CH₂CH₃ | —NH—(CH₂)₃CH₃ | 91–93 |
| 137 | —CH₂CH₂CH₃ | —NHCH₂CH(CH₃)₂ | 108–110 |
| 138 | —CH₂CH₂CH₃ | —NH—CH(CH₃)—CH₂CH₃ | 71–73 |
| 139 | —CH₂CH₂CH₃ | —NH—C(CH₃)₃ | $n_D^{25}$ = 1.5472 |
| 140 | —CH₂CH₂CH₃ | —S—CH₂—COOH | 83–86 |
| 141 | —CH₂CH₂CH₃ | —N(piperidino) | 53–54 |
| 142 | —(CH₂)₃CH₃ | —O—CH₂CH=CH₂ | $n_D^{25}$ = 1.5274 |
| 143 | —(CH₂)₃CH₃ | —O—CH₂—C≡CH | $n_D^{25}$ = 1.5314 |
| 144 | —(CH₂)₃CH₃ | —S—CH₂—COOH | 93–95 |
| 145 | —(CH₂)₃CH₃ | —NH—CH₃ | 143–145 |
| 146 | —(CH₂)₄CH₃ | —NH—CH₂CH₃ | 76–77.5 |
| 147 | —(CH₂)₅CH₃ | —NH—CH₂CH₃ | 71.5–73 |
| 148 | —CH₂CH(CH₃)₂ | —S—CH₂COOH | 92–95 |
| 149 | —CH₂CH(CH₃)₂ | —NH—CH₂CH₃ | 107–110 |
| 150 | —CH₂CH(CH₃)₂ | —O—CH₂CH=CH₂ | 56–58 |
| 151 | —CH₂—phenyl | —NH—CH₃ | 139–140 |
| 152 | —CH₂—phenyl | —NH—CH₂CH₃ | 105–106 |
| 153 | —CH₂—phenyl | —NH—CH₂CH₂CH₃ | 86–90 |

TABLE 1-continued

Compounds: NC-C(=N-)-C(A)=... (pyrazine with 2,3-dicyano and 5-A, 6-B substituents)

| Compound No. | A | B | $n_D^{25}$ or m.p. (°C.) |
|---|---|---|---|
| 154 | —CH₂—C₆H₅ | —NH—CH(CH₃)₂ | 107–110 |
| 155 | —CH₂—C₆H₅ | —N(CH₃)₂ | 121–123 |
| 156 | —CH₂—C₆H₅ | —N(CH₂CH₃)₂ | 73–74 |
| 157 | —CH₂—C₆H₅ | —O—C₆H₅ | 120–125 |
| 158 | —C₆H₅ | —O—CH₃ | 81–82 |
| 159 | —C₆H₅ | —O—CH₂CH₃ | 117–118 |
| 160 | —C₆H₅ | —O—CH(CH₃)₂ | 140–141.5 |
| 161 | —C₆H₅ | —O—CH(CH₃)—COOCH₂CH₃ | 110–111.5 |
| 162 | —C₆H₅ | —O—C₆H₅ | 184–186.5 |
| 163 | —C₆H₅ | —O—C₆H₃(2,4-Cl₂) | 204–205.5 |
| 164 | —C₆H₅ | —S—CH₃ | 110 |
| 165 | —C₆H₅ | —S—CH₂CH₃ | 86–88 |

TABLE 1-continued

Compounds:

$$\text{NC}\diagdown\text{C}=\text{N}\diagdown\text{C}-\text{A}$$
$$\text{NC}\diagup\text{C}=\text{N}\diagup\text{C}-\text{B}$$

| Compound No. | A | B | $n_D^{25}$ or m.p. (°C.) |
|---|---|---|---|
| 166 | phenyl | —S—CH₂COOCH₂CH₃ | 93.5–95 |
| 167 | phenyl | —S—phenyl | 162–163 |
| 168 | phenyl | —S—(4-CH₃-phenyl) | 143–144 |
| 169 | 4-CH₃-phenyl | —O—CH₂CH₃ | 82–85 |
| 170 | 4-CH₃-phenyl | —S—CH₃ | 126–128 |
| 171 | 4-CH₃-phenyl | —S—(CH₂)₂CH₃ | 93–94 |
| 172 | 4-Cl-phenyl | —O—CH₂CH₃ | 117–119 |
| 173 | 4-Cl-phenyl | —O—CH(CH₃)—COOCH₂CH₃ | 121–122 |
| 174 | 4-Cl-phenyl | —S—CH₃ | 155–157 |
| 175 | 4-Cl-phenyl | —S—(CH₂)₂CH₃ | 57–59 |
| 176 | phenyl | —NH—CH₂CH₃ | 180–181 |
| 177 | phenyl | —NH—CH₂CH₂CH₃ | 136–137 |

TABLE 1-continued

Compounds: 
$$\text{structure with NC groups, N ring, A and B substituents}$$

| Compound No. | A | B | $n_D^{25}$ or m.p. (°C.) |
|---|---|---|---|
| 178 | phenyl | —NH—CH₂CH(CH₃)₂ | 134–135 |
| 179 | phenyl | —NH—C(CH₃)₃ | 116–117 |
| 180 | phenyl | —NH—cyclohexyl | 145–146 |
| 181 | phenyl | —N(CH₃)₂ | 131–132 |
| 182 | phenyl | —N(CH₂CH₃)₂ | 105–106 |
| 183 | phenyl | —N(CH₂CH₂CH₃)₂ | 70–71.5 |
| 184 | phenyl | aziridinyl (–N⟨CH₂CH₂⟩) | 132–135 dec |
| 185 | phenyl | pyrrolidinyl | 211–212 |
| 186 | phenyl | piperidinyl | 134–135 |
| 187 | phenyl | hexamethyleneimino | 153–154 |
| 188 | phenyl | morpholino | 185–187 |
| 189 | phenyl | —NH—CH₂CH=CH₂ | 125–126 |

TABLE 1-continued

Compounds $$\text{NC-C(=N-)-C(=N-)-CN with ring bearing A and B}$$

| Compound No. | A | B | $n_D^{25}$ or m.p. (°C.) |
|---|---|---|---|
| 190 | phenyl | —NHCH₂COOH | 235 dec |
| 191 | phenyl | —NH—CH(COOH)—CH₃ | 203–204 dec |
| 192 | phenyl | —NH—CH(COOH)—CH₂CH₃ | 216–217 dec |
| 193 | phenyl | NH—CH(COOH)—CH(CH₃)₂ | 184–186 dec |
| 194 | phenyl | —NH—CH(COOH)—(CH₂)₃CH₃ | 185–186 dec |
| 195 | phenyl | —NH—CH(COOH)—CH₂OH | 183–185 dec |
| 196 | phenyl | —NH—CH(COOH)—C₆H₅ | 150 dec |
| 197 | phenyl | —NH—CH₂COOCH₂CH₃ | 122–124 |
| 198 | phenyl | —NH—CH(COOCH₂CH₃)—CH₂CH₃ | 82–84 |
| 199 | phenyl | —N(CH₃)—CH₂COOH | 177–178 dec |
| 200 | phenyl | —NH—CH₂CH₂—Cl | 153–156 |
| 201 | phenyl | —NH—CH₂CH₂—O—CH₂CH₃ | 123.5–125.5 |

TABLE 1-continued

Compounds: pyrazine ring with NC groups at positions 2,3 and substituents A, B at positions 5,6

| Compound No. | A | B | $n_D^{25}$ or m.p. (°C.) |
|---|---|---|---|
| 202 | phenyl | —NH—NH—(CH₂)₃—O—CH₃ | 115–117 |
| 203 | phenyl | —NH—CH₂—CH(OH)—CH₃ | 127–129 |
| 204 | phenyl | —NH—CH(CH₂OH)—CH₂CH₃ | |
| 205 | phenyl | —NH—CH₂CH₂N(CH₂CH₃)₂ | 96–97.5 |
| 206 | phenyl | —NH—CH₂CH₂—CN | 189–190 |
| 207 | phenyl | —NH—CH₂CH₂—COOH | 155–162 (dec.) |
| 208 | phenyl | —NH—CH₂—phenyl | 156–158 |
| 209 | phenyl | —NH—phenyl | 210–210.5 |
| 210 | phenyl | —NH—(4-Cl-phenyl) | 216–217 |
| 211 | phenyl | —NH—(3-CH₂CH₃-phenyl) | 197–198.5 |
| 212 | phenyl | —NH—(2-OCH₃-phenyl) | 282–283 |

TABLE 1-continued

Compounds: structure with NC, NC on one side of a pyrazine ring with N, N and substituents A and B

| Compound No. | A | B | $n_D^{25}$ or m.p. (°C.) |
|---|---|---|---|
| 213 | 3-Cl-phenyl | —NH—CH₂CH₃ | 117–118 |
| 214 | 3-Cl-phenyl | —NH—CH₂CH₂CH₃ | 120.5–121 |
| 215 | 3-Cl-phenyl | —NH—CH₂ | 190.5–192.5 |
| 216 | 3-Cl-phenyl | —N(CH₂CH₃)₂ | 86.5–87 |
| 217 | 3-Cl-phenyl | —NHCH₂CH=CH₂ | 109–111 |
| 218 | 3-Cl-phenyl | —NH—CH(COOH)—CH₂CH₃ | 182–188 dec |
| 219 | 3-Cl-phenyl | —NH—CH₂—COOCH₂CH₃ | 98–101 |
| 220 | 3-Cl-phenyl | —NH—CH₂CH₂—CN | 175–178 |
| 221 | 3-Cl-phenyl | —NH—CH₂CH₂—OCH₃ | 142–144 |
| 222 | 3-F-phenyl | —NH—CH₂CH₃ | 126–127 |

TABLE 1-continued

Compounds: structure with NC, NC on pyrazine ring with N, N and substituents A and B

| Compound No. | A | B | $n_D^{25}$ or m.p. (°C.) |
|---|---|---|---|
| 223 | 3-F-phenyl | —NH—CH$_2$CH$_2$CH$_3$ | 104.5–105.5 |
| 224 | 3-F-phenyl | —NHCH$_2$CH=CH$_2$ | 126.5–127 |
| 225 | 3-F-phenyl | —NH—CH(COOH)—CH$_3$ | 113–114 dec. |
| 226 | 3-F-phenyl | —NH—CH$_2$CH$_2$—Cl | 114–115 |
| 227 | 3-F-phenyl | —NH—CH$_2$CH$_2$—Br | 109–110.5 |
| 228 | 3-F-phenyl | —N(CH$_2$CH$_3$)$_2$ | 109–110 |
| 229 | 3-Br-phenyl | —NHCH$_2$CH$_3$ | 127–127.5 |
| 230 | 3-Br-phenyl | —NH—CH$_2$CH$_2$CH$_3$ | 126–127 |
| 231 | 3-Br-phenyl | —NH—CH$_2$CH(CH$_3$)$_2$ | 108.5–109 |
| 232 | 3-Br-phenyl | —N(CH$_2$CH$_3$)$_2$ | 91–92 |

TABLE 1-continued

Compounds: $\text{NC-C(=N-C(A)=C(B)-N=C-CN)}$ (pyrazine with 2,3-dicyano and 5-A, 6-B substituents)

| Compound No. | A | B | $n_D^{25}$ or m.p. (°C.) |
|---|---|---|---|
| 233 | 3-Br-phenyl | —NHCH₂CH=CH₂ | 120 |
| 234 | 3-Br-phenyl | —NH—CH(COOH)—CH₃ | 202–206 dec. |
| 235 | 3-Br-phenyl | —NH—CH(COOH)—CH₂CH₃ | 190–194 dec. |
| 236 | 3-CH₃-phenyl | —NH—CH₂CH₃ | 144 |
| 237 | 3-CH₃-phenyl | —NHCH₂CH₂CH₃ | 135–135.5 |
| 238 | 3-CH₃-phenyl | —NHCH₂CH=CH₂ | 145–146 |
| 239 | 3-CH₃-phenyl | —NH—CH(COOH)—CH₃ | 177.5–179 dec |
| 240 | 3-CH₃-phenyl | —NH—CH₂CH₃—Cl | 106–108.5 |
| 241 | 4-CH₃-phenyl | —NH—CH₂CH₃ | 154–155 |
| 242 | 4-CH₃-phenyl | —NH—CH₂CH₂CH₃ | 115–116.5 |

TABLE 1-continued

Compounds: structure with NC, N, A, B substituents on pyrazine ring

| Compound No. | A | B | $n_D^{25}$ or m.p. (°C.) |
|---|---|---|---|
| 243 | 4-CH₃-C₆H₄- | —NH—CH₂CH=CH₂ | 112–113 |
| 244 | 4-Cl-C₆H₄- | —NH—CH₂CH₃ | 153–155 |
| 245 | 4-Cl-C₆H₄- | —NH—CH₂CH₂CH₃ | 145–147 |
| 246 | 4-Cl-C₆H₄- | —NH—CH₂CH=CH₂ | 127–129 |
| 247 | 4-Cl-C₆H₄- | —NH—CH₂CH(OH)—CH₃ | 103–108 |
| 248 | 4-Br-C₆H₄- | —NH—CH₂CH₂CH₃ | 161–162 |
| 249 | 3-I-C₆H₄- | —NH—CH₂CH₂CH₃ | 118–119 |
| 250 | 3-NO₂-C₆H₄- | —NH—CH₂CH₃ | 169–172 |
| 251 | 3-NO₂-C₆H₄- | —NH—CH₂CH₂CH₃ | 141–142 |
| 252 | 3,5-(OCH₃)₂-C₆H₃- | —NH—CH₂CH₂ | 196–198 |

TABLE 1-continued

Compounds:

$$\text{NC-C(=N-)-C(A)=... / NC-C(=N-)-C(B)=...}$$
(pyrazine with NC, NC substituents and A, B substituents)

| Compound No. | A | B | $n_D^{25}$ or m.p. (°C.) |
|---|---|---|---|
| 253 | 3,5-dimethoxyphenyl (OCH₃, OCH₃) | —NH—CH₂CH₂CH₃ | 133–135 |
| 254 | 3,4-dichlorophenyl (Cl, Cl) | —NH—CH₃ | 226–228 |
| 255 | 3,4-dichlorophenyl (Cl, Cl) | —NH—CH₂CH₃ | 208–210 |
| 256 | 3,4-dichlorophenyl (Cl, Cl) | —NHCH₂CH=CH₂ | 154.5–156 |
| 257 | 3,4-dichlorophenyl (Cl, Cl) | —NH—CH₂CH₂OH | 162–164 |
| 258 | 3,4-dichlorophenyl (Cl, Cl) | —NH—CH(COOH)—CH₂CH₃ | 183–187 dec |
| 259 | 3,5-dichlorophenyl (Cl, Cl) | —NH—CH₂CH₃ | 176–182 |
| 260 | 3,5-dichlorophenyl (Cl, Cl) | —NH—CH₂CH₂CH₃ | 150–153 |
| 261 | —O—CH₃ | —Cl | 116–117 |
| 262 | —O—CH₂CH₃ | —Cl | 58–59 |
| 263 | —O—CH₂CH₂CH₃ | —Cl | 34–42 |
| 264 | —O—CH(CH₃)₂ | —Cl | 48.5–50 |
| 256 | —O—CH(CH₃)CH₂CH₃ | —Cl | 63–66.5 |

TABLE 1-continued

Compounds:

$$\text{NC-C(=N-)-C(A)=C(B)-N=C(-CN)}$$ (pyrazine with NC, NC substituents and A, B)

| Compound No. | A | B | $n_D^{25}$ or m.p. (°C.) |
|---|---|---|---|
| 266 | phenyl | —Cl | 115–118 |
| 267 | 3-methylphenoxy (—O—C₆H₄—CH₃, meta) | —Cl | 114–121 |
| 268 | 2-chlorophenoxy (—O—C₆H₄—Cl, ortho) | —Cl | 101.5–104.5 |
| 269 | 4-chlorophenoxy (—O—C₆H₄—Cl, para) | —Cl | 105.0–109.5 |
| 270 | 4-chloro-3-methylphenoxy | —Cl | 128–132.5 |
| 271 | —S—CH₃ | —Cl | 86–90 |
| 272 | —S—CH₂CH₃ | —Cl | 55–58.5 |
| 273 | —S—CH₂CH₂CH₃ | —Cl | 35–38 |
| 274 | —S—CH(CH₃)₂ | —Cl | 38–45 |
| 275 | —S—CH₂COOCH₂CH₃ | —Cl | $n_D^{25} = 1.5842$ |
| 276 | —S—C₆H₅ | —Cl | 136–138.5 |
| 277 | phenoxy (—O—C₆H₅) | —NH—CH₂CH₃ | 197–198 |
| 278 | 3-methylphenoxy | —NH—CH₂CH₃ | 192–193 |
| 279 | 3,4-dichlorophenoxy | —NH—CH₂CH₃ | 102–103 |
| 280 | phenoxy (—O—C₆H₅) | —NH—CH₂CH₂CH₃ | 218–219 |

TABLE 1-continued

Compounds:

$$\begin{array}{c} NC-C(=N-)-C(A)=N \\ NC-C(=N-)-C(B)=N \end{array}$$ (2,3-dicyanopyrazine with A and B substituents)

| Compound No. | A | B | $n_D^{25}$ or m.p. (°C.) |
|---|---|---|---|
| 281 | 2-Cl-phenyl-O— | —NH—CH₂CH₂CH₃ | 127–128 |
| 282 | —S—CH₃ | —NH—CH₂ | 254–257 |
| 283 | —S—CH₃ | —NH—CH₂CH₂CH₃ | 198–202 |
| 284 | —S—CH₂CH₃ | —NH—CH₂CH₂CH₃ | 165–169 |
| 285 | —S—phenyl | —NH—CH₂CH₂CH₃ | 201–204.5 |
| 286 | —S—CH₂—phenyl | —NH—CH₂CH₂CH₃ | 153–155.5 |
| 287 | —O—phenyl | —O—phenyl | 184'185.5 |
| 288 | —O—(2-CH₃-phenyl) | —O—(2-CH₃-phenyl) | 158–160 |
| 289 | —O—CH₃ | —O—CH(CH₃)—COOCH₂CH₃ | 179–180 |
| 290 | —S—CH₃ | —S—CH₃ | 139–142.5 |
| 291 | —S—CH₂CH₃ | —S—CH₂CH₃ | 125–126.5 |
| 292 | —S—CH₂CH₂CH₃ | —S—CH₂CH₂CH₃ | 80–82.5 |
| 293 | —S—(4-Cl-phenyl) | —S—(4-Cl-phenyl) | 248–250.5 |

The novel 2,3-dicyanopyrazine derivatives of formula (I) provided by the present invention have the ability to inhibit the germination of the seeds of weeds and/or to wither their stems and leaves, the therefore exhibit an outstanding herbicidal effect as an active ingredient of pre-emergence herbicides and/or post-emergence herbicides in submerged soil treatment, foliar treatment in the growth stage of weeds, upland soil treatment, etc. In particular, the active compounds of formula (I) of this invention have excellent herbicidal activities in submerged lowland fields or paddies containing an abundance of water, and can be used advantageously as an active ingredient of herbicides for application to paddies. The superior activity of the compounds of formula (I) of this invention is believed to be ascribable to the mechanism whereby the compounds dissolve in water and are readily absorbed by weeds from their seeds, roots or submerged foliage, thus acting directly on the inhibition of their germination, the inhibition of their growth, their withering, etc.

The active compounds of formula (I) of this invention have selective herbicidal activities, and can effectively control only noxious weeds without substantial effects on useful agricultural and horticultural produces such as rice, barley, wheat and vegetables. For example, by treatment of submerged soil in paddies, the active compounds of this invention can selectively kill Echinochloa oryzicola, typical weed of the Gramineous family, without any substantial damage to rice which is also a plant of the Gramineous family.

Thus, according to another aspect of this invention, there is provided a herbicide containing a herbicidally effective amount of the novel 2,3-dicyanopyrazine derivative of formula (I).

During the course of a study of this herbicide, the present inventors found that (i) 2,3-dicyanopyrazine of the formula

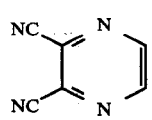 (VIII-1)

(ii) 2,3-dicyano-5-halo-6-substituted aminopyrazines of the formula

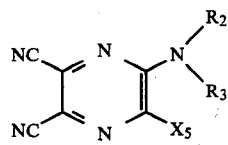 (VIII-2)

wherein $X_5$ represents a halogen atom, and $R_2$ and $R_3$ are as defined hereinabove, and (iii) 2,3-dicyanoquinoxaline derivative of the formula

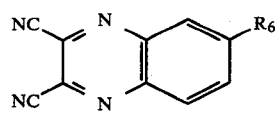 (VIII-3)

wherein $R_6$ represents a hydrogen atom, a halogen atom or a methyl group, which are either known or can be synthesized by methods similar to those used in preparing the known compounds, also exhibit herbicidal activities as do the 2,3-dicyanopyrazine derivatives of formula (I) of this invention.

Typical examples of the compounds of formulae (VIII-1), (VIII-2) and (VIII-3) are shown in Table 2.

TABLE 2

Compounds of the formula

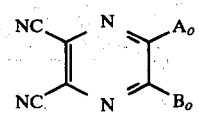

| Compound No. | $A_o$ | $B_o$ | m.p. (°C.) |
|---|---|---|---|
| 294 | —H | —H | 132 |
| 295 | —NH—CH$_2$CH$_3$ | —Cl | 146–147 |
| 296 | —NH—CH$_2$CH$_2$CH$_3$ | —Cl | 126–127 |
| 297 | —N(CH$_3$)$_2$ | —Cl | 47–48 |
| 298 | piperidino | —Cl | 82–83 |
| 299 | —NH—C$_6$H$_5$ | —Cl | 175–176 |
| 300 | —NH—CH$_2$—C$_6$H$_5$ | —Cl | 130–131.5 |
| 301 | —CH=CH—CH=CH— | | 218–220 |
| 302 | —CH=C(CH$_3$)—CH=CH— | | 116 |
| 303 | —CH=C(Cl)—CH=CH— | | 180–181 |

According to still another aspect, therefore, the invention provides a herbicide comprising as an active ingredient a herbicidally effective amount of a 2,3-dicyanopyrazine derivative of the general formula

 (VIII)

wherein
(i) $A_o$ and $B_o$ each have the same meanings as A and B defined hereinabove; or
(ii) $A_o$ represents a hydrogen atom and $B_o$ represents a hydrogen atom; or
(iii) $A_o$ represents a halogen atom and $B_o$ represents a group of the formula

 ;

or
(iv) $A_o$ and $B_o$ together represent a group of the formula

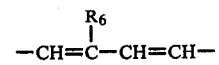

in which $R_6$ represents a hydrogen or halogen atom or a methyl group.

Various weeds can be controlled by the herbicides of this invention, and typical examples are listed below. These examples are merely illustrative, and it should be understood that the herbicides of this invention exhibit equally superior herbicidal effects on other weeds.

WEEDS IN PADDIES

Compositae (*Bidens tripartita*, etc.);
Scrophulariaceae (*Dopatrium junceum, Vandellia angustifolia, Deicnostema violaceum, Lindernia procumbens*, etc.);
Lythraceae (*Ammannia multiflora. Rotala indica. Lythrum anceps*, etc.);
Elatinaceae (*Elatine triandra*, etc.);
Callitrichaceae (*Callitriche verna*, etc.);
Onagraceae (*Ludwigia prostrata*, etc.);
Polygonaceae (*Polygonum hydropiper*, etc.);

Pontederiaceae (*Monochoria vaginalis*, etc.);
Eriocaulaceae (*Eriocaulon sieboldtianum, Eriocaulon miquelianum*, etc.);
Lemnaceae (*Spirodela polyrhiza. Lemna paucicostate, Lemna trisulca*, etc.);
Cyperaceae (*Cyperus difformis, Eleocharis acicularis, Fimbristylis miliaceae, Cyperus serotinus, Scirpus juncoides*, etc.);
Gramineae (*Echinochloa oryzicola, Hymenachne indica*, etc.);
Hydrocharitaceae (*Blyxa ceratosperma, Ottelia alismoides*, etc.);
Alismataceae (*Alisma canaliculatum, Sagittaria trifolia, Sagittaria pygmaea, Sagittaria aginashi*, etc.);
Marsileaceae (*Marsilea quadrifolia*, etc.); and
Zygnemataceae (*Spirogyra arcla*, etc.); etc.

WEEDS IN UPLAND FARMS

Compositae (*Erigeron annuus, Erigeron philadelphicus, Galinsoga ciliata, Erigeron canadensis, Taraxacum officinale*, etc.);
Rubiaceae (*Galium aparine*, etc.);
Scrophulariaceae (*Veronica didyma*, etc.);
Solanaceae (*Solanum nigrum*, etc.);
Convolvulaceae (*Calystegia hederacea*, etc.);
Euphorbiaceae (*Euphorbia supina*, etc.);
Oxalidaceae (*Oxalis corniculate, Oxalis martiana*, etc.);
Cruciferae (*Capsella bursa-pastoris, Raphanus raphanistrum, Brassica nigra*, etc.);
Caryophyllaceae (*Stellaria alsine, Cerastium holosteoides, Stellaria media*, etc.);
Amaranthaceae (*Amaranthus viridis, Amaranthus lividus*, etc.);
Chenopodiaceae (*Chenopodium album, Chenopodium ficifolium*, etc.);
Polygonaceae (*Polygonum persicaria, Rumex japonicus*, etc.);
Cyperaceae (*Cyperus rotundus, Cyperus iria*, etc.); and
Gramineae (*Alopercurus aequalis, Digitaria adscendens, Poa annua, Eleusine indica, Echinochloa crus-galli*, etc.).

Many of the herbicidal compounds of this invention exhibit outstanding herbicidal activities on paddy weeds in submerged soil treatment. These compounds are generally non-phytotoxic to transplanted rices, and can effectively control weeds in paddies such as those described hereinabove (see Table 4 below). For example, among the active compounds listed in Table 1, those having the strongest activities are compounds Nos. 130, 143, 176, 177, 192, 213, 214, 218, 222, 223, 229, 230, 235, 236, 237, 241 and 242. Those having the second strongest activities are compounds Nos. 1, 6, 11, 12, 14, 15, 16, 21, 22, 23, 26, 46, 47, 50, 53, 54, 56, 57, 58, 64, 66, 68, 72, 94, 95, 97, 127, 129, 130, 132, 139, 142, 144, 152, 165, 166, 178, 184, 189, 191, 193, 198, 204, 217, 224, 225, 226, 231, 233, 234, 254, 258, 262, 263, 264, 265, and 277.

Thus, the present invention provides a number of active compounds which can control a broad range of weeds in paddies without substantial phytotoxicity to transplanted rice.

Many of the herbicidal compositions of this invention exhibit unique herbicidal activities. For example, those containing compounds of formula (I-d), especially those of the following formula

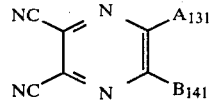

(I-d-1)

wherein $A_{131}$ has the same meaning as $A_{13}$; and $B_{141}$ represents an ethylamino, n-propylamino, n- or iso-butylamino, 1-carboxyethylamino, 1-carboxy-n-propylamino, 1-carboxy-iso-butylamino, 1-carboxy-n-pentylamino, or allylamino group, for example, compounds Nos. 176, 177, 178, 189, 191, 192, 193, 194, 213, 214, 217, 218, 222, 223, 224, 225, 229, 230, 231, 233, 234, 235, 236, 237, 238, 239, 241, 242, 243, 244, 245, 248, 255, 256, 258, 259, and 260 shown in Table 1, have the property of selectively blanching and withering (causing chlorosis; i.e. inhibiting the formation of chlorophy and/or the acceleration of its decomposition) weeds without chlorosis of useful crops. Hence, they are most suitable as highly selective herbicides of the chlorosis type. Moreover, many of the herbicides containing the compounds of formula (I-d-1) not only have superior chlorotic and selective herbicidal activities, but also exhibit a high level of selective chlorotic activities both in paddies and upland farms even when applied at low dosage rates per unit area, and also selectively blanch and wither paddy and upland weeds selectively without chlorosis of important crops both by soil and foliar application. This surprisingly unique physiological activity is shown, for example, by the fact that herbicides containing compounds Nos. 176, 177, 192, 213, 214, 218, 222, 223, 229, 230, 235, 236, 237, 241 and 242 which are most suitable compounds of formula (I-d-1) can blanch and wither almost all annual and perennial paddy weeds such as *Echinochloa oryzicola, Scirpus juncoides, Monochoria vaginalis, Rotala indica, Lindernia procumbens, Elatine triandra, Sagittaria pygmaea, Cyperus serotinus, Sagittaria trifolia, Sagittaria aginashi, Cyperus difformis,* and *Spirodela polyrhiza* in submerged paddies at a time ranging from the germination of the weeds to their 2–3 leaf stage (within about 15 days after transplantation of rice plants). On the other hand, the rice plants as seedlings in the 2–3 leaf stage which are planted to a depth of 0.5 to 1 cm or more are not at all affected by the chlorotic activities of the herbicides of this invention. It is especially noteworthy that even when the dosage of these herbicides is five times as large as that required to cause chlorosis and withering of the weeds, these herbicides do not at all cause chlorosis to rice plants.

When small amounts of conventional paddy herbicides are used together with the herbicides of the invention, all weeds can be eradicated completely by using even lower dosages of the active ingredients of the herbicides of the invention. Furthermore, the herbicides of this invention are non-phytotoxic to rice plants whether they are suspended in water and sprayed all over a submerged paddy after transplantation or applied as granules or the like to a submerged paddy. Among the paddy weeds, broad-leaved annual weeds and Lemnaceae are especially sensitive to the herbicidal agents of this invention, and can be controlled by applying very low dosages of the herbicidal agents (for example, in the case of compound No. 177, 25 to 50 g/10 ares or less). *Echinochloa oryzicola* both in the initial and intermediate growth stages can be completely blanched and withered by applying compound No. 177 at a dosage of 50 to 100 g/10 ares or less. Furthermore, compound No.

177 in a dosage of 100 to 200 g/10 ares can blanch and wither perennial *Sagittaria pygmaea* and *Cyperus serotinus*.

When important upland crops are cultivated in farms and the herbicides of this invention are sprayed at a time of the simultaneous occurring of weeds so that they may deposit on the entire surfaces of crops and the weeds, annual gramineous weeds and broad-leaved weeds, such as *Digitaria adscendens, Eleusine indica, Amaranthus viridis, Chenopodium ficifolium, Galinsoga ciliata, Polygonum persicaria, Alopecurus aequalis,* and *Amaranthus lividus* can be completely blanched and withered. The dosage of the herbicide of this invention required for complete herbicidal control is about 50 to 100 g/10 ares for compound No. 177. For example, compound No. 177 shows surprising selective chlorotic activities in that it is non-phytotoxic to carrot in a dosage of up to 1000 g/10 ares, to sunflower, cotton, rice, corn and sugar cane in a dosage of up to 500 g/10 ares, and to peanut, wheat, soybean and radish in a dosage of up to 250 g/10 ares.

In overall foliar treatment, the herbicides of the invention exhibit more outstanding effects at lower dosages when applied at a time between emergence and a 2.5-leafe stage. When sprayed on the entire surfaces of a land covered with lawn grass (Manilagrass, Japanese lawngrass), compound No. 177 in a dose of 100 g/10 ares causes the chlorosis and withering of most annual weeds, but it is non-phytotoxic to Manilagrass and Japanese lawngrass even when applied in a dose of 1600 g/10 ares.

Selective chlorosis was examined by seeding crops, covering them with soil to a height of about 2 to 3 cm, and applying a herbicide containing the compound of formula (I-d-1) of the invention to the soil surface. Almost all weeds showed chlorosis and withering when the dosage was 50 g/10 ares and more, and were almost completely blanched and withered in a dose of 100 g/10 ares.

Important upland weeds include *Digitaria adscendens, Polygonum persicaria, Galinsoga ciliata, Amaranthus viridis, Chenopodium album, Chenopodium ficifolium, Echinochloa crus-galli,* and *Alopecurus aequalis*. On the other hand, upland crops which remain sound without chlorosis include carrot, sunflower, cotton, peanut, soybean, corn, rice, and radish. Some of them do not undergo a chlorotic activity even when the dosage is 16 times (for example, 1600 g/10 ares for compound No. 177) as large as that required for chlorosis and withering of weeds. Furthermore, the herbicides of this invention form a firm treated layer not seen with any conventional herbicides within 0.5 cm of the surface of the soil in upland farms, and for example, when compound No. 177 is applied at a rate of 100 g/10 ares, it gradually decomposes in the treated layer and shows a residual activity for 20 to 30 days.

The herbicides of this invention are also effective against a very broad range of other upland weeds including *Galium aparin, Rumex japonicus, Erigeron philadelphicus, Erigeron annuus,* and *Capsella bursapastoria*. It has also been found surprisingly that these herbicides show outstanding herbicidal effects in controlling perennial weeds such as *Cyperus rotundus* and *Oxalis martiana* which are extremely difficult to eradicate.

When a herbicide containing a compound of formula (I-d-1), for example compound No. 177, is applied in a dose of 100 to 200 g/10 ares and then uniformly mixed with the soil in a surface layer with a depth of 5 cm, most annual and perennial weeds, after germination, will be blanched and withered. When various crops are sown about 20 days after the eradication of the weeds, those crops which are inherently sensitive to the herbicide do not suffer from phytotoxicity. This suggests the applicability of the herbicides of this invention as controlling agents for perennial weeds.

Some of the herbicides of this invention exhibit an activity of causing an antiauxin-like symptom. Examples of active compounds having such an activity are compounds Nos. 119, 181, 190, 191, 196, 199, 207, 266, 268, 276, 291, 292 and 293 shown in Table 1.

Furthermore, some of the herbicides of this invention exhibit a high activity of inhibiting germination of weeds. For example, herbicides containing compounds of the following formula

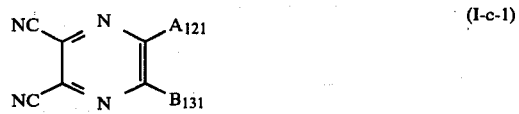

(I-c-1)

wherein $A_{121}$ has the same meaning as $A_{12}$ and $B_{131}$ represents an allyloxy or 2-propynyloxy group, for example compounds Nos. 91, 129, 130, 142, and 143 shown in Table 1, have such an activity.

As stated hereinabove, the herbicides of this invention are very effective as herbicides for treating submerged soil in rice cultivation.

The herbicides of this invention generally exhibit high herbicidal activities as a foliar treating agent during the growth of weeds (see Table 5 below). Many of the herbicides of this invention are generally non-selective for weeds. Some of them have foliar contact selectivity for important crops such as rice and wheat, and control not only weeds of the gramineous family and other general broad-leaved weeds without phytotoxicity to the genus Oryza and genus Triticum of the gramineous family. This noteworthy specific selectivity is shown, for example, by compound No. 22 shown in Table 1 which is safe on the genus Oryza and has a marked herbicidal effect on weeds of the gramineous family other than the genus Oryza such as wheat and many broad-leaved weeds. Known herbicides having such a high degree of contact selectivity are Propanil in rice cultivation, and Atrazine in corn cultivation. Propanil loses its selectivity by reaction with carbamate-type insecticides or organo-phosphorus insecticides and thus causes phytotoxicity, whereas compound No. 22 does not have such reactivity. Examples of active compounds which show superior herbicidal activities in foliar treatment include compounds Nos. 1, 2, 3, 4, 5, 8, 10, 20, 21, 22, 23, 24, 26, 130, 143, 176, 177, 213, 214, 222, 223, 225, 229, 262 and 263.

The herbicides of this invention exhibit herbicidal activities in treatment of upland soil with a relatively low moisture content. For example, compounds Nos. 176, 177, 191, 213 and 214 show superior herbicidal activities in upland farms. They have outstanding effects against *Digitari adscendens* and *Echimochloa crus-galli* which are typical gramineous weeds in upland farms and *Amoranthus viridis* without phytotoxicity to wheat, rice, corn, soybean, etc. (see Table 6). Compounds Nos. 176, 177, 191, 213, 214, 222, 230 and 237 are absorbed by the surface layer of upland soil, and cause non-selective chlorosis to almost all upland weeds occurring there and wither them. However, they are non-phytotoxic to useful crops sown below the surface layer containing these active compounds absorbed therein.

The active compounds of formula (VIII) can be applied to a growth medium or to plants to be treated either alone or, as is generally done, as herbicidal compositions comprising a herbicidally effective amount of one or more compound of formula (VIII) and an agronomically acceptable carrier. By the agronomically acceptable carrier is meant any substance which can be used to dissolve, disperse, or diffuse a herbicidal compound in the compositions without impairing its herbicidal effect and which by itself has no detrimental effect on the soil, equipment, crops, or agronomic environment. The herbicidal compositions of this invention can be solid or liquid formulations or solutions. For example, the compound of formula (VIII) can be formulated as wettable powders, emulsifiable concentrates, dusts, granular formulations, aerosols, or flowable emulsifiable concentrates. In these formulations, the compounds are extended with a liquid or solid carrier, and if desired, suitable surfactants are incorporated.

Examples of solid carriers which are useful in the practice of this invention include vegetable powders (e.g., starch, acacia, etc.), mineral powders, clay minerals (e.g., kaolinite group, montmorillonite group, etc.), talc, pyrophylite, vermiculite, calcite, gypsum, silica gel, mica group, dolomite, magnesite, kieselguhr, slaked lime, pumice, sulfur, inorganic salts (e.g., calcium carbonate), and synthetic polymers (e.g., phenolic resin or urea resin). Examples of liquid carriers or solvents which are useful in the practice of this invention include water, aliphatic and alicyclic hydrocarbons (e.g., n-hexane, cyclohexane, petroleum ether, solvent naphtha, kerosene, or light oil), aromatic hydrocarbons (e.g., benzene, toluene, xylene, methylnaphthalene, or aromatic naphtha), alcohols (e.g., methanol, ethanol, propanol, or ethylene glycol), halogenated hydrocarbons (e.g., methylene chloride, trichloroethylene, tetrafluoroethane, or chlorobenzene), ethers (e.g., ethyl ether, tetrahydrofuran, dioxane, or ethyl cellosolve), ketones (e.g., acetone, methyl ethyl ketone, methyl isobutyl ketone, cyclohexanone, or isophorone), esters (e.g., ethyl acetate, or butyl acetate), amides (e.g., N,N-dimethylformamide, or N,N-dimethylacetamide), and sulfoxides (e.g., dimethyl sulfoxide).

Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product.

The herbicide of this invention, although depending upon its form, can generally contain at least 0.5% by weight, preferably 1 to 99% by weight, more preferably 2 to 80% by weight, of the active compound of formula (VIII) based on the weight of the herbicide.

The herbicides of this invention are formulated into any desired forms such as dusts, granules, wettable powders, solutions, emulsifiable concentrates, and aerosols according to the method of application. Formulation of these herbicidal compositions can be effected by procedures known per se in the art. For example, dusts, granules and wettable powders can be formulated by mixing and pulverizing at least one active compound of formula (VIII) and at least one solid carrier or diluent described above, adding a suitable amount of a surface-active agent, and mixing them uniformly. Solutions or emulsifiable concentrates can be formulated by dissolving or dispersing at least one active compound of formula (VIII) in at least one of the liquid carriers or diluents, and if desired, adding a surface-active agent.

The dusts and granules can contain the active compound in a concentration of 2 to 30% by weight based on the weight of the herbicide, and the wettable powders, solutions and emulsifiable concentrates may contain 5 to 60% by weight of the active compound.

The herbicides of this invention may also contain fungicides, bactericides, insecticides, acaricides, nematocides, fertilizers, plant growth regulating agents, and other herbicides which are usually employed in the field of agriculture.

Compounds shown in Table 3 below can be especially advantageously used as the other herbicides whose herbicidal effect can be synergistically increased by using a combination of the active compounds of this invention, although differing according to the types of weeds to be controlled, and the method of application. It should be noted that there are other herbicides which can exhibit synergistic effects when used together with the herbicides of this invention. In particular, herbicides of the type which disturb the chlorophyl-forming mechanism of weeds and cause their chlorosis and withering, for example herbicides containing the compounds of formula (I-d-1) shown hereinabove also affect amino acids, proteins, fats, and carbohydrates which constitute plant bodies and nucleic acid or hormones which play an important role within the body. By using a combination of a small amount of the herbicide of this invention and another herbicide, its herbicidal effect increases tremendously.

TABLE 3

| Trivial name (tradename) | Chemical nomenclature |
|---|---|
| trifluralin | α,α,α-trifluoro-2,6-dinitro-N,N—di-n-propyl-p-toluidine |
| amiben | 2,5-dichloro-3-aminobenzoic acid |
| alachlor (Lasso) | N—methoxymethyl-2,6-diethyl-α-chloroacetoanilide |
| dichlobenil (Casoron) | 2,6-dichlorobenzonitrile |
| chloropropham (CIPC) | isopropyl-N—(3-chlorophenyl) carbamate |
| diuron (DCMU) | 3-(3,4-dichlorophenyl)-1,1-dimethylurea |
| linuron (Afalon) | 3-(3,4-dichlorophenyl)-1-methoxy-1-methyl urea |
| chloronitrofen (CNP) | 2,4,6-trichlorophenyl-4'-nitrophenyl ether |
| simazine (CAT) | 2-chloro-4,6-bis(ethylamino)-s-triazine |
| atrazine (Gesaprim) | 2-chloro-4-ethylamino-6-isopropylamino-s-triazine |
| DNBP | 2-sec-butyl-4,6-dinitrophenol |
| simetryne | 2-methylthio-4,6-bis(ethylamino)-s-triazine |
| MT-101 | α-(β-naphthoxy)-n-propionanilide |
| SK-223 | 1-(α,α-dimethylbenzyl)-3-(4-methylphenyl)urea |
| oxadiazon (Ronstar) | S-(4-chlorobenzyl)-N,N—diethylthiol carbamate |
| benthiocarb (Saturn) | 3-(2,4-dichloro-5-isopropoxyphenyl)-5-tert-butyl-1,3,4-oxadiazole-2(3H)-one |
| butachlor (Machete) | 2-chloro-2',6'-diethyl-N—(n-butoxymethyl)acetanilide |
| molinate (Ordram) | S-ethyl-hexahydro-1H—azepine-1-carbothioate |
| MCP | 2-methyl-4-(chlorophenoxy)acetic acid |
| swep | methyl-N—(3,4-dichlorophenyl) carbamate |

TABLE 3-continued

| Trivial name (tradename) | Chemical nomenclature |
|---|---|
| bentazon (Basagran) | 3-isopropyl-1H—2,1,3-benzothia-diazine-(4)-3H—one-2,2-dioxide |
| propanil (Stam) | 3,4-dichloro-n-propionanilide |
| MCPB | γ-(2-methyl-4-chlorophenoxy)-n-butyric acid |

Thus, according to still another aspect, the present invention provides a herbicidal composition comprising at least one 2,3-dicyanopyrazine derivative of formula (VIII) and at least one other herbicidal compound shown in the above Table.

This herbicidal composition has a strong synergetic effect. For example, in the treatment of upland soil habitated by *Digitaria adscendens, Chenopodium ficifolium* and *Amaranthus viridis*, compound No. 177 showed a control rating of 50% in a dosage of 25 g/10 ares and a control rating of 80 to 90% in a dosage of 50 g/10 ares, and compound No. 176 showed a control rating of 60 to 70% in a dosage of 100 g/10 ares and a control rating of 80% in a dosage of 200 g/10 ares. The activities of compounds Nos. 176 and 177 strinkingly increase when they are used together with other herbicides shown in the above table as synergists in such low dosages which by themselves are not enough to exhibit feasible herbicidal effects. Furthermore, even when general herbicides are used in low dosages not enough to exhibit substantial herbicidal effects, the joint use of as small as 25 g/10 ares of compound No. 177 makes it possible for these herbicides to exhibit their marked herbicidal activities. Examples of especially effective synergists are trifluralin, amiben, alachlor, chloropropham, linuron, DCMU, CAT, and atrazine. Of these, trifluralin, alachlor, CAT and atrazine show superior synergistic effects.

In soil treatment at the time of germination in water, the synergistic effect of the herbicides of this invention and the synergists shown in the above table is remarkable. For example, compound No. 177 tends to have a lower herbicidal effect on *Echinochloa oryzicola* than on broad-leaved weeds, *Scirpus juncoides* and *Eleocharis acicularis*, but by jointly using a low dosage of simetryne, oxadiazon, benthiocarb, CNP, butachlor, MCP, etc. together with this compound, its herbicidal effect on *Echinochloa oryzicola*, broad-leaved weeds, *Scirpus juncoides*, and *Eleocharis acicularis* increases markedly. Furthermore, by using benthiocarb, and butachlor, whose activities on broad-leaved weeds are inferior, or CNP whose activity on broad-leaved weeds and *Eleocharis acicularis* is inferior in combination with compound No. 177, the defects of these herbicides can be remedied to cause them to exhibit superior herbicidal effects, although this depends upon the conditions for application. Other effective herbicides which show synergistic effects are, for example, MT101, SK223 and molinate.

The effect of synergists on the herbicides of this invention in submerged soil treatment in the growth period shows the same tendency as that in emergence treatment, and the aforesaid synergists can be synergistically used. MCP, propanil, and bentazon are also effective.

When the herbicide of this invention is used together with other herbicides, the herbicidal activity can be strikingly increased by adding a small amount of the herbicide of the invention because the herbicidal mechanism of the herbicides of this invention differs from those of conventional other herbicides. The amount of the other herbicide is not critical, and can be varied widely according to the type of the herbicide of the invention, the type of weeds, the place of application, and the conditions for application. Generally, the active ingredient of formula (VIII) is incorporated in an amount of 0.5 to 99.5%, preferably 2 to 98%, more preferably 5 to 95% to the total amount of active ingredients.

As stated hereinabove, the herbicides of this invention can be applied directly to the soil as a preemergence and/or post-emergence herbicides in submerged paddies and upland farms, or directly sprayed to weeds by foliar treatment.

Thus, according to this invention, there is also provided a method for controlling weeds in an agricultural crop which comprises applying a herbicidally effective amount of a 2,3-dicyanopyrazine derivative of formula (VIII) to the locus to be protected from the weeds.

The amount of the active compound of formula (VIII) is not critical, and can be varied over a wide range according to the type of the active compound, the time of application, the method of application, etc. It is generally advantageous to use this active compound in an amount of at least 10 g, preferably 20 to 1000 g, more preferably 50 to 600 g, per 10 ares. The above rates of application are tentative standards, and can of course be increased or decreased according to the condition of the crop, the state of habitation of weeds, etc.

The herbicidal composition can be applied by any desired conventional method. For example, it is sprayed terrestrially or aerially to the locus to be protected from weeds before or after the seeding or transplantation; or it may be sprayed together with seeds at the time of seeding. Alternatively, the germination of seeds of weeds mixed with seeds of crops can be inhibited by dipping the crop seeds in an aqueous solution containing the active compound of the invention before seeding.

The active compounds of formula (VIII) have little or no phytotoxicity to useful agricultural crops and show low mammalian toxicity, and therefore are very suitable as herbicides.

The following Formulation and Test Examples further illustrate the formulation of the herbicides provided by the present invention, and their herbicidal activities.

In these examples, all parts and percentages are by weight. The numbers of the compounds refer to those given in Tables 1 and 2.

FORMULATION EXAMPLE 1 (WETTABLE POWDER)

Forty parts of the active compound of the invention, 55 parts of a 2:1 mixture of ZEEKLITE (a tradename for kaolinite made by Zeeklite Chemical & Mining Co., Ltd.) and KUNILITE (a tradename for kieselguhr made by Kunimine Industries Co., Ltd.) as a carrier and 5 parts of SORPOL 800A (a tradename for a composition containing polyoxyethylene alkylaryl ether polymer, polyoxyethylene sorbitan alkylate, polyoxyethylene fatty acid derivative and alkylaryl sulfonate made by Toho Chemical Industries Co., Ltd.) as a surface active agent were mixed and pulverized to form a 40% wettable powder.

FORMULATION EXAMPLE 2 (EMULSIFIABLE CONCENTRATES)

Fifteen parts of the active compound of the invention, 80 parts of tetrahydrofuran and 5 parts of SORPOL 800 A (tradename) were mixed to form a 15% emulsifiable concentrate.

FORMULATION EXAMPLE 3 (GRANULES)

Ten parts of the active compound of the invention, 50 parts of bentonite, 35 parts of KUNILITE and 5 parts of sodium ligninsulfonate were mixed and pulverized. Ten parts of water was added, and the mixture was stirred uniformly. The mixture was extruded from holes with a diameter of 0.7 mm, dried, and cut to suitable lengths to form 10% granules.

The following examples show the results of testing the herbicidal agents of this invention on plants, thus demonstrating their effects and the methods of their use.

TEST EXAMPLE 1 (SUBMERGED SOIL TREATMENT)

Polyethylene pots (1/5,000 ares) were each filled with paddy soil (clayloam), and seeds of *Echinocholoa oryzicola*, broad-leaved weeds (*Monochoria vaginalis, Rotala indica, Lindernia procumbens*), and *Scirpus juncoides* were sown at a depth of 2 cm from the soil surface, and two seedlings of *Eleocharis acicularis* were transplanted. At the same time, seedlings of rice in the 3-leaf stage, in groups each consisting of two seedlings, were transplanted, to a depth of 2 cm, and submerged to a level of 3 cm above the soil surface.

A wettable powder containing each of the active compounds of the invention shown in Table 4 was weighed, diluted with 10 ml per pot of water, and applied to the water surface by dripping. The rice plants were then grown in a glass chamber, and 3 weeks after the treatment, the herbicidal effects of the active compound and their influences on rice were examined. The results are shown in Table 4. The figures shown in the table indicate the degrees of rice injury and herbicidal activities rated as follows:

| Rating | Rice injury | Herbicidal activity |
|---|---|---|
| 5 | Withering | 100% control (remaining of weeds, 0%) |
| 4 | Great injury | 80% control (remaining of weeds, 20%) |
| 3 | Intermediate injury | 60% control (remaining of weeds, 40%) |
| 2 | Small injury | 40% control (remaining of weeds, 60%) |
| 1 | Slight injury | 20% control (remaining of weeds, 80%) |
| 0 | No injury | 0% control (remaining of weeds, 100%) |

TABLE 4

| Compound No. | Dosage (g/10a) | Injury to rice | Echinochloa oryzicola | Broad-leaved weeds | Scirpus juncoides | Eleocharis acicularis |
|---|---|---|---|---|---|---|
| 1 | 2000 | 0.5 | 5 | 5 | 5 | 5 |
|   | 1000 | 0 | 5 | 5 | 5 | 4 |
|   | 500 | 0 | 5 | 5 | 4 | 3 |
| 2 | 2000 | 0 | 2 | 5 | 0 | 0 |
| 3 | 2000 | 0 | 5 | 5 | 2 | 2 |
| 4 | 2000 | 0 | 5 | 5 | 0 | 4 |
|   | 1000 | 0 | 5 | 5 | 0 | 2 |
|   | 500 | 0 | 4 | 3 | 0 | 0 |
| 5 | 2000 | 0 | 5 | 5 | 5 | 4 |
|   | 1000 | 0 | 5 | 5 | 4 | 2 |
|   | 500 | 0 | 3 | 3 | 2 | 0 |
| 6 | 2000 | 0 | 5 | 5 | 5 | 4 |
|   | 1000 | 0 | 5 | 5 | 5 | 2 |
|   | 500 | 0 | 5 | 4 | 4.5 | 1 |
| 7 | 2000 | 0 | 5 | 5 | 1 | 4 |
|   | 1000 | 0 | 5 | 5 | 0 | 2 |
|   | 500 | 0 | 4 | 3 | 0 | 0 |
| 8 | 2000 | 0 | 5 | 5 | 5 | 2 |
|   | 1000 | 0 | 5 | 5 | 5 | 1 |
|   | 500 | 0 | 5 | 2 | 2 | 0 |
| 9 | 2000 | 0 | 5 | 5 | 5 | 4 |
|   | 1000 | 0 | 5 | 5 | 4 | 3 |
|   | 500 | 0 | 5 | 4 | 2 | 2 |
| 10 | 2000 | 0 | 5 | 5 | 5 | 4 |
|    | 1000 | 0 | 5 | 4.5 | 5 | 2 |
|    | 500 | 0 | 4 | 2 | 5 | 0 |
| 11 | 2000 | 0 | 5 | 5 | 4.5 | 2 |
|    | 1000 | 0 | 5 | 5 | 4 | 2 |
|    | 500 | 0 | 5 | 5 | 2 | 1 |
|    | 250 | 0 | 5 | 4.5 | 0 | 1 |
| 12 | 2000 | 0 | 4.5 | 4.5 | 4 | 2.5 |
|    | 1000 | 0 | 4.5 | 4.5 | 4 | 2 |
|    | 500 | 0 | 4.5 | 4.5 | 4 | 2 |
|    | 250 | 0 | 4.5 | 4.5 | 3 | 1 |
| 13 | 2000 | 0 | 4.5 | 5 | 5 | 2 |
|    | 1000 | 0 | 4 | 5 | 4 | 1 |
| 14 | 2000 | 0 | 5 | 5 | 4.5 | 2 |
|    | 1000 | 0 | 5 | 5 | 4 | 1 |
|    | 500 | 0 | 5 | 5 | 3 | 0 |
| 15 | 2000 | 0 | 4.5 | 4.5 | 5 | 2 |
|    | 1000 | 0 | 4.5 | 4.5 | 4 | 1 |
|    | 500 | 0 | 4.5 | 4.5 | 4 | 0 |
| 16 | 2000 | 0 | 5 | 5 | 5 | 1 |
|    | 1000 | 0 | 5 | 5 | 5 | 0 |
|    | 500 | 0 | 5 | 5 | 5 | 0 |
| 17 | 2000 | 0 | 5 | 5 | 5 | 1 |
|    | 1000 | 0 | 4.5 | 5 | 4 | 0 |
|    | 500 | 0 | 4 | 5 | 2 | 0 |
| 18 | 2000 | 0 | 4.5 | 5 | 4.5 | 1 |
|    | 1000 | 0 | 4.5 | 5 | 3 | 0 |
|    | 500 | 0 | 4 | 4.5 | 0 | 0 |
| 19 | 2000 | 0 | 4.5 | 5 | 0 | 0 |
| 20 | 1000 | 1 | 5 | 5 | 5 | 1 |
|    | 500 | 0 | 4 | 5 | 3 | 0 |
| 21 | 1000 | 0 | 5 | 5 | 5 | 3 |
|    | 500 | 0 | 5 | 5 | 5 | 2 |
| 22 | 1000 | 4 | 5 | 5 | 5 | 4.5 |
|    | 500 | 2 | 5 | 5 | 5 | 3 |
|    | 250 | 0 | 4 | 5 | 4 | 0 |
| 23 | 1000 | 0 | 5 | 5 | 5 | 3 |
|    | 500 | 0 | 4 | 5 | 4 | 1 |
| 24 | 1000 | 0 | 4.5 | 5 | 3 | 3 |
|    | 500 | 0 | 4 | 3 | 2 | 2 |
| 25 | 1000 | 0 | 5 | 5 | 5 | 0 |
|    | 500 | 0 | 4 | 5 | 3 | 0 |
| 26 | 1000 | 0 | 5 | 5 | 4 | 0 |
|    | 500 | 0 | 4.5 | 5 | 2 | 0 |
|    | 250 | 0 | 4 | 4.5 | 0 | 0 |
| 27 | 2000 | 0 | 4 | 5 | 1 | 0 |
| 28 | 2000 | 0 | 5 | 5 | 2 | 0 |
|    | 1000 | 0 | 5 | 5 | 1 | 0 |
| 29 | 2000 | 0 | 5 | 5 | 5 | 0 |
|    | 1000 | 0 | 4 | 4 | 4 | 0 |
| 30 | 2000 | 0 | 5 | 5 | 4 | 0 |
|    | 1000 | 0 | 3 | 4 | 2 | 0 |
| 31 | 2000 | 3 | 4 | 5 | 4 | 0 |
|    | 1000 | 1 | 3.5 | 5 | 3 | 0 |
|    | 500 | 0 | 3 | 5 | 1 | 0 |
| 32 | 2000 | 0 | 5 | 5 | 4 | 0 |
|    | 1000 | 0 | 4.5 | 5 | 2 | 0 |
| 34 | 1000 | 0 | 5 | 5 | 1 | 0 |
|    | 500 | 0 | 4 | 4.5 | 1 | 0 |
| 35 | 2000 | 0 | 5 | 5 | 3 | 3 |
|    | 1000 | 0 | 5 | 5 | 2 | 1 |

TABLE 4-continued

| Compound No. | Dosage (g/10a) | Injury to rice | Herbicidal activity | | | |
|---|---|---|---|---|---|---|
| | | | Echinochloa oryzicola | Broad-leaved weeds | Scirpus juncoides | Eleocharis acicularis |
| 36 | 2000 | 0 | 4.5 | 5 | 3 | 0 |
| | 1000 | 0 | 3 | 5 | 1 | 0 |
| 37 | 2000 | 0 | 5 | 5 | 5 | 4 |
| | 1000 | 0 | 5 | 5 | 4.5 | 1 |
| 39 | 2000 | 0 | 5 | 5 | 5 | 2 |
| | 1000 | 0 | 5 | 5 | 5 | 0 |
| | 500 | 0 | 4.5 | 5 | 5 | 0 |
| 41 | 2000 | 0 | 4 | 5 | 4 | 0 |
| 42 | 2000 | 0 | 4 | 5 | 2 | 0 |
| | 1000 | 0 | 2 | 5 | 0 | 0 |
| 44 | 2000 | 0 | 3 | 2 | 0 | 0 |
| 45 | 2000 | 0 | 5 | 5 | 4 | 2 |
| | 1000 | 0 | 5 | 5 | 3 | 0 |
| | 500 | 0 | 2.5 | 2 | 1 | 0 |
| 46 | 2000 | 0 | 5 | 5 | 5 | 4 |
| | 1000 | 0 | 5 | 5 | 5 | 2 |
| | 500 | 0 | 5 | 5 | 5 | 0 |
| | 250 | 0 | 4.5 | 4 | 5 | 0 |
| 47 | 2000 | 0 | 5 | 5 | 5 | 3 |
| | 1000 | 0 | 5 | 5 | 4 | 2 |
| | 500 | 0 | 5 | 4.5 | 3 | 1 |
| | 250 | 0 | 5 | 3 | 1 | 0 |
| 48 | 2000 | 0 | 5 | 5 | 4 | 2 |
| | 1000 | 0 | 5 | 5 | 3 | 1 |
| | 500 | 0 | 5 | 4 | 1 | 0 |
| 49 | 2000 | 0 | 5 | 5 | 5 | 4 |
| | 1000 | 0 | 5 | 5 | 5 | 3 |
| | 500 | 0 | 5 | 4 | 4 | 1 |
| 50 | 2000 | 0 | 5 | 5 | 3 | 5 |
| | 1000 | 0 | 5 | 5 | 2 | 5 |
| | 500 | 0 | 5 | 5 | 1 | 3 |
| | 250 | 0 | 5 | 4 | 0 | 2 |
| 51 | 2000 | 0 | 5 | 5 | 5 | 4 |
| | 1000 | 0 | 5 | 5 | 4 | 3 |
| | 500 | 0 | 4 | 4 | 3 | 1 |
| 52 | 2000 | 0 | 5 | 5 | 5 | 4.5 |
| | 1000 | 0 | 5 | 5 | 5 | 4 |
| | 500 | 0 | 5 | 3 | 2 | 3 |
| | 250 | 0 | 5 | 2 | 0 | 0 |
| 53 | 2000 | 0 | 5 | 5 | 5 | 1 |
| | 1000 | 0 | 5 | 5 | 5 | 0 |
| | 500 | 0 | 5 | 5 | 5 | 0 |
| | 250 | 0 | 5 | 5 | 4 | 0 |
| 54 | 2000 | 0 | 5 | 5 | 5 | 2 |
| | 1000 | 0 | 5 | 5 | 5 | 1 |
| | 500 | 0 | 5 | 5 | 4 | 0 |
| 55 | 2000 | 0 | 5 | 5 | 1 | 0 |
| | 1000 | 0 | 5 | 4.5 | 0 | 0 |
| | 500 | 0 | 5 | 4 | 0 | 0 |
| 56 | 2000 | 0 | 5 | 5 | 5 | 4.5 |
| | 1000 | 0 | 5 | 5 | 5 | 4 |
| | 500 | 0 | 5 | 5 | 4.5 | 4 |
| | 250 | 0 | 5 | 5 | 4 | 3 |
| 57 | 2000 | 0 | 5 | 5 | 5 | 4.5 |
| | 1000 | 0 | 5 | 5 | 5 | 2 |
| | 500 | 0 | 5 | 5 | 3 | 0 |
| | 250 | 0 | 5 | 4.5 | 0 | 0 |
| 58 | 2000 | 0 | 5 | 5 | 5 | 4.5 |
| | 1000 | 0 | 5 | 5 | 5 | 4 |
| | 500 | 0 | 5 | 5 | 5 | 4 |
| | 250 | 0 | 4.5 | 5 | 5 | 3 |
| 59 | 2000 | 0 | 2 | 5 | 2 | 0 |
| 60 | 2000 | 0 | 5 | 5 | 5 | 2 |
| | 1000 | 0 | 4 | 5 | 4 | 1 |
| 61 | 2000 | 0 | 4 | 5 | 4 | 2 |
| | 1000 | 0 | 3 | 5 | 2 | 1 |
| 62 | 2000 | 0 | 3 | 5 | 4 | 3 |
| | 1000 | 0 | 3 | 5 | 2 | 2 |
| 63 | 2000 | 0 | 4 | 5 | 5 | 2 |
| | 1000 | 0 | 4 | 5 | 5 | 1 |
| | 500 | 0 | 3 | 5 | 5 | 0 |
| | 250 | 0 | 2.5 | 5 | 4 | 0 |
| 64 | 2000 | 0 | 5 | 5 | 5 | 5 |
| | 1000 | 0 | 5 | 5 | 5 | 4 |
| | 500 | 0 | 5 | 5 | 3 | 2 |
| 66 | 2000 | 0 | 5 | 5 | 5 | 5 |
| | 1000 | 0 | 5 | 5 | 5 | 4 |
| | 500 | 0 | 4.5 | 5 | 4.5 | 2 |
| 67 | 2000 | 0 | 5 | 5 | 5 | 2 |
| | 1000 | 0 | 4 | 5 | 4 | 1 |
| | 500 | 0 | 3 | 5 | 2 | 0 |
| 68 | 2000 | 0 | 5 | 5 | 5 | 5 |
| | 1000 | 0 | 5 | 5 | 5 | 4 |
| | 500 | 0 | 5 | 5 | 4 | 2 |
| | 250 | 0 | 4 | 5 | 3 | 0 |
| 69 | 2000 | 0 | 5 | 5 | 5 | 4 |
| | 1000 | 0 | 5 | 5 | 5 | 1 |
| | 500 | 0 | 5 | 4.5 | 3 | 0 |
| 70 | 2000 | 0 | 5 | 3 | 4 | 0 |
| 71 | 2000 | 0 | 5 | 5 | 2 | 0 |
| | 1000 | 0 | 5 | 5 | 0 | 0 |
| | 500 | 0 | 5 | 4.5 | 0 | 0 |
| | 250 | 0 | 5 | 4 | 0 | 0 |
| 72 | 2000 | 0 | 5 | 5 | 5 | 2 |
| | 1000 | 0 | 5 | 5 | 5 | 1 |
| | 500 | 0 | 4.5 | 5 | 4 | 0 |
| | 250 | 0 | 4 | 4 | 3 | 0 |
| 73 | 2000 | 0 | 5 | 5 | 4 | 0 |
| | 1000 | 0 | 5 | 5 | 3 | 0 |
| 76 | 2000 | 0 | 5 | 5 | 5 | 0 |
| 77 | 2000 | 0 | 3 | 5 | 5 | 3.5 |
| | 1000 | 0 | 1 | 5 | 4 | 3 |
| | 500 | 0 | 0 | 4.5 | 3.5 | 2 |
| 78 | 2000 | 0 | 2 | 5 | 1 | 1 |
| 82 | 2000 | 0 | 5 | 5 | 5 | 3 |
| | 1000 | 0 | 5 | 5 | 5 | 2 |
| | 500 | 0 | 5 | 5 | 4.5 | 0 |
| 83 | 2000 | 0 | 4 | 5 | 0 | 0 |
| 84 | 2000 | 0 | 4.5 | 5 | 4 | 0 |
| | 1000 | 0 | 4 | 4 | 1.5 | 0 |
| 87 | 2000 | 0 | 5 | 5 | 5 | 4 |
| | 1000 | 0 | 5 | 5 | 5 | 2 |
| | 500 | 0 | 4 | 5 | 4 | 1 |
| | 250 | 0 | 3 | 4.5 | 2 | 0 |
| 88 | 2000 | 0 | 5 | 5 | 5 | 2 |
| | 1000 | 0 | 5 | 5 | 5 | 1 |
| | 500 | 0 | 4 | 5 | 3 | 0 |
| | 250 | 0 | 2 | 4.5 | 2 | 0 |
| 89 | 2000 | 0 | 2 | 3 | 2 | 0 |
| 91 | 2000 | 0 | 5 | 5 | 5 | 0 |
| | 1000 | 0 | 5 | 5 | 4 | 0 |
| | 500 | 0 | 5 | 2 | 2 | 0 |
| | 250 | 0 | 4 | 2 | 2 | 0 |
| 92 | 2000 | 0 | 4 | 5 | 3 | 0 |
| 93 | 2000 | 0 | 4 | 3 | 4 | 3 |
| 94 | 2000 | 0 | 5 | 5 | 5 | 3 |
| | 1000 | 0 | 5 | 5 | 5 | 1 |
| | 500 | 0 | 5 | 4.5 | 5 | 0 |
| | 250 | 0 | 4 | 4.5 | 3.5 | 0 |
| 95 | 2000 | 1.5 | 5 | 5 | 5 | 4.5 |
| | 1000 | 1 | 5 | 5 | 5 | 4 |
| | 500 | 0 | 5 | 5 | 5 | 4 |
| | 250 | 0 | 5 | 4.5 | 4.5 | 3 |
| 96 | 2000 | 0 | 5 | 5 | 5 | 2 |
| | 1000 | 0 | 4.5 | 5 | 4.5 | 1 |
| 97 | 2000 | 0 | 5 | 5 | 5 | 4 |
| | 1000 | 0 | 5 | 5 | 4.5 | 2 |
| | 500 | 0 | 5 | 5 | 2 | 0 |
| | 250 | 0 | 5 | 5 | 0 | 0 |
| 98 | 2000 | 0 | 5 | 5 | 4 | 0 |
| | 1000 | 0 | 5 | 5 | 4 | 0 |
| | 500 | 0 | 5 | 4.5 | 4 | 0 |
| 99 | 2000 | 0 | 5 | 5 | 5 | 5 |
| | 1000 | 0 | 5 | 5 | 4.5 | 4.5 |
| | 500 | 0 | 4.5 | 5 | 3.5 | 2 |
| 100 | 2000 | 0 | 4 | 5 | 4.5 | 1 |
| | 1000 | 0 | 3.5 | 5 | 4 | 0 |
| 101 | 2000 | 0 | 3 | 5 | 0 | 0 |
| | 1000 | 0 | 2 | 5 | 0 | 0 |
| 102 | 2000 | 0 | 5 | 5 | 5 | 4 |
| | 1000 | 0 | 5 | 5 | 5 | 1 |
| | 500 | 0 | 5 | 5 | 3 | 0 |
| 103 | 2000 | 3 | 5 | 5 | 3 | 2 |
| 104 | 2000 | 0 | 5 | 5 | 4 | 0 |

TABLE 4-continued

| Compound No. | Dosage (g/10a) | Injury to rice | Herbicidal activity Echinochloa oryzicola | Broad-leaved weeds | Scirpus juncoides | Eleocharis acicularis |
|---|---|---|---|---|---|---|
| 107 | 1000 | 0 | 1 | 5 | 1 | 0 |
|  | 2000 | 0 | 5 | 5 | 5 | 2 |
|  | 1000 | 0 | 5 | 5 | 5 | 1 |
|  | 500 | 0 | 4.5 | 5 | 4.5 | 0 |
| 108 | 2000 | 0 | 4 | 4 | 5 | 0 |
| 109 | 2000 | 0 | 5 | 5 | 5 | 2 |
|  | 1000 | 0 | 4.5 | 5 | 4 | 1 |
|  | 500 | 0 | 4 | 5 | 3 | 0 |
| 110 | 2000 | 0 | 5 | 5 | 5 | 5 |
|  | 1000 | 0 | 5 | 5 | 3.5 | 4 |
|  | 500 | 0 | 3.5 | 5 | 3 | 2 |
| 111 | 2000 | 0 | 5 | 5 | 5 | 4 |
|  | 1000 | 0 | 5 | 5 | 3 | 1 |
| 112 | 2000 | 0 | 4 | 5 | 5 | 0 |
|  | 1000 | 0 | 3 | 1 | 1 | 0 |
| 115 | 2000 | 0 | 4 | 5 | 0 | 0 |
| 117 | 2000 | 0 | 4 | 5 | 3 | 0 |
| 118 | 2000 | 0 | 5 | 5 | 5 | 3 |
|  | 1000 | 0 | 5 | 5 | 2 | 2 |
| 119 | 2000 | 0 | 5 | 5 | 5 | 4 |
|  | 1000 | 0 | 3 | 5 | 4 | 4 |
| 121 | 2000 | 0 | 1 | 5 | 0 | 0 |
|  | 1000 | 0 | 0 | 5 | 0 | 0 |
|  | 500 | 0 | 0 | 5 | 0 | 0 |
| 122 | 1000 | 0 | 4 | 0 | 0 | 0 |
|  | 500 | 0 | 4 | 0 | 0 | 0 |
| 123 | 2000 | 0 | 3 | 4 | 0 | 0 |
| 127 | 2000 | 0 | 5 | 5 | 5 | 3 |
|  | 1000 | 0 | 5 | 5 | 5 | 3 |
|  | 500 | 0 | 5 | 5 | 4.5 | 3 |
|  | 250 | 0 | 3 | 0 | 3 | 0 |
| 129 | 2000 | 3.5 | 5 | 5 | 5 | 4.5 |
|  | 1000 | 0 | 5 | 5 | 5 | 4.5 |
|  | 500 | 0 | 5 | 5 | 5 | 3 |
|  | 250 | 0 | 5 | 5 | 4.5 | 0 |
| 130 | 2000 | 1 | 5 | 5 | 5 | 2 |
|  | 1000 | 0 | 5 | 5 | 5 | 2 |
|  | 500 | 0 | 5 | 5 | 5 | 2 |
|  | 250 | 0 | 5 | 5 | 5 | 2 |
|  | 125 | 0 | 5 | 5 | 5 | 0 |
| 132 | 1000 | 0 | 5 | 5 | 5 | 0 |
|  | 500 | 0 | 5 | 5 | 5 | 0 |
|  | 250 | 0 | 5 | 3.5 | 4 | 0 |
| 133 | 2000 | 0 | 5 | 5 | 5 | 5 |
|  | 1000 | 0 | 5 | 5 | 5 | 3 |
|  | 500 | 0 | 5 | 5 | 2 | 0 |
| 134 | 2000 | 0 | 4 | 5 | 4 | 4 |
|  | 1000 | 0 | 3 | 4 | 3 | 3 |
| 135 | 2000 | 0 | 5 | 5 | 5 | 5 |
|  | 1000 | 0 | 4 | 5 | 4.5 | 5 |
|  | 500 | 0 | 3 | 5 | 4 | 5 |
| 136 | 2000 | 0 | 4.5 | 5 | 5 | 2 |
| 138 | 2000 | 0 | 5 | 5 | 4 | 0 |
|  | 1000 | 0 | 4 | 5 | 1.5 | 0 |
|  | 500 | 0 | 2 | 5 | 0 | 0 |
| 139 | 1000 | 0 | 5 | 4.5 | 4 | 0 |
|  | 500 | 0 | 5 | 4 | 1 | 0 |
| 140 | 2000 | 0 | 5 | 5 | 5 | 0 |
|  | 1000 | 0 | 5 | 5 | 5 | 0 |
|  | 500 | 0 | 5 | 5 | 4.5 | 0 |
|  | 250 | 0 | 5 | 5 | 3 | 0 |
| 141 | 2000 | 0 | 4 | 5 | 4 | 2 |
| 142 | 2000 | 1 | 5 | 5 | 5 | 3 |
|  | 1000 | 0 | 5 | 5 | 5 | 2 |
|  | 500 | 0 | 5 | 5 | 5 | 2 |
|  | 250 | 0 | 5 | 5 | 4.5 | 2 |
| 143 | 2000 | 2 | 5 | 5 | 5 | 5 |
|  | 1000 | 0 | 5 | 5 | 5 | 5 |
|  | 500 | 0 | 5 | 5 | 5 | 4 |
|  | 200 | 0 | 5 | 5 | 5 | 4 |
|  | 125 | 0 | 5 | 5 | 5 | 4 |
| 144 | 2000 | 3.5 | 5 | 5 | 5 | 3 |
|  | 1000 | 0 | 5 | 5 | 5 | 3 |
|  | 500 | 0 | 5 | 5 | 5 | 2 |
|  | 250 | 0 | 5 | 5 | 5 | 1 |
|  | 125 | 0 | 4 | 4.5 | 4.5 | 0 |
| 146 | 2000 | 0 | 4.5 | 5 | 4 | 4 |
|  | 1000 | 0 | 4 | 5 | 3 | 2 |
| 148 | 2000 | 1 | 5 | 5 | 5 | 3 |
|  | 1000 | 0 | 5 | 5 | 5 | 2 |
|  | 500 | 0 | 4 | 5 | 4 | 0 |
|  | 250 | 0 | 3 | 4 | 4 | 0 |
| 149 | 2000 | 0 | 5 | 5 | 5 | 2 |
| 152 | 2000 | 2 | 5 | 5 | 5 | 5 |
|  | 1000 | 1 | 5 | 5 | 4 | 5 |
|  | 500 | 0 | 5 | 5 | 4 | 4 |
|  | 250 | 0 | 4 | 5 | 3 | 2 |
| 155 | 2000 | 0 | 5 | 4 | 4 | 0 |
| 156 | 1000 | 0 | 5 | 1 | 0 | 0 |
|  | 500 | 0 | 5 | 0 | 0 | 0 |
|  | 250 | 0 | 5 | 0 | 0 | 0 |
|  | 125 | 0 | 4.5 | 0 | 0 | 0 |
| 158 | 2000 | 0 | 5 | 5 | 2 | 2 |
|  | 1000 | 0 | 5 | 5 | 0 | 1 |
|  | 500 | 0 | 2 | 5 | 0 | 0 |
| 164 | 2000 | 0 | 5 | 5 | 3 | 1 |
|  | 1000 | 0 | 4 | 5 | 1 | 0 |
| 165 | 2000 | 0 | 5 | 5 | 5 | 4 |
|  | 1000 | 0 | 5 | 5 | 4 | 3.5 |
|  | 500 | 0 | 5 | 5 | 2 | 1 |
|  | 250 | 0 | 4.5 | 5 | 0 | 0 |
| 166 | 2000 | 0 | 4 | 5 | 5 | 0 |
|  | 1000 | 0 | 4 | 5 | 5 | 0 |
|  | 500 | 0 | 4 | 5 | 5 | 0 |
|  | 250 | 0 | 3.5 | 4 | 4 | 0 |
| 170 | 2000 | 0 | 2 | 5 | 0 | 0 |
| 172 | 2000 | 0 | 2 | 4 | 0 | 0 |
| 176 | 1000 | 2 | 5 | 5 | 5 | 5 |
|  | 500 | 1 | 5 | 5 | 5 | 5 |
|  | 250 | 0 | 5 | 5 | 5 | 5 |
|  | 125 | 0 | 5 | 5 | 4 | 3 |
| 177 | 500 | 2 | 5 | 5 | 5 | 5 |
|  | 250 | 1 | 5 | 5 | 5 | 5 |
|  | 125 | 0 | 5 | 5 | 5 | 4.5 |
|  | 62.5 | 0 | 5 | 5 | 5 | 4.5 |
| 178 | 2000 | 0 | 5 | 5 | 5 | 5 |
|  | 1000 | 0 | 5 | 5 | 5 | 5 |
|  | 500 | 0 | 5 | 5 | 5 | 5 |
|  | 250 | 0 | 4.5 | 5 | 5 | 5 |
| 179 | 2000 | 0 | 5 | 5 | 2 | 0 |
|  | 1000 | 0 | 5 | 5 | 0 | 0 |
| 180 | 2000 | 0 | 4 | 0 | 0 | 0 |
| 181 | 2000 | 0 | 5 | 5 | 5 | 4 |
|  | 1000 | 0 | 5 | 5 | 4 | 3 |
|  | 500 | 0 | 5 | 5 | 3 | 1 |
|  | 250 | 0 | 4 | 3 | 2 | 0 |
| 182 | 2000 | 2 | 4 | 5 | 5 | 4 |
|  | 1000 | 1 | 3 | 5 | 5 | 3 |
|  | 500 | 0 | 2 | 5 | 4 | 2 |
|  | 250 | 0 | 1 | 5 | 2 | 0 |
| 183 | 2000 | 0 | 5 | 5 | 5 | 4.5 |
|  | 1000 | 0 | 5 | 4.5 | 5 | 4 |
|  | 500 | 0 | 2 | 4.5 | 1 | 1 |
| 184 | 2000 | 0 | 5 | 5 | 4.5 | 5 |
|  | 1000 | 0 | 5 | 5 | 4 | 4.5 |
|  | 500 | 0 | 4 | 5 | 4 | 3 |
| 185 | 2000 | 0 | 3 | 4 | 4 | 3 |
| 189 | 2000 | 0 | 5 | 5 | 5 | 5 |
|  | 1000 | 0 | 5 | 5 | 5 | 5 |
|  | 500 | 0 | 5 | 5 | 5 | 5 |
|  | 250 | 0 | 4.5 | 5 | 5 | 5 |
| 190 | 2000 | 1 | 4.5 | 5 | 5 | 3 |
| 191 | 2000 | 3 | 5 | 5 | 5 | 3.5 |
|  | 1000 | 1 | 5 | 5 | 5 | 2 |
|  | 500 | 0 | 5 | 5 | 5 | 0 |
|  | 250 | 0 | 4.5 | 5 | 4 | 0 |
| 192 | 500 | 0 | 5 | 5 | 5 | 5 |
|  | 250 | 0 | 5 | 5 | 5 | 5 |
|  | 125 | 0 | 5 | 5 | 5 | 5 |
|  | 62.5 | 0 | 5 | 5 | 5 | 5 |
| 193 | 500 | 0 | 5 | 5 | 5 | 5 |
|  | 250 | 0 | 5 | 5 | 5 | 5 |
|  | 125 | 0 | 4 | 5 | 5 | 5 |
|  | 62.5 | 0 | 4 | 4 | 4 | 4.5 |

TABLE 4-continued

| Compound No. | Dosage (g/10a) | Injury to rice | Herbicidal activity | | | |
|---|---|---|---|---|---|---|
| | | | Echinochloa oryzicola | Broad-leaved weeds | Scirpus juncoides | Eleocharis acicularis |
| 194 | 2000 | 0 | 5 | 5 | 5 | 3 |
| | 1000 | 0 | 5 | 5 | 4 | 0 |
| | 500 | 0 | 5 | 2 | 2 | 0 |
| | 250 | 0 | 5 | 1 | 0 | 0 |
| 195 | 2000 | 0 | 4 | 5 | 4 | 3 |
| 198 | 2000 | 0 | 5 | 5 | 5 | 4 |
| | 1000 | 0 | 5 | 5 | 5 | 4 |
| | 500 | 0 | 5 | 5 | 5 | 2 |
| | 250 | 0 | 4 | 5 | 5 | 2 |
| 199 | 2000 | 0 | 5 | 5 | 0 | 0 |
| | 1000 | 0 | 4 | 4 | 0 | 0 |
| 200 | 1000 | 0 | 3 | 5 | 4.5 | 4 |
| | 500 | 0 | 2 | 5 | 4 | 3 |
| | 250 | 0 | 0 | 5 | 4 | 2 |
| | 125 | 0 | 0 | 5 | 4 | 0 |
| 201 | 2000 | 0 | 4 | 4 | 2 | 0 |
| 203 | 2000 | 2 | 2.5 | 5 | 4 | 4 |
| | 1000 | 1 | 1 | 5 | 4 | 4 |
| | 500 | 0 | 0 | 5 | 2 | 2 |
| 204 | 1000 | 0 | 5 | 5 | 5 | 5 |
| | 500 | 0 | 5 | 5 | 5 | 5 |
| | 250 | 0 | 5 | 5 | 5 | 5 |
| | 125 | 0 | 4 | 5 | 5 | 5 |
| 208 | 2000 | 0 | 4 | 4 | 3 | 0 |
| 209 | 2000 | 0 | 4 | 5 | 5 | 4 |
| | 1000 | 0 | 3 | 5 | 5 | 3 |
| | 500 | 0 | 1 | 5 | 4 | 2 |
| 210 | 2000 | 0 | 5 | 5 | 5 | 3 |
| | 1000 | 0 | 4 | 5 | 4 | 1 |
| 212 | 2000 | 0 | 4 | 5 | 5 | 2 |
| | 1000 | 0 | 4 | 4 | 4 | 1 |
| 213 | 500 | 4 | 5 | 5 | 5 | 5 |
| | 250 | 2 | 5 | 5 | 5 | 5 |
| | 125 | 0 | 5 | 5 | 5 | 5 |
| | 62.5 | 0 | 5 | 5 | 5 | 5 |
| 214 | 500 | 5 | 5 | 5 | 5 | 5 |
| | 250 | 3 | 5 | 5 | 5 | 5 |
| | 125 | 1 | 5 | 5 | 5 | 5 |
| | 62.5 | 0 | 5 | 5 | 5 | 5 |
| 215 | 2000 | 0 | 4 | 5 | 4 | 3 |
| | 1000 | 0 | 2 | 4 | 3 | 0 |
| 216 | 2000 | 0 | 4 | 5 | 5 | 5 |
| | 1000 | 0 | 3 | 4.5 | 4 | 3 |
| 217 | 2000 | 0 | 5 | 5 | 5 | 5 |
| | 1000 | 0 | 5 | 5 | 5 | 5 |
| | 500 | 0 | 5 | 5 | 5 | 5 |
| | 250 | 0 | 4.5 | 5 | 5 | 4.5 |
| 218 | 2000 | 2 | 5 | 5 | 5 | 5 |
| | 1000 | 1 | 5 | 5 | 5 | 5 |
| | 500 | 0 | 5 | 5 | 5 | 5 |
| | 250 | 0 | 5 | 5 | 5 | 5 |
| 219 | 2000 | 0 | 3 | 5 | 3 | 0 |
| 221 | 2000 | 0 | 3 | 5 | 1 | 2 |
| 222 | 500 | 0 | 5 | 5 | 5 | 4.5 |
| | 250 | 0 | 5 | 5 | 5 | 4.5 |
| | 125 | 0 | 5 | 5 | 5 | 4 |
| | 62.5 | 0 | 5 | 5 | 5 | 4 |
| 223 | 500 | 0 | 5 | 5 | 5 | 4.5 |
| | 250 | 0 | 5 | 5 | 5 | 4.5 |
| | 125 | 0 | 5 | 5 | 5 | 4.5 |
| | 62.5 | 0 | 5 | 5 | 5 | 4 |
| 224 | 1000 | 0 | 5 | 5 | 5 | 4 |
| | 500 | 0 | 5 | 5 | 5 | 4 |
| | 250 | 0 | 3 | 5 | 5 | 4 |
| 225 | 500 | 3 | 5 | 5 | 5 | 5 |
| | 250 | 3 | 5 | 5 | 5 | 5 |
| | 125 | 0 | 5 | 5 | 5 | 5 |
| | 62.5 | 0 | 5 | 5 | 1 | 3 |
| 226 | 1000 | 1 | 5 | 5 | 5 | 3 |
| | 500 | 1 | 5 | 5 | 5 | 3 |
| | 250 | 0 | 5 | 5 | 5 | 3 |
| | 125 | 0 | 1 | 5 | 5 | 0 |
| 227 | 1000 | 0 | 4 | 3 | 3 | 1 |
| 228 | 1000 | 0 | 4 | 5 | 5 | 0 |
| | 500 | 0 | 1 | 5 | 5 | 0 |
| | 250 | 0 | 0 | 5 | 2 | 0 |
| | 125 | 0 | 0 | 5 | 2 | 0 |
| 229 | 500 | 2 | 5 | 5 | 5 | 5 |
| | 250 | 0 | 5 | 5 | 5 | 5 |
| | 125 | 0 | 5 | 5 | 4 | 5 |
| | 62.5 | 0 | 3 | 5 | 1 | 4.5 |
| 230 | 500 | 2 | 5 | 5 | 5 | 5 |
| | 250 | 0 | 5 | 5 | 5 | 5 |
| | 125 | 0 | 5 | 5 | 5 | 5 |
| | 62.5 | 0 | 5 | 5 | 5 | 5 |
| 231 | 1000 | 1 | 4.5 | 5 | 5 | 5 |
| | 500 | 0 | 4 | 5 | 5 | 5 |
| | 250 | 0 | 4 | 5 | 5 | 4 |
| | 125 | 0 | 4 | 5 | 4 | 3 |
| 232 | 2000 | 0 | 4 | 5 | 4 | 0 |
| | 1000 | 0 | 3 | 5 | 2 | 0 |
| | 500 | 0 | 2 | 5 | 1 | 0 |
| 233 | 1000 | 2 | 5 | 5 | 5 | 5 |
| | 500 | 2 | 5 | 5 | 5 | 5 |
| | 250 | 0 | 2 | 5 | 4.5 | 4 |
| 234 | 1000 | 0 | 5 | 5 | 5 | 4 |
| | 500 | 0 | 5 | 5 | 5 | 2 |
| | 250 | 0 | 5 | 5 | 5 | 1 |
| | 125 | 0 | 4.5 | 5 | 5 | 1 |
| 235 | 1000 | 0 | 5 | 5 | 5 | 2 |
| | 500 | 0 | 5 | 5 | 5 | 1 |
| | 250 | 0 | 5 | 5 | 5 | 1 |
| | 125 | 0 | 5 | 5 | 5 | 1 |
| 236 | 1000 | 2 | 5 | 5 | 5 | 5 |
| | 500 | 1 | 5 | 5 | 5 | 5 |
| | 250 | 0 | 5 | 4.5 | 5 | 5 |
| | 125 | 0 | 5 | 4.5 | 5 | 5 |
| 237 | 500 | 1 | 5 | 5 | 5 | 5 |
| | 250 | 0 | 5 | 5 | 5 | 5 |
| | 125 | 0 | 5 | 5 | 5 | 5 |
| | 62.5 | 0 | 5 | 5 | 5 | 5 |
| 238 | 2000 | 0 | 0 | 5 | 4 | 0 |
| | 1000 | 0 | 0 | 5 | 4 | 0 |
| | 500 | 0 | 0 | 5 | 3.5 | 0 |
| 240 | 2000 | 0 | 4 | 5 | 0 | 0 |
| | 1000 | 0 | 3 | 5 | 0 | 0 |
| 241 | 500 | 0 | 5 | 5 | 5 | 5 |
| | 250 | 0 | 4 | 5 | 4.5 | 4 |
| | 125 | 0 | 2 | 4 | 4 | 4 |
| 242 | 500 | 0 | 5 | 5 | 5 | 5 |
| | 250 | 0 | 4.5 | 5 | 5 | 4.5 |
| | 125 | 0 | 4 | 5 | 4.5 | 3.5 |
| 243 | 2000 | 0 | 4 | 5 | 4.5 | 0 |
| | 1000 | 0 | 3 | 4 | 3 | 0 |
| 244 | 2000 | 0 | 4.5 | 5 | 5 | 4 |
| | 1000 | 0 | 4 | 3 | 3 | 3 |
| 246 | 2000 | 0 | 4 | 5 | 5 | 4.5 |
| | 1000 | 0 | 3 | 5 | 5 | 3 |
| 247 | 2000 | 0 | 4 | 5 | 0 | 0 |
| | 1000 | 0 | 1 | 5 | 0 | 0 |
| 249 | 2000 | 0 | 5 | 5 | 5 | 5 |
| | 1000 | 0 | 4 | 5 | 4 | 4 |
| 250 | 2000 | 0 | 5 | 5 | 3 | 2 |
| 251 | 2000 | 0 | 4 | 5 | 3 | 3 |
| | 1000 | 0 | 3 | 4 | 2 | 3 |
| 252 | 2000 | 0 | 4 | 5 | 5 | 0 |
| | 1000 | 0 | 4 | 5 | 3 | 0 |
| 253 | 1000 | 0 | 5 | 5 | 5 | 3 |
| | 500 | 0 | 5 | 5 | 3 | 0 |
| | 250 | 0 | 4 | 4 | 3 | 0 |
| 254 | 500 | 0 | 4 | 5 | 5 | 2 |
| | 250 | 0 | 4 | 5 | 5 | 2 |
| | 125 | 0 | 4 | 5 | 4 | 2 |
| | 62.5 | 0 | 4 | 5 | 4 | 2 |
| 255 | 500 | 0 | 0 | 5 | 0 | 0 |
| | 250 | 0 | 0 | 5 | 0 | 1 |
| | 125 | 0 | 0 | 5 | 0 | 0 |
| 256 | 500 | 0 | 1 | 5 | 0 | 0 |
| | 250 | 0 | 0 | 5 | 0 | 0 |
| | 125 | 0 | 0 | 5 | 0 | 0 |
| 257 | 1000 | 0 | 0 | 5 | 0 | 0 |
| | 500 | 0 | 0 | 5 | 0 | 0 |
| | 250 | 0 | 0 | 3 | 0 | 0 |
| 258 | 2000 | 0 | 5 | 5 | 5 | 4 |

TABLE 4-continued

| Compound No. | Dosage (g/10a) | Injury to rice | Echinochloa oryzicola | Broad-leaved weeds | Scirpus juncoides | Eleocharis acicularis |
|---|---|---|---|---|---|---|
| | 1000 | 0 | 5 | 5 | 5 | 3 |
| | 500 | 0 | 5 | 5 | 5 | 3 |
| | 250 | 0 | 5 | 5 | 5 | 3 |
| 259 | 2000 | 0 | 5 | 5 | 5 | 5 |
| | 1000 | 0 | 5 | 5 | 4 | 4 |
| 260 | 2000 | 0 | 5 | 5 | 5 | 4 |
| | 1000 | 0 | 5 | 5 | 5 | 4 |
| 261 | 2000 | 0 | 3.5 | 5 | 2 | 2 |
| 262 | 1000 | 0 | 5 | 5 | 5 | 4.5 |
| | 500 | 0 | 5 | 5 | 5 | 4.5 |
| | 250 | 0 | 5 | 4.5 | 4 | 4 |
| 263 | 2000 | 0 | 5 | 5 | 5 | 5 |
| | 1000 | 0 | 5 | 5 | 5 | 5 |
| | 500 | 0 | 5 | 5 | 4 | 2 |
| | 250 | 0 | 5 | 5 | 2 | 0 |
| 264 | 2000 | 0 | 5 | 5 | 4.5 | 4.5 |
| | 1000 | 0 | 5 | 5 | 4 | 1 |
| | 500 | 0 | 4.5 | 5 | 2 | 0 |
| | 250 | 0 | 2 | 5 | 0 | 0 |
| 265 | 2000 | 0 | 5 | 5 | 5 | 5 |
| | 1000 | 0 | 5 | 5 | 4 | 4 |
| | 500 | 0 | 5 | 5 | 2 | 2 |
| | 250 | 0 | 5 | 5 | 0 | 0 |
| 266 | 2000 | 0 | 5 | 5 | 3 | 5 |
| | 1000 | 0 | 5 | 5 | 3 | 4 |
| | 500 | 0 | 3 | 4.5 | 1 | 1 |
| 267 | 2000 | 0 | 5 | 5 | 3 | 5 |
| | 1000 | 0 | 5 | 5 | 3 | 4 |
| | 500 | 0 | 4 | 5 | 2 | 1 |
| 268 | 2000 | 0 | 3.5 | 5 | 2 | 0 |
| | 1000 | 0 | 3 | 5 | 1 | 0 |
| | 500 | 0 | 2.5 | 4.5 | 0 | 0 |
| 269 | 2000 | 0 | 4 | 5 | 1 | 0 |
| | 1000 | 0 | 1 | 4.5 | 0 | 0 |
| 270 | 2000 | 0 | 3 | 5 | 0 | 0 |
| 271 | 2000 | 0 | 5 | 5 | 4.5 | 4 |
| | 1000 | 0 | 5 | 5 | 4 | 1 |
| | 500 | 0 | 4.5 | 4.5 | 1 | 0 |
| 272 | 2000 | 4 | 5 | 5 | 5 | 4.5 |
| | 1000 | 2 | 4.5 | 5 | 3 | 1 |
| | 500 | 0 | 3 | 4 | 1 | 0 |
| 273 | 2000 | 0 | 5 | 5 | 4.5 | 5 |
| | 1000 | 0 | 5 | 5 | 4 | 5 |
| | 500 | 0 | 4 | 5 | 2 | 1 |
| | 250 | 0 | 3 | 5 | 0 | 0 |
| 274 | 2000 | 0 | 5 | 5 | 5 | 2 |
| 275 | 2000 | 0 | 5 | 5 | 5 | 2 |
| | 1000 | 0 | 5 | 5 | 3 | 0 |
| 276 | 2000 | 0 | 5 | 5 | 2 | 2 |
| | 1000 | 0 | 2 | 5 | 1 | 1 |
| 277 | 2000 | 0 | 4 | 5 | 4 | 3 |
| | 1000 | 0 | 3.5 | 5 | 4 | 3 |
| | 500 | 0 | 3.5 | 4 | 3 | 3 |
| | 250 | 0 | 3 | 4 | 3 | 2 |
| 278 | 2000 | 0 | 3 | 5 | 4 | 4.5 |
| | 1000 | 0 | 2 | 5 | 3 | 4 |
| | 500 | 0 | 1 | 5 | 2 | 3 |
| 279 | 2000 | 0 | 4.5 | 4.5 | 3 | 0 |
| 282 | 2000 | 0 | 3 | 4.5 | 2 | 1 |
| 284 | 2000 | 0 | 4.5 | 5 | 4.5 | 0 |
| | 1000 | 0 | 4.5 | 5 | 4 | 0 |
| 286 | 2000 | 0 | 5 | 5 | 5 | 4 |
| | 1000 | 0 | 4.5 | 5 | 4 | 2 |
| | 500 | 0 | 4.5 | 5 | 2 | 0 |
| | 250 | 0 | 4 | 5 | 0 | 0 |
| 287 | 2000 | 0 | 5 | 4 | 2 | 0 |
| 289 | 2000 | 0 | 3 | 4 | 4 | 0 |
| 290 | 2000 | 0 | 5 | 0 | 0 | 0 |
| | 1000 | 0 | 5 | 0 | 0 | 0 |
| 291 | 2000 | 0 | 2 | 5 | 0 | 0 |
| 292 | 2000 | 0 | 4 | 5 | 2 | 0 |

TEST EXAMPLE 2 (FOLIAR TREATMENT)

Seeds of rice, wheat, *Panicum crus-galli*, *Digitaria adscendens*, *Amaranthus viridis*, and radish were sown in unglazed pots filled with upland soil, and covered with a 1-cm soil layer. When they emerged and reached the 3–4 leaf stage, a diluted wettable powder containing each of the active compounds of the invention shown in Table 5 was sprayed at a rate of 100 liters per 10 ares.

On the fifteenth day after treatment, the degree of injury to each plant was examined, and the results were rated in the same way as in Test Example 1. The results are shown in Table 5.

TABLE 5

| Compound No. | Concentration (%) | Rice | Wheat | Radish | Panicum crus-galli | Digitaria adscendens | Amaranthus viridis |
|---|---|---|---|---|---|---|---|
| 1 | 1.0 | 4 | 4 | 5 | 5 | 5 | — |
| | 0.5 | 2 | 2 | 4 | 3 | 3.5 | — |
| 2 | 1.0 | 2 | 4 | 5 | 5 | 5 | — |
| | 0.5 | 1 | 2 | 5 | 3 | 5 | — |
| 3 | 1.0 | 2.5 | 3 | 5 | 5 | 5 | — |
| | 0.5 | 1.5 | 2 | 5 | 5 | 4 | — |
| 4 | 1.0 | 2.5 | 3 | 5 | 5 | 5 | — |
| | 0.5 | 1.5 | 1 | 5 | 5 | 5 | — |
| 5 | 1.0 | 2 | 2 | 5 | 5 | 5 | — |
| | 0.5 | 0.5 | 1 | 5 | 2 | 2 | — |
| 6 | 1.0 | 1 | 1 | 4 | 4 | 2 | — |
| 7 | 1.0 | 1.5 | 3 | 4 | 2 | 4 | — |
| 8 | 1.0 | 2 | 2 | 5 | 5 | 5 | — |
| | 0.5 | 1 | 1 | 5 | 4 | 5 | — |
| 9 | 1.0 | 0 | — | 5 | 2 | 2 | — |
| 10 | 1.0 | 1 | 3 | 5 | 5 | 5 | — |
| | 0.5 | 0 | 2 | 5 | 5 | 5 | — |
| 16 | 1.0 | 0 | — | 5 | 4 | 5 | 5 |
| | 0.5 | 0 | — | 5 | 1 | 2 | 3 |
| 17 | 1.0 | 0 | — | 5 | 1 | 2 | 5 |
| | 0.5 | 0 | — | 5 | 0 | 0 | 4.5 |
| 18 | 1.0 | 0 | — | 5 | 4 | 5 | 5 |
| | 0.5 | 0 | — | 3 | 1 | 2 | 2 |
| 19 | 1.0 | 1.5 | — | 5 | 2 | 5 | 3 |
| | 0.5 | 0 | — | 3 | 0 | 2 | 1 |

TABLE 5-continued

| Compound No. | Concentration (%) | Test Plants | | | | | |
|---|---|---|---|---|---|---|---|
| | | Rice | Wheat | Radish | Panicum crus-galli | Digitaria adscendens | Amaranthus viridis |
| 20 | 1.0 | 4.5 | 4.5 | 5 | 5 | 5 | 5 |
| | 0.5 | 4 | 4.5 | 5 | 5 | 5 | 5 |
| | 0.25 | 2 | 4 | 5 | 4 | 4 | 5 |
| 21 | 1.0 | 0 | 0 | 5 | 5 | 5 | 5 |
| | 0.5 | 0 | 0 | 5 | 2 | 5 | 5 |
| | 0.25 | 0 | 0 | 2 | 0 | 3 | 5 |
| 22 | 1.0 | 0.5 | 5 | 5 | 5 | 5 | — |
| | 0.5 | 0 | 4 | 5 | 5 | 5 | — |
| | 0.25 | 0 | 2 | 5 | 5 | 5 | — |
| 23 | 1.0 | — | 5 | 5 | 5 | 5 | 5 |
| | 0.5 | — | 4 | 5 | 3 | 3.5 | 5 |
| 24 | 1.0 | 4.5 | — | 5 | 5 | 5 | 5 |
| | 0.5 | 3 | — | 5 | 5 | 5 | 5 |
| | 0.25 | 2 | — | 5 | 4.5 | 5 | 5 |
| 25 | 1.0 | 2 | — | 4.5 | 5 | 5 | 5 |
| | 0.5 | 1.5 | — | 1 | 1.5 | 2 | 4.5 |
| 26 | 1.0 | 5 | — | 5 | 5 | 5 | 5 |
| | 0.5 | 2 | — | 5 | 5 | 5 | 5 |
| | 0.25 | 0 | — | 4 | 4 | 4 | 5 |
| 35 | 1.0 | 1 | — | 2 | 0 | 2 | 5 |
| 36 | 1.0 | 0 | — | 5 | 0 | 2 | 5 |
| 37 | 1.0 | 0 | — | 5 | 0 | 3 | 5 |
| 42 | 1.0 | 0 | — | 5 | 0 | 2.5 | 3 |
| 46 | 1.0 | 1.5 | 1 | 4 | 1 | 4 | — |
| 60 | 1.0 | 1.5 | — | 5 | 2.5 | 4 | 4.5 |
| 61 | 1.0 | 1.5 | — | 5 | 2 | 3.5 | 4 |
| 66 | 1.0 | 5 | — | 5 | 5 | 5 | 5 |
| 67 | 1.0 | 3 | — | 5 | 4 | 5 | 5 |
| | 0.5 | 2 | — | 5 | 3 | 3.5 | 3.5 |
| 75 | 1.0 | 0.5 | 0 | 5 | 3 | 2 | — |
| 78 | 1.0 | 2 | — | 5 | 3 | 4.5 | — |
| 87 | 1.0 | 0 | 0 | 5 | 2 | 3 | 5 |
| 88 | 1.0 | 0 | 0 | 4 | 1.5 | 3 | 5 |
| 103 | 1.0 | 0 | 0 | 5 | 1 | 2 | 5 |
| 107 | 1.0 | 0 | 0 | 3 | 2 | 3 | 5 |
| 110 | 1.0 | 0 | 1 | 2.5 | 0 | 4 | 5 |
| 133 | 1.0 | 2 | — | 4 | 3 | 4.5 | 4 |
| 139 | 1.0 | 1 | — | 5 | 5 | 3 | 5 |
| 144 | 1.0 | 1 | — | 5 | 4.5 | 5 | 5 |
| | 0.5 | 0 | — | 5 | 1 | 2 | 5 |
| 145 | 1.0 | 2 | — | 5 | 4 | 5 | 5 |
| | 0.5 | 0 | — | 4 | 1 | 2 | 5 |
| 146 | 1.0 | 1 | — | 5 | 5 | 5 | 5 |
| | 0.5 | 0 | — | 5 | 1.5 | 3 | 5 |
| | 0.25 | 0 | — | 5 | 0 | 2 | 5 |
| 147 | 1.0 | 0 | — | 0 | 0 | 0 | 5 |
| 149 | 1.0 | 0 | — | 5 | 0.5 | 2.5 | 3 |
| 151 | 1.0 | 0 | — | 5 | 0 | 2 | 5 |
| 154 | 1.0 | 0 | — | 5 | 0 | 1 | 4 |
| 175 | 1.0 | 0 | — | 5 | 1.5 | 2.5 | 5 |
| 176 | 1.0 | 4 | 2 | 3.5 | 4 | 5 | 5 |
| | 0.5 | 1 | 1 | 3 | 4 | 5 | 5 |
| | 0.25 | 0 | 0 | 1.5 | 3.5 | 4 | 5 |
| 177 | 1.0 | 0 | 1 | 4 | 4 | 4.5 | 5 |
| | 0.5 | 0 | 0 | 3 | 3 | 3 | 5 |
| 178 | 1.0 | 0 | 0 | 4 | 3 | 4 | 3 |
| 202 | 1.0 | 0 | — | 5 | 2 | 3 | 5 |
| 213 | 1.0 | 2 | — | 5 | 5 | 5 | 5 |
| | 0.5 | 1.5 | — | 5 | 4.5 | 5 | 5 |
| | 0.25 | 0 | — | 5 | 4.5 | 5 | 5 |
| 214 | 1.0 | 0.5 | — | 4 | 4.5 | 4 | 3 |
| 215 | 1.0 | 0 | — | 2 | 0 | 1 | 4.5 |
| 222 | 1.0 | 2 | — | 5 | 5 | 5 | 5 |
| | 0.5 | 0 | — | 5 | 4.5 | 5 | 5 |
| | 0.25 | 0 | — | 5 | 4 | 5 | 5 |
| 223 | 1.0 | 1 | — | 5 | 5 | 5 | 5 |
| | 0.5 | 0 | — | 5 | 5 | 5 | 5 |
| | 0.25 | 0 | — | 5 | 4 | 4.5 | 5 |
| 225 | 1.0 | 1 | — | 5 | 5 | 5 | 5 |
| | 0.5 | 0.5 | — | 4 | 3 | 5 | 4.5 |
| | 0.25 | 0 | — | 3.5 | 3 | 4 | 4 |
| 226 | 1.0 | 0 | — | 1 | 0.5 | 4 | 4 |
| 228 | 1.0 | 0 | — | 1 | 0 | 5 | 3.5 |
| 229 | 1.0 | 0 | — | 5 | 5 | 5 | 5 |
| | 0.5 | 0 | — | 5 | 4 | 4 | 5 |
| | 0.25 | 0 | — | 0 | 4 | 4 | 4 |
| 230 | 1.0 | 0 | — | 2 | 5 | 5 | 5 |
| | 0.5 | 0 | — | 0 | 3 | 3 | 5 |
| 233 | 1.0 | 0 | — | 3 | 2 | 4 | 5 |

TABLE 5-continued

| Compound No. | Concentration (%) | Test Plants | | | | |
|---|---|---|---|---|---|---|
| | | Rice | Wheat | Radish | Panicum crus-galli | Digitaria adscendens | Amaranthus viridis |
| 234 | 1.0 | 0 | — | 4 | 2 | 3 | 3 |
| 235 | 1.0 | 0 | — | 4 | 1 | 3 | 4 |
| 237 | 1.0 | 0 | — | 3.5 | 5 | 4 | 4 |
| 247 | 1.0 | 0 | — | 0 | 0 | 3 | 5 |
| 255 | 1.0 | 0 | — | 0 | 0.5 | 1 | 5 |
| 258 | 1.0 | 0 | — | 4 | 2 | 4 | 2 |
| 261 | 1.0 | 1.5 | — | 5 | 2 | 5 | — |
| | 0.5 | 0 | — | 5 | 0 | 4.5 | — |
| 262 | 1.0 | — | 5 | 5 | 5 | 5 | 5 |
| | 0.5 | — | 2.5 | 5 | 5 | 5 | 5 |
| 263 | 1.0 | 1.5 | — | 5 | 4.5 | 5 | 5 |
| | 0.5 | 0 | — | 4.5 | 4 | 4.5 | 4 |
| 264 | 1.0 | 1 | — | 5 | 4 | 4 | 5 |
| | 0.5 | 0.5 | — | 4 | 1.5 | 2 | 4 |
| 265 | 1.0 | 1.5 | — | 5 | 5 | 5 | 5 |
| 266 | 1.0 | — | 0 | 2 | 2 | 4.5 | 5 |
| | 0.5 | — | 0 | 2 | 1 | 4 | 4 |
| 268 | 1.0 | — | 0 | 2 | 1 | 3 | 5 |
| 271 | 1.0 | 0 | — | 3.5 | 1.5 | 4 | 4 |
| | 0.5 | 0 | — | 2 | 0.5 | 3.5 | 3 |
| 272 | 1.0 | 3 | — | 5 | 5 | 5 | 5 |
| | 0.5 | 1 | — | 4 | 4 | 4.5 | 2 |
| 273 | 1.0 | 1.5 | — | 5 | 4 | 5 | 5 |
| | 0.5 | 1 | — | 4 | 3 | 3 | 3 |
| 274 | 1.0 | 1 | — | 4 | 4 | 4 | 4 |
| 294 | 1.0 | 0 | 0 | 5 | 2 | 5 | — |
| | 0.5 | 0 | 0 | 4.5 | 0 | 4 | — |
| | 0.25 | 0 | 0 | 2 | 0 | 1.5 | — |
| 295 | 1.0 | 0 | 0 | 1.5 | 0.5 | 0.5 | — |
| 296 | 1.0 | 0 | 0 | 3.5 | 1 | 2 | — |
| 297 | 1.0 | 0 | 0 | 2.5 | 1 | 2 | — |
| 298 | 1.0 | 0 | 0 | 2 | 2 | 0 | — |
| 299 | 1.0 | 0 | 0 | 1 | 1 | 1 | — |
| 300 | 1.0 | 0 | 0 | 1 | 2 | 2 | — |
| 301 | 1.0 | 0.5 | — | 4.5 | 1 | 5 | — |
| | 0.5 | 0 | — | 4 | 0.5 | 5 | — |
| | 0.25 | 0 | — | 1 | 0 | 5 | — |
| 302 | 1.0 | 0.5 | — | 5 | 5 | 5 | — |
| | 0.5 | 0 | — | 3.5 | 2 | 5 | — |
| 303 | 1.0 | 0 | — | 3 | 0.5 | 3.5 | — |

TEST EXAMPLE 3 (SOIL TREATMENT IN UPLAND FIELD CONDITION)

Upland farm soil was filled in polyethylene pots (1/5,000 are), and levelled. Wheat, rice, radish, corn, and soybean were sown, and covered with soil containing the seeds of *Digitaria adscendens, Echinochloa crus-galli* and *Amaranthus viridis* to a thickness of 2 cm. Immediately then, a diluted wettable powder containing the active compound of the invention was sprayed at a rate of 200 liters per 10 ares. Then, the plants were grown for 3 weeks in a glass chamber, and examined. The results are shown in Table 6. The figures in the table show the injuries to the crops and the herbicidal activities on the weeds which were rated in the same way as in Test Example 1.

TABLE 6

| Compound No. | Dosage (g/10a) | Injury to crops | | | | | Herbicidal activity | | |
|---|---|---|---|---|---|---|---|---|---|
| | | Wheat | Rice | Radish | Corn | Soybean | Digitaria adscendens | Echinochloa crus-galli | Amaranthus viridis |
| 176 | 1000 | 0 | 0 | 0.5 | 0 | 0 | 5 | 5 | 5 |
| | 500 | 0 | 0 | 0 | 0 | 0 | 5 | 5 | 5 |
| | 250 | 0 | 0 | 0 | 0 | 0 | 5 | 5 | 5 |
| | 125 | 0 | 0 | 0 | 0 | 0 | 5 | 5 | 4 |
| 177 | 1000 | 0 | 0 | 1 | 0 | 0 | 5 | 5 | 5 |
| | 500 | 0 | 0 | 0 | 0 | 0 | 5 | 5 | 5 |
| | 250 | 0 | 0 | 0 | 0 | 0 | 5 | 5 | 5 |
| | 125 | 0 | 0 | 0 | 0 | 0 | 5 | 5 | 5 |
| | 62.5 | 0 | 0 | 0 | 0 | 0 | 5 | 5 | 4.5 |
| 191 | 1000 | 0 | 0 | 0 | 0 | 0 | 3 | 3 | 4 |
| | 500 | 0 | 0 | 0 | 0 | 0 | 2 | 1 | 2 |
| 213 | 500 | 2 | 1.5 | 1 | 1 | 0 | 5 | 5 | 5 |
| | 250 | 1 | 0 | 0 | 0 | 0 | 5 | 5 | 5 |
| | 125 | 0 | 0 | 0 | 0 | 0 | 5 | 5 | 5 |
| | 62.5 | 0 | 0 | 0 | 0 | 0 | 5 | 4.5 | 5 |
| 214 | 500 | 2 | 1.5 | 2 | 2 | 0 | 5 | 5 | 5 |
| | 250 | 1 | 0 | 0 | 0 | 0 | 5 | 5 | 5 |
| | 125 | 0 | 0 | 0 | 0 | 0 | 5 | 5 | 5 |
| | 62.5 | 0 | 0 | 0 | 0 | 0 | 5 | 4.5 | 5 |

TEST EXAMPLE 4

Upland soil was filled into unglazed pots having a diameter of 20 cm. Seeds of *Digitaria adscendens*, and broad-leaved weeds (*Chenopodium ficifolium* and *Amaranthus viridis*) were uniformly mixed with a 1-cm surface layer of the soil. Immediately then, a diluted mixture of the active compound of the invention and another herbicide was applied to the soil surface. The plants were grown for 20 days, and examined. The results are shown in Table 7.

TABLE 7

| Herbicides | | | | Herbicidal activity | |
|---|---|---|---|---|---|
| Compound No. | Dosage (g/10a) | Other herbicides | Dosage (g/10a) | Digitaria adscendens | Broad-leaved weeds |
| 176 | 400 | — | — | 4.5 | 4.5 |
|  | 200 | — | — | 4 | 4 |
|  | 100 | — | — | 3 | 3.5 |
| 177 | 100 | — | — | 5 | 5 |
|  | 50 | — | — | 4 | 4.5 |
|  | 25 | — | — | 2.5 | 2.5 |
| 213 | 25 | — | — | 3 | 3 |
|  | 12.5 | — | — | 2 | 2.5 |
| 214 | 25 | — | — | 3 | 3 |
|  | 12.5 | — | — | 2 | 2.5 |
| 222 | 25 | — | — | 3 | 3 |
|  | 12.5 | — | — | 2 | 2 |
| 230 | 25 | — | — | 2.5 | 2.5 |
|  | 12.5 | — | — | 1.5 | 2 |
| 237 | 25 | — | — | 2 | 2.5 |
|  | 12.5 | — | — | 1 | 2 |
| — | — | trifluralin | 40 | 2.5 | 2.5 |
| — | — | " | 20 | 1.5 | 1.5 |
| 176 | 100 | " | 20 | 4.5 | 4 |
| 177 | 25 | " | 20 | 5 | 5 |
| 214 | 12.5 | " | 20 | 5 | 5 |
| — | — | amiben | 50 | 2 | 2 |
| — | — | " | 25 | 1 | 1.5 |
| 213 | 12.5 | " | 25 | 5 | 5 |
| 222 | 12.5 | " | 25 | 5 | 5 |
| 230 | 12.5 | " | 25 | 5 | 5 |
| — | — | alachlor | 40 | 3 | 2 |
| — | — | " | 20 | 2 | 1.5 |
| 176 | 100 | " | 20 | 5 | 5 |
| 214 | 12.5 | " | 20 | 5 | 5 |
| 237 | 12.5 | " | 20 | 5 | 5 |
| — | — | dichlobenil | 40 | 1 | 1.5 |
| 177 | 25 | " | 40 | 4.5 | 5 |
| 213 | 12.5 | " | 40 | 5 | 5 |
| 222 | 12.5 | " | 40 | 5 | 5 |
| — | — | chloro propham | 40 | 2 | 1 |

TABLE 7-continued

| Herbicides | | | | Herbicidal activity | |
|---|---|---|---|---|---|
| Compound No. | Dosage (g/10a) | Other herbicides | Dosage (g/10a) | Digitaria adscendens | Broad-leaved weeds |
| 176 | 100 | " | 40 | 5 | 5 |
| 214 | 12.5 | " | 40 | 5 | 4.5 |
| 230 | 12.5 | " | 40 | 5 | 4.5 |
| — | — | linuron | 50 | 2 | 1.5 |
| 177 | 25 | " | 50 | 5 | 5 |
| 230 | 12.5 | " | 50 | 5 | 5 |
| 237 | 12.5 | " | 50 | 4.5 | 4 |
| — | — | diuron | 50 | 2 | 1.5 |
| — | — | " | 25 | 0 | 1 |
| 176 | 100 | " | 25 | 5 | 5 |
| 213 | 12.5 | " | 50 | 5 | 5 |
| 237 | 12.5 | " | 50 | 5 | 5 |
| — | — | simazine | 50 | 2.0 | 3 |
| — | — | " | 25 | 1.5 | 2 |
| 177 | 25 | " | 25 | 5 | 5 |
| 214 | 12.5 | " | 25 | 5 | 5 |
| 222 | 12.5 | " | 25 | 5 | 5 |
| — | — | atrazine | 50 | 2.5 | 2 |
| 176 | 100 | " | 50 | 5 | 5 |
| 222 | 12.5 | " | 50 | 5 | 5 |
| 230 | 12.5 | " | 50 | 5 | 5 |
| — | — | DNBP | 500 | 2 | 2.5 |
| — | — | " | 250 | 1 | 1 |
| 177 | 25 | " | 250 | 5 | 5 |
| 214 | 12.5 | " | 250 | 4.5 | 5 |
| 237 | 12.5 | " | 250 | 4 | 4.5 |
| Non-treated lot | | | | 0 | 0 |

TEST EXAMPLE 5

Paddy soil was filled into Wagner pots with a diameter of 20 cm. Seeds of *Echinochloa oryzicola*, *Scirpus juncoides* and broad-leaved weeds (*Monochoria vaginalis*, *Rotala indica* and *Lindernia Procumbens*) were mixed uniformly with a 1-cm surface layer of the soil. Furthermore, two seedlings of *Eleocharis acicularis* were transplanted. The soil was submerged to a level of 3 cm, and seedlings of rice in the 2- to 3-leaf stage were transplanted to a depth of 2 cm.

Then, upon the emergence of the weeds, a diluted mixture of each of the test compounds of the invention and another herbicide was applied dropwise. After growing the plants for 20 days, the degrees of injury to rice and the herbicidal activities of the herbicidal compositions were examined. The results are shown in Table 8.

TABLE 8

| Herbicides | | | | | Herbicidal Acitivity | | | |
|---|---|---|---|---|---|---|---|---|
| Compound No. | Dosage (g/10a) | Other herbicides | Dosage (g/10a) | Injury to rice | Echinochloa oryzicola | Broad-leaved weeds | Scirpus juncoides | Eleocharis acicularis |
| 176 | 100 | — | — | 0 | 3 | 4 | 4 | 4 |
|  | 50 | — | — | 0 | 2 | 3 | 3 | 2 |
|  | 25 | — | — | 0 | 1 | 1.5 | 1 | 1 |
| 177 | 25 | — | — | 0 | 4 | 5 | 5 | 4.5 |
|  | 12.5 | — | — | 0 | 2 | 3 | 3 | 2 |
|  | 6.25 | — | — | 0 | 1.5 | 2 | 1.5 | 1.5 |
| 213 | 12.5 | — | — | 0 | 2.5 | 3.5 | 3 | 3 |
|  | 6.25 | — | — | 0 | 2 | 2.5 | 2 | 2 |
| 214 | 12.5 | — | — | 0 | 1.5 | 2 | 1.5 | 1.5 |
|  | 6.25 | — | — | 0 | 1 | 1.5 | 1 | 1 |
| 217 | 12.5 | — | — | 0 | 2.5 | 3 | 2 | 2 |
|  | 6.25 | — | — | 0 | 2 | 2 | 1.5 | 1 |
| 222 | 12.5 | — | — | 0 | 3 | 3.5 | 3 | 2.5 |
|  | 6.25 | — | — | 0 | 2 | 2.5 | 2 | 2 |
| 223 | 12.5 | — | — | 0 | 2.5 | 3 | 2 | 2 |
|  | 6.25 | — | — | 0 | 2 | 2 | 1.5 | 1.5 |
| 229 | 12.5 | — | — | 0 | 1.5 | 2 | 1.5 | 1.5 |
|  | 6.25 | — | — | 0 | 0 | 1.5 | 1 | 0 |

TABLE 8-continued

| Herbicides | | | | | Herbicidal Acitivity | | | |
|---|---|---|---|---|---|---|---|---|
| Compound No. | Dosage (g/10a) | Other herbicides | Dosage (g/10a) | Injury to rice | Echinochloa oryzicola | Broad-leaved weeds | Scirpus juncoides | Eleocharis acicularis |
| 230 | 12.5 | — | — | 0 | 1.5 | 2 | 2 | 1.5 |
|  | 6.25 | — | — | 0 | 1 | 1.5 | 1 | 0 |
| 237 | 12.5 | — | — | 0 | 2 | 2.5 | 2 | 1.5 |
|  | 6.25 | — | — | 0 | 1 | 2 | 1 | 1 |
| 242 | 12.5 | — | — | 0 | 2 | 3 | 2 | 1 |
|  | 6.25 | — | — | 0 | 1 | 2 | 1 | 0 |
| — | — | simetryne | 50 | 0 | 3 | 3 | 2 | 1.5 |
| — | — | " | 25 | 0 | 2 | 2 | 1 | 0 |
| 177 | 6.25 | " | 25 | 0 | 5 | 5 | 5 | 5 |
| 213 | 6.25 | " | 25 | 0 | 5 | 5 | 5 | 5 |
| 214 | 6.25 | " | 25 | 0 | 5 | 5 | 5 | 4.5 |
| 222 | 6.25 | " | 25 | 0 | 5 | 5 | 5 | 5 |
| — | — | MT 101 | 100 | 0 | 1 | 2.5 | 1 | 1 |
| — | — | " | 50 | 0 | 1 | 2 | 1 | 0 |
| 177 | 6.25 | " | 50 | 0 | 4 | 5 | 5 | 5 |
| 217 | 6.25 | " | 50 | 0 | 4.5 | 5 | 4.5 | 4 |
| 223 | 6.25 | " | 50 | 0 | 5 | 5 | 5 | 5 |
| 230 | 6.25 | " | 50 | 0 | 5 | 5 | 5 | 4.5 |
| — | — | SK 223 | 200 | 0 | 0 | 0 | 3 | 2 |
| — | — | " | 100 | 0 | 0 | 0 | 2 | 2 |
| 177 | 6.25 | " | 100 | 0 | 5 | 5 | 5 | 5 |
| 214 | 6.25 | " | 100 | 0 | 5 | 5 | 5 | 5 |
| 222 | 6.25 | " | 100 | 0 | 5 | 5 | 5 | 5 |
| 229 | 6.25 | " | 100 | 0 | 5 | 5 | 4 | 4 |
| — | — | oxadiazon | 40 | 0 | 3 | 3 | 2 | 0 |
| — | — | " | 20 | 0 | 3 | 2.5 | 1.5 | 0 |
| 176 | 25 | " | 20 | 0 | 5 | 5 | 5 | 5 |
| 177 | 6.25 | " | 20 | 0 | 5 | 5 | 5 | 5 |
| 217 | 12.5 | " | 20 | 0 | 5 | 5 | 5 | 5 |
| — | — | benthiocarb | 100 | 0 | 3 | 2 | 2 | 1 |
| — | — | " | 50 | 0 | 2 | 0 | 0 | 0 |
| 176 | 25 | " | 50 | 0 | 5 | 5 | 4.5 | 4 |
| 177 | 6.25 | " | 50 | 0 | 5 | 5 | 5 | 5 |
| 230 | 6.25 | " | 50 | 0 | 5 | 5 | 5 | 4.5 |
| — | — | chloro-nitrofen | 100 | 0 | 2 | 3 | 1 | 0 |
| — | — | chloro-nitrofen | 50 | 0 | 1.5 | 2 | 0 | 0 |
| 177 | 6.25 | chloro-nitrofen | 50 | 0 | 5 | 5 | 5 | 5 |
| 214 | 6.25 | chloro-nitrofen | 50 | 0 | 5 | 5 | 5 | 5 |
| 237 | 6.25 | chloro-nitrofen | 50 | 0 | 5 | 5 | 4 | 4 |
| — | — | butachlor | 50 | 0 | 3.5 | 2 | 2 | 1 |
| — | — | " | 25 | 0 | 3 | 1 | 1 | 0 |
| 176 | 25 | " | 25 | 0 | 5 | 5 | 5 | 5 |
| 177 | 6.25 | " | 25 | 0 | 5 | 5 | 5 | 5 |
| 229 | 6.25 | " | 25 | 0 | 5 | 5 | 5 | 5 |
| — | — | molinate | 100 | 0 | 3 | 1.5 | 2 | 1 |
| — | — | " | 50 | 0 | 2 | 1.5 | 2 | 0 |
| 176 | 25 | " | 50 | 0 | 4 | 5 | 4 | 4 |
| 177 | 6.25 | " | 50 | 0 | 4 | 5 | 5 | 4.5 |
| 222 | 6.25 | " | 50 | 0 | 5 | 5 | 5 | 4.5 |
| — | — | MCP | 25 | 0 | 1 | 3 | 1 | 1 |
| — | — | " | 12.5 | 0 | 0 | 2 | 1 | 0 |
| 176 | 25 | " | 12.5 | 0 | 5 | 5 | 5 | 5 |
| 213 | 6.25 | " | 12.5 | 0 | 5 | 5 | 5 | 5 |
| 217 | 6.25 | " | 12.5 | 0 | 5 | 5 | 4.5 | 4 |
| 223 | 6.25 | " | 12.5 | 0 | 5 | 5 | 5 | 5 |
| Non-treated lot | | | | 0 | 0 | 0 | 0 | 0 |

TEXT EXAMPLE 6

Paddy soil was filled into Wagner pots with a diameter of 20 cm. Seeds of Echinochloa oryzicola, Scirpus juncoides, and broad-leaved weeds (Monochoria vaginalis, Rotala indica and Lindernia procumbens) were mixed uniformly with a 1-cm surface layer of the soil, and two seedlings of Eleocharis acicularis were transplanted. The soil was submerged to a level of 3 cm, and rice seedlings in the 2- to 3-leaf stage were transplanted to a depth of 2 cm.

When Echinochloa oryzicola grew to a 2.5-leaf stage, a diluted mixture of each of the active compounds of the invention and another herbicide was applied dropwise. After growing for 20 days, the degrees of injury to rice and the herbicidal activities of the herbicidal composition were examined. The results are shown in Table 9.

TABLE 9

| Herbicides | | | | Herbicidal Acitivity | | | | |
|---|---|---|---|---|---|---|---|---|
| Compound No. | Dosage (g/10a) | Other herbicides | Dosage (g/10a) | Injury to rice | Echinochloa oryzicola | Broad-leaved weeds | Scirpus juncoides | Eleocharis acicularis |
| 176 | 200 | — | — | 0 | 5 | 5 | 5 | 5 |
|  | 100 | — | — | 0 | 3 | 4 | 3.5 | 3 |
|  | 50 | — | — | 0 | 2 | 2.5 | 2.5 | 2 |
| 177 | 50 | — | — | 0 | 5 | 5 | 5 | 5 |
|  | 25 | — | — | 0 | 3.5 | 4 | 4 | 2.5 |
|  | 12.5 | — | — | 0 | 1.5 | 2.5 | 2 | 2 |
| — | — | simetryne | 50 | 0 | 2.5 | 3.5 | 2 | 1 |
| — | — | " | 25 | 0 | 2 | 3 | 1 | 0 |
| — | — | " | 12.5 | 0 | 2 | 2 | 0 | 0 |
| 176 | 50 | " | 12.5 | 0 | 5 | 5 | 5 | 5 |
| 177 | 12.5 | " | 12.5 | 0 | 5 | 5 | 5 | 5 |
| — | — | MT 101 | 200 | 0 | 0 | 3 | 2 | 2 |
| — | — | " | 100 | 0 | 0 | 2 | 1 | 1 |
| 176 | 50 | " | 100 | 0 | 4 | 5 | 4.5 | 4 |
| 177 | 12.5 | " | 100 | 0 | 4.5 | 5 | 5 | 5 |
| — | — | benthiocarb | 200 | 0 | 3.5 | 3 | 2 | 2 |
| — | — | " | 100 | 0 | 3 | 2 | 1 | 2 |
| — | — | " | 50 | 0 | 2 | 1 | 1 | 1 |
| 176 | 50 | " | 50 | 0 | 5 | 5 | 5 | 5 |
| 177 | 12.5 | " | 50 | 0 | 5 | 5 | 5 | 5 |
| — | — | butachlor | 75 | 0 | 3 | 2 | 1.5 | 1 |
| — | — | " | 50 | 0 | 2.5 | 1 | 1 | 0 |
| 176 | 50 | " | 50 | 0 | 5 | 5 | 5 | 5 |
| 177 | 12.5 | " | 50 | 0 | 5 | 5 | 5 | 5 |
| — | — | molinate | 200 | 0 | 3.5 | 2 | 1.5 | 1 |
| — | — | " | 100 | 0 | 3 | 1 | 1 | 1 |
| 176 | 50 | " | 100 | 0 | 5 | 5 | 5 | 5 |
| 177 | 12.5 | " | 100 | 0 | 5 | 5 | 5 | 5 |
| — | — | swep | 500 | 0 | 3 | 2.5 | 2 | 1 |
| — | — | " | 250 | 0 | 2 | 1.5 | 0 | 0 |
| 176 | 50 | " | 250 | 0 | 5 | 4.5 | 4.5 | 4.5 |
| 177 | 12.5 | " | 250 | 0 | 5 | 5 | 5 | 5 |
| — | — | propanil | 500 | 0 | 3 | 2.5 | 1.5 | 2 |
| — | — | " | 250 | 0 | 2 | 2 | 1 | 1 |
| 176 | 50 | " | 250 | 0 | 5 | 5 | 5 | 5 |
| 177 | 12.5 | " | 250 | 0 | 5 | 5 | 5 | 5 |
| — | — | bentazon | 400 | 0 | 0 | 3 | 2.5 | 2.5 |
| — | — | " | 200 | 0 | 0 | 2 | 2.5 | 2.5 |
| 176 | 50 | " | 200 | 0 | 4.5 | 5 | 5 | 5 |
| 177 | 12.5 | " | 200 | 0 | 5 | 5 | 5 | 5 |
| Non-treated lot | | | | 0 | 0 | 0 | 0 | 0 |

TEST EXAMPLE 7

Various crops were sown in soil containing compound No. 177 in a concentration of 3, 10, 30 and 100 ppm respectively calculated as dry soil, and grown for 20 days. Injuries to the crops were then examined, and the results are shown in Table 10.

TABLE 10

| Crops | Concentration (ppm) of compound No. 177 in the soil | | | |
|---|---|---|---|---|
|  | 3 | 10 | 30 | 100 |
| Carrot | 0 | 0 | 0 | 0 |
| Sunflower | 0 | 0 | 0 | 1 |
| Radish | 0 | 0 | 0 | 0.5 |
| Cotton | 0 | 0 | 0 | 1 |
| Soybean | 0 | 0 | 0.5 | 2 |
| Chinese cabbage | 0 | 0 | 0 | 1 |
| Corn | 0 | 0 | 1 | 1.5 |
| Wheat | 0 | 0.5 | 3.5 | 5 |
| Rice | 0 | 0 | 2 | 5 |
| Tomato | 1.5 | 3 | 5 | 5 |
| Welsh onion | 2 | 3.5 | 5 | 5 |
| Beet | 0 | 0.5 | 3.5 | 5 |
| Pumpkin | 0 | 0 | 1 | 2.5 |
| Peanut | 0 | 0 | 0 | 2 |

It is seen from the results shown in Table 10 that carrot has the highest resistance to this herbicidal compound, and next come in order of decreasing resistance sunflower, radish, cotton, peanut, Chinese cabbage, soybean, corn, and pumpkin. Wheat, rice and beet have a medium degree of resistance, and tomato and Welsh onion are least resistant.

TEST EXAMPLE 8

Upland soil (volcanoic ash soil) containing *Digitaria adscendens*, *Amaranthus viridis* and *Polygonum longisetum* and was filled into unglazed pots. Crops were sown to a depth of 1 or 2 cm, and the soil was levelled. Compound No. 177 in each of the concentrations shown in Table 11 was applied, and the crops were grown for 20 days. The herbicidal activities and crop injuries were then examined, and the results are shown in Table 11.

TABLE 11

| Dosage (g/10a) | 3200 | 1600 | 800 | 400 | 200 | 100 | 50 | 0 |
|---|---|---|---|---|---|---|---|---|
| Herbicidal activity | | | | | | | | |
| Digitaria adscendens | 5 | 5 | 5 | 5 | 5 | 5 | 4.5 | 0 |
| Amaranthus varidis | 5 | 5 | 5 | 5 | 5 | 5 | 4.5 | 0 |
| Polygonum longisetum | 5 | 5 | 5 | 5 | 5 | 5 | 4 | 0 |
| Injury rating | | | | | | | | |
| Rice (*) | | | | | | | | |
| −1 | 2 | 1 | 0 | 0 | 0 | 0 | 0 | 0 |
| −2 | 1 | 1 | 0 | 0 | 0 | 0 | 0 | 0 |

TABLE 11-continued

| Dosage (g/10a) | 3200 | 1600 | 800 | 400 | 200 | 100 | 50 | 0 |
|---|---|---|---|---|---|---|---|---|
| Carrot | | | | | | | | |
| −1 | 0 | 0 | 0 | 0 | 0 | 0 | 0 | 0 |
| −2 | 0 | 0 | 0 | 0 | 0 | 0 | 0 | 0 |
| Sunflower | | | | | | | | |
| −1 | 0.5 | 0 | 0 | 0 | 0 | 0 | 0 | 0 |
| −2 | 0 | 0 | 0 | 0 | 0 | 0 | 0 | 0 |
| Cotton | | | | | | | | |
| −1 | 1 | 0.5 | 0 | 0 | 0 | 0 | 0 | 0 |
| −2 | 1 | 0 | 0 | 0 | 0 | 0 | 0 | 0 |
| Soybean | | | | | | | | |
| −1 | 2 | 1 | 0 | 0 | 0 | 0 | 0 | 0 |
| −2 | 2 | 0 | 0 | 0 | 0 | 0 | 0 | 0 |
| Radish | | | | | | | | |
| −1 | 1.5 | 0 | 0 | 0 | 0 | 0 | 0 | 0 |
| −2 | 0.5 | 0 | 0 | 0 | 0 | 0 | 0 | 0 |
| Wheat | | | | | | | | |
| −1 | 5 | 5 | 3 | 0 | 0 | 0 | 0 | 0 |
| −2 | 5 | 5 | 2 | 0 | 0 | 0 | 0 | 0 |
| Corn | | | | | | | | |
| −1 | 3 | 0 | 0 | 0 | 0 | 0 | 0 | 0 |
| −2 | 2 | 0 | 0 | 0 | 0 | 0 | 0 | 0 |
| Peanut | | | | | | | | |
| −1 | 1 | 0 | 0 | 0 | 0 | 0 | 0 | 0 |
| −2 | 1 | 0 | 0 | 0 | 0 | 0 | 0 | 0 |

(*)−1 shows that the seeding depth was 1 cm; and −2 show that it was 2 cm.

It is seen from the results obtained that carrot has the greatest resistance, and dosages 64 times as large as the minimum effective dosage (50 g/10 ares) are quite non-toxic to carrot. Sunflower has the next highest resistance. Dosages about 16 to 32 times as large as the minimum effective dosages are non-toxic or only slightly toxic to cotton, soybean, radish, corn, peanut, and rice. Wheat remains uninjured even when the dosage is 8 times as large as the minimum effective dosage.

TEST EXAMPLE 9

Upland soil containing seeds of various weeds was filled into unglazed pots, and various crops were sown and grown there. When these crops reached a 2- to 2-leaf stage, compound No. 177 was applied to the entire surface of the soil in each of the concentrations shown in Table 12. Fifteen days later, the degrees of injury to the test crops were examined. The results are shown in Table 12.

Annual weeds such as *Digitaria adscendens* could be nearly completely withered when the compound was applied in concentrations of 0.0625 to 0.125%. Carrot remained uninjured when the concentration was up to 1.0%. Next came sunflower, cotton, rice, sugar cane, corn and peanut in order of increasing injury, and in concentrations about 8 times as large as the practical concentrations, there was little or no toxicity to these crops. Some chlorotic parts soon completely recovered. Wheat showed considerable resistance, and remained uninjured when the concentration of the active compound was up to 4 times the practical dosage.

TABLE 12

| Test plants | Concentration (%) | | | | |
|---|---|---|---|---|---|
| | 0.0625 | 0.125 | 0.25 | 0.5 | 1.0 |
| *Digitaris adscendens* | 3.5 | 4.5–5 | 5 | 5 | 5 |
| *Amaranthus viridis* | 4 | 5 | 5 | 5 | 5 |
| *Polygonum longisetum* | 3 | 4.5 | 5 | 5 | 5 |
| *Rumex japonicus* | 3 | 4.5 | 5 | 5 | 5 |
| *Stellaria neglecta* | 4.5 | 5 | 5 | 5 | 5 |
| *Galinsoga ciliata* | 4 | 5 | 5 | 5 | 5 |
| Carrot | 0 | 0 | 0 | 0 | 0 |

TABLE 12-continued

| Test plants | Concentration (%) | | | | |
|---|---|---|---|---|---|
| | 0.0625 | 0.125 | 0.25 | 0.5 | 1.0 |
| Sunflower | 0 | 0 | 0 | 0 | 0.5 |
| Radish | 0 | 0 | 0 | 1 | 3 |
| Soybean | 0 | 0 | 0 | 1 | 3 |
| Cotton | 0 | 0 | 0 | 0 | 3 |
| Wheat | 0 | 0 | 0 | 2.5 | 5 |
| Rice | 0 | 0 | 0 | 0 | 2 |
| Peanut | 0 | 0 | 0 | 1 | 2 |
| Sugar cane | 0 | 0 | 0 | 0 | 1.5 |
| Corn | 0 | 0 | 0 | 0 | 1.5 |

TEST EXAMPLE 10

An upland field was plowed and harrowed uniformly to a depth of 30 cm by an automatic tiller, and in a customary manner, fertilized and seeded. The soil was then treated with compound No. 177. After raising the crops for 20 days, the herbicidal activities of the compound and the degrees of injury to the crops were examined. The results are shown in Table 13. The area of land was 0.5 m × 1 m for each crop.

Carrot did not undergo damage even when the dosage was 3200 g/10 ares. Sunflower, cotton, radish, corn, soybean and peanut were free from phytotoxicity when the dosage was up to 1600 g/10 areas. Next came wheat, Chinese cabbage, welsh onion and tomato in order of decreasing resistance to the herbicidal compound.

Even the tomato having the least resistance showed a medium injury at a dosage 4 times as large as the practical one.

TABLE 13

| Dosage (g/10a) | 3200 | 1600 | 800 | 400 | 200 | 100 | 50 | 0 |
|---|---|---|---|---|---|---|---|---|
| Herbicidal activity | | | | | | | | |
| *Digitaria adsendens* | 5 | 5 | 5 | 5 | 5 | 5 | 4 | 0 |
| *Amaranthus viridis* | 5 | 5 | 5 | 5 | 5 | 5 | 4.5 | 0 |
| *Polygonum longisetum* | 5 | 5 | 5 | 5 | 5 | 5 | 4 | 0 |
| Injury to crops | | | | | | | | |
| Carrot | 0 | 0 | 0 | 0 | 0 | 0 | 0 | 0 |
| Sunflower | 0 | 0 | 0 | 0 | 0 | 0 | 0 | 0 |
| Cotton | 1.5 | 0 | 0 | 0 | 0 | 0 | 0 | 0 |
| Radish | 1.5 | 0 | 0 | 0 | 0 | 0 | 0 | 0 |
| Corn | 1 | 0 | 0 | 0 | 0 | 0 | 0 | 0 |
| Soybean | 1 | 0 | 0 | 0 | 0 | 0 | 0 | 0 |
| Wheat | 3 | 1 | 0 | 0 | 0 | 0 | 0 | 0 |
| Welsh onion | 4 | 3 | 2 | 1 | 0 | 0 | 0 | 0 |
| Tomato | 5 | 4 | 3 | 3 | 0 | 0 | 0 | 0 |
| Chinese cabbage | 3 | 2 | 1.5 | 0 | 0 | 0 | 0 | 0 |
| Peanut | 1 | 0 | 0 | 0 | 0 | 0 | 0 | 0 |

TEST EXAMPLE 11

Twenty vinyl chloride resin rings each having a height of 0.5 cm and a diameter of 10 cm were connected, and filled with upland soil (clay loam). Compound No. 177 was applied to the surface of the ring structure in an amount corresponding to 250 and 500 g/10 ares respectively. Twenty-four hours after the application, artificial rain was let fall in an amount of 20 mm per hour. After another twenty-four hours, the soil was sampled from every 0.5 cm layer below the surface of the soil and placed in Petri dishes. Seeds of *Panicum crus-galli* which had been forced to sprout were sown in the dishes. After growing the seeds for 15 days, the air-dried weight (%) of the terrestrial parts of *Panicum crus-galli* was measured. The results are shown in Table 14.

TABLE 14

| Dosage (g/10a) Soil depth (cm) | 500 | 250 | 0 |
|---|---|---|---|
| 0–0.5 | 0 | 0 | 100 |
| 0.5–1 | 100 | 100 | 100 |
| 1–1.5 | 100 | 100 | 100 |
| 1.5–2 | 100 | 100 | 100 |
| 2–2.5 | 100 | 100 | 100 |
| 2.5–3 | 100 | 100 | 100 |
| 3–3.5 | 100 | 100 | 100 |
| 3.5–4 | 100 | 100 | 100 |

The air-dried weight (%) of the terrestrial parts was determined by collecting only the terrestrial parts of the plant, air-drying them for 3 days indoors with good air circulation, measuring the weight of the dried terrestrial parts, and calculating its percentage based on the air-dried weight in a non-treated lot.

In dosages of 250 and 500 g/10 ares, a marked herbicidal activity was exhibited at a depth within 0 to 0.5 cm from the soil surface, but no activity was noted below 0.5–1 cm. This shows that a rigid herbicide treated layer formed within 0.5 cm from the soil surface.

TEST EXAMPLE 12

Twenty vinyl chloride resin rings each having a height of 0.5 cm and a diameter of 10 cm were connected to form a ring structure, and filled with paddy soil (clay loam). The structure was placed into a pot with a depth of 15 cm, and water was filled to a level of 13 cm. Then, compound No. 177 was applied in a dosage of 100 g and 200 g per 10 ares respectively. The water in the pot was discharged by a siphon so that a decrease of 3 cm in water level was obtained over the period of 24 hours. Water was properly supplied to maintain the water level always at 3 cm above the soil surface. After 48 hours, the soil was sampled from every 0.5 cm layer below the soil surface and placed into a Petri dish. Seeds of *Panicum crus-galli* which had been forced to sprout were sown. After growing them for 15 days, the air-dried weight of the terrestrial parts was determined. The results are shown in Table 15.

It is seen from the results that in dosages of 200 and 100 g/10 ares, a herbicidal activity was recognized in the soil within 0 to 0.5 cm, but no herbicidal activity was noted at 0.5–1 cm or below. Accordingly, rice plants transplanted to a depth of 0.5 to 1 cm or more did not undergo injury.

TABLE 15

| Dosage (g/10a) Soil depth (cm) | 200 | 100 | 0 |
|---|---|---|---|
| 0–0.5 | 0 | 0 | 100 |
| 0.5–1 | 100 | 100 | 100 |
| 1–1.5 | 100 | 100 | 100 |
| 1.5–2 | 100 | 100 | 100 |
| 2–2.5 | 100 | 100 | 100 |
| 2.5–3 | 100 | 100 | 100 |
| 3–3.5 | 100 | 100 | 100 |

TEST EXAMPLE 13

Test lot each with an area of 2 m² were provided in a lawn field (5 years after formation), and compound No. 177 was uniformly sprayed onto these lots at a rate of 100 liters/10 ares. This test was conducted from the middle of May to the middle of June for the purpose of controlling already growing weeds. The results are shown in Table 16.

TABLE 16

| Dosage (g/10a) | 1600 | 800 | 400 | 200 | 100 | Non-treated lot |
|---|---|---|---|---|---|---|
| Herbicidal activity | | | | | | |
| *Digitaris adscendens* | 5 | 5 | 5 | 4.5 | 3.5 | 0 |
| *Polygonum longisetum* | 5 | 5 | 5 | 4.5 | 3 | 0 |
| *Cyperus rotundus* | 5 | 5 | 4.5 | 4 | 2 | 0 |
| *Hydrocotyle sibthorpioides* | 5 | 5 | 5 | 4.5 | 2 | 0 |
| Injury to lawangrass | | | | | | |
| Japanese lawangrass | 0.5 | 0 | 0 | 0 | 0 | 0 |
| Manila grass | 0 | 0 | 0 | 0 | 0 | 0 |

What we claim is:

1. A herbicidal composition comprising a herbicidally effective amount of a 2,3-dicyanopyrazine compound of the general formula

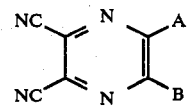

wherein A represents a phenyl group which may contain 1 to 3 substituents selected from the group consisting of halogen atoms, lower alkyl groups, lower alkoxy groups and nitro groups; and B represents a group of the formula

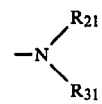

in which $R_{21}$ and $R_{31}$, independently from each other, represent a hydrogen atom, a lower alkyl group which may have 1 or 2 substituents selected from the group consisting of halogen atoms, phenyl groups, hydroxyl groups, carboxyl groups, cyano groups, lower alkoxy groups, lower dialkylamino groups and lower alkoxycarbonyl groups, an allyl group, a phenyl group which may have 1 or 2 substituents selected from the group consisting of halogen atoms and lower alkyl, lower alkoxy and trifluoromethyl group, or a benzyl group, with the proviso that $R_{21}$ and $R_{31}$ do not both represent a hydrogen atom at the same time, or the group of the formula

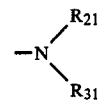

is an ethyleneimino, pyrrolidino, piperidino, hexamethylenimino or morpholino group, and an agronomically acceptable carrier.

2. The herbicidal composition of claim 1 wherein A represents a phenyl group which may have 1 or 2 substituents selected from the class consisting of halogen atoms and lower alkyl groups containing 1 to 3 carbon atoms, and B represents a group of the formula

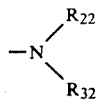

in which $R_{22}$ and $R_{32}$, independently from each other, represent a hydrogen atom, a lower alkyl group which may have a substituent selected from the class consisting of halogen atoms and hydroxyl, lower alkoxy, carboxyl and lower alkoxycarbonyl groups, an allyl group, a phenyl group which may have one substituent selected from the class consisting of halogen atoms and lower alkyl and lower alkoxy groups, or a benzyl group, with the proviso that $R_{22}$ and $R_{32}$ do not represent a hydrogen atom at the same time, or the group of the formula

is an ethylenimino, pyrrolidino or piperidino group.

3. The herbicidal composition of claim 2 wherein B represents an ethylamino, n-propylamino, n- or iso-butylamino, 1-carboxyethylamino, 1-carboxy-n-propylamino, 1-carboxy-iso-butylamino, 1-carboxy-n-pentylamino, dimethylamino, diethylamino, N-methyl-N-carboxymethylamino, allylamino, or ethylenimino group.

4. The herbicidal composition of claim 3 wherein A represents a phenyl group which may have one substituent selected from the class consisting of fluorine, chlorine, bromine and iodine atoms and a methyl group.

5. The herbicidal composition of claim 4 wherein A represents a phenyl, m-fluorophenyl, m-chlorophenyl, m-bromophenyl, m-tolyl or p-tolyl group.

6. The herbicidal composition of claim 5 wherein B represents an ethylamino, n-propylamino or 1-carboxy-n-propylamino group.

7. The herbicidal composition of claim 6 wherein A represents a phenyl, m-fluorophenyl, m-chlorophenyl or m-tolyl group, and B represents an n-propylamino group.

8. The herbicidal composition of claim 1 which further comprises at least one compound selected from the group consisting of α,α,α-trifluoro-2,6-dinitro-N,N-di-n-propyl-p-toluidine, N-methoxymethyl-2,6-diethyl-α-chloroacetanilide, 2,4,6-trichloro-4'-nitrodiphenyl ether, 2-chloro-4,6-bis(ethylamino)-2-triazine, 2-chloro-4-ethylamino-6-isopropylamino-s-triazine, 2-methylthio-4,6-bis(ethylamino)-2-triazine, 5-tert-butyl-3-(2,4-dichloro-5-iso-propoxyphenyl)-1,3,4-oxadiazolin-2-one, S-(4-chlorobenzyl)-N,N-diethylthiol carbamate, 2-chloro-2',6'-diethyl-N-(n-butoxymethyl) S-ethyl-hexahydro-1H-azepine-1-carbothioate and 3,4-dichloro-n-propionanilide.

9. The herbicidal composition of claim 1 which is in the form of a wettable powder, an emulsifiable concentrate, a dust, a granular formulation, an aerosol or a flowable emulsifiable concentrate.

10. The herbicidal composition of claim 1 which contains 1 to 99% by weight of the 2,3-dicyanopyrazine compound based on the weight of the composition.

11. A method for controlling weeds in an agricultural crop which comprises applying to the locus to be protected from the weeds a herbicidally effective amount of a 2,3-dicyanopyrazine compound of the general formula

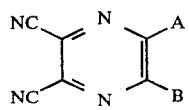

(I)

wherein A represents a phenyl group which may contain 1 to 3 substituents selected from the group consisting of halogen atoms, lower alkyl groups, lower alkoxy groups and nitro groups; and B represents a group of the formula

in which $R_{21}$ and $R_{31}$, independently from each other, represent a hydrogen atom, a lower alkyl group which may have 1 or 2 substituents selected from the group consisting of halogen atoms, phenyl groups, hydroxyl groups, carboxyl groups, cyano groups, lower alkoxy groups, lower dialkylamino groups and lower alkoxycarbonyl groups, an allyl group, a phenyl group which may have 1 or 2 substituents selected from the group consisting of halogen atoms and lower alkyl, lower alkoxy and trifluoromethyl group, or a benzyl group, with the proviso that $R_{21}$ and $R_{31}$ do not both represent a hydrogen atom at the same time, or the group of the formula

is an ethylenimino, pyrrolidino, piperidino, hexamethylenimino or morpholino group, and an agronomically acceptable carrier.

12. The method of claim 11 wherein the agricultural crop is selected from the group consisting of rice, wheat, barley, cotton, corn, peanuts, rapeseed, sunflowers, safflowers, sugar canes and soy beans.

13. The method of claim 11 wherein the active compound is applied in an amount of 20 to 1000 g per 10 ares.

14. The method of claim 51 wherein the active compound is sprayed terrestrially or aerially to the locus to be protected from weeds before or after the seeding or transplantation.

* * * * *